US009932411B2

(12) United States Patent
Terrett et al.

(10) Patent No.: US 9,932,411 B2
(45) Date of Patent: Apr. 3, 2018

(54) ANTIBODIES

(71) Applicant: Oxford BioTherapeutics Ltd, Abingdon (GB)

(72) Inventors: Jonathan Alexander Terrett, Sunnyvale, CA (US); Chetana Rao-Naik, Walnut Creek, CA (US); Haichun Huang, Fremont, CA (US); Sarah Pogue, Redwood City, CA (US); Erika Meaddough, Gilroy, CA (US); Michelle Kuhne, San Francisco, CA (US); Chin Pan, Los Altos, CA (US)

(73) Assignee: Oxford BioTherapeutics Ltd, Abingdon (GB)

( * ) Notice: Subject to any disclaimer, the term of this patent is extended or adjusted under 35 U.S.C. 154(b) by 22 days.

(21) Appl. No.: 15/037,929

(22) PCT Filed: Nov. 25, 2014

(86) PCT No.: PCT/GB2014/053470
§ 371 (c)(1),
(2) Date: May 19, 2016

(87) PCT Pub. No.: WO2015/075477
PCT Pub. Date: May 28, 2015

(65) Prior Publication Data
US 2016/0289338 A1 Oct. 6, 2016

Related U.S. Application Data

(60) Provisional application No. 61/908,371, filed on Nov. 25, 2013.

(51) Int. Cl.
C07K 16/40 (2006.01)
C07K 16/30 (2006.01)
A61K 47/68 (2017.01)
A61K 39/00 (2006.01)

(52) U.S. Cl.
CPC .......... *C07K 16/40* (2013.01); *A61K 47/6803* (2017.08); *A61K 47/6869* (2017.08); *A61K 47/6871* (2017.08); *C07K 16/30* (2013.01); *C07K 16/3015* (2013.01); *C07K 16/3046* (2013.01); *C07K 16/3069* (2013.01); *A61K 2039/505* (2013.01); *C07K 2317/31* (2013.01); *C07K 2317/34* (2013.01); *C07K 2317/565* (2013.01); *C07K 2317/732* (2013.01); *C07K 2317/734* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 5,972,616 | A | 10/1999 | O'Brien et al. |
|---|---|---|---|
| 6,451,500 | B1 | 9/2002 | Leon |
| 6,649,741 | B1 | 11/2003 | O'Brien et al. |
| 6,903,201 | B2 | 6/2005 | Padigaru |
| 7,022,821 | B1 | 4/2006 | O'Brien et al. |
| 7,030,231 | B1 | 4/2006 | Craik et al. |
| 7,105,333 | B2 | 9/2006 | Madison et al. |
| 7,112,430 | B2 | 9/2006 | Madison et al. |
| 7,125,703 | B2 | 10/2006 | Madison et al. |
| 7,172,892 | B2 | 2/2007 | Madison et al. |
| 7,227,009 | B2 | 6/2007 | Craik et al. |
| 7,291,462 | B2 | 11/2007 | O'Brien et al. |
| 7,355,015 | B1 | 4/2008 | Dickson et al. |
| 7,488,813 | B2 | 2/2009 | Pollock et al. |
| 8,205,227 | B1 | 6/2012 | Del Sesto et al. |
| 8,420,091 | B2 | 4/2013 | Rohlff et al. |
| 8,863,186 | B2 | 10/2014 | Del Sesto et al. |
| 2006/0171884 | A1 | 8/2006 | Foltz et al. |
| 2011/0182897 | A1* | 7/2011 | Hultberg ............... C07K 16/10 424/134.1 |
| 2012/0272269 | A1 | 10/2012 | Del Sesto et al. |

FOREIGN PATENT DOCUMENTS

| WO | 0123524 A2 | 4/2001 |
|---|---|---|
| WO | 0129056 A1 | 4/2001 |
| WO | 01/057194 A2 | 8/2001 |
| WO | 0157194 A2 | 8/2001 |
| WO | 2004058688 A1 | 7/2004 |

(Continued)

OTHER PUBLICATIONS

U.S. Appl. No. 12/701,556, filed Feb. 6, 2010, Eric E. Del Sesto.
U.S. Appl. No. 13/485,718, filed May 31, 2012, Eric E. Del Sesto.
U.S. Appl. No. 12/701,556, Feb. 21, 2012.
U.S. Appl. No. 13/485,718, Jun. 9, 2014.
U.S. Appl. No. 13/485,718, May 10, 2013.
U.S. Appl. No. 13/485,718, Oct. 25, 2012.
Abcam AB41263 ST14 Stemregion.
Abcam Scientific Supp Cust Serv Anti-ST14 antibody (ab28267).
Ahmed, S. et al., "Identification of membrane-bound serine proteinase matriptase as processing enzyme of insulin-like growth factor binding protein-related protein-1 (IGFBP-rP1/angiomodulin/mac25).," J Febs, 273(3):615-627 (2006).
Aimes, R. et al., "Endothelial cell serine proteases expressed during vascular morphogenesis and angiogenesis," Thromb Haem 89(3):561-572 (2003).

(Continued)

*Primary Examiner* — Brad Duffy
(74) *Attorney, Agent, or Firm* — Nelson Mullins Riley & Scarborough LLP; Jane E. Remillard, Esq.; Jill Gorny Sloper, Esq.

(57) ABSTRACT

The invention provides antibodies which bind to the extracellular domain of the Tyrosine-protein kinase transmembrane receptor Matriptase. Nucleic acid molecules encoding the antibodies, expression vectors, host cells and methods for expressing the antibodies are also provided. The antibodies may be used for the treatment of cancer, including gastric cancer, colorectal cancer, prostate cancer, breast cancer, ovarian cancer lung cancer, preferably SCLC, esophageal cancer, head and neck cancer, pancreatic cancer, lymphoma preferably non-Hodgkin's lymphoma and skin cancer.

24 Claims, 13 Drawing Sheets

(56) References Cited

FOREIGN PATENT DOCUMENTS

| WO | 2006/068975 A2 | 6/2006 |
|---|---|---|
| WO | 20060068975 A2 | 6/2006 |
| WO | 2007047796 A2 | 4/2007 |
| WO | 2009/020645 A2 | 2/2009 |
| WO | 2011/063127 A1 | 5/2011 |
| WO | 2015/075477 A1 | 5/2015 |

OTHER PUBLICATIONS

Alef, T. et al., "Ichthyosis, follicular atrophoderma, and hypotrichosis caused by mutations in ST14 is associated with impaired profilaggrin processing," J Invenst Derm, 129(4):862-869 (2009).

Andre, M. et al., "Proteomic analysis of the tetraspanin web using LC-ESI-MS/MS and MALDI-FTICR-MS," Proteomics, 6(5):1437-1449 (2006).

Annual Meeting Japanese Cancer Association 63:269 P0608 (2004).

Anonymous, "Anti-STI4 antibody-stem region (ab28267)", 2012, retrieved from the Abcam Internet website.

Basel-Vanagaite, L. et al., "Autosomal recessive ichthyosis with hypotrichosis caused by a mutation in ST14, encoding type II transmembrane serine protease matriptase," Am J Hum Genet., 80(3):467-477 (2007).

Benaud, C. et al., "Deregulated activation of matriptase in breast cancer cells," Clin Exp Meta., 19(7):639-649 (2002).

Benaud, C. et al., "Regulation of the activity of matriptase on epithelial cell surfaces by a blood-derived factor," Eur J Biochem., 268(5):1439-1447 (2001).

Benaud, C. et al., "Sphingosine 1-phosphate, present in serum-derived lipoproteins, activates matriptase," J Biol Chem., 277(12):10539-10546 (2002).

Betsunoh, H. et al., "Clinical relevance of hepsin and hepatocyte growth factor activator inhibitor type 2 expression in renal cell carcinoma," Can Science, 98(4):491-498 (2007).

Bhatt, A. et al., "Adhesion signaling by a novel mitotic substrate of src kinases," Oncogene, 24:5333-5343 (2005).

Bhatt, A. et al., "Coordinate expression and functional profiling identify an extracellular proteolytic signaling pathway," PNAS, 104(14):5771-5776 (2007).

Bhatt, A. et al., "Quantitation of membrane type serine protease 1 (MT-SP1) in transformed and normal cells," Biol Chem., 384(2):257-266 (2003).

Bugge, T., et al., "Matripase," UCSD Nat Mol., 6 pages (2007).

Cao, J. et al., "A novel serine protease SNC19 associated with human colorectal cancer," Chin Med J., 114(7):726-730 (2001).

Chen, M. et al., "Prostasin induces protease-dependent and independent molecular changes in the human prostate carcinoma cell line PC-3," Biochem Biophys Acta., 1773(7):1133-1140 (2007).

Chen, M. et al., "The epidermal growth factor receptor (EGFR) is proteolytically modified by the Matriptase-Prostasin serine protease cascade in cultured epithelial cells," Bioc Biop Acta.,1783(5):896-903 (2008).

Cheng, M. et al., "Expression of EMMPRIN and matriptase in esophageal squamous cell carcinoma: correlation with clinicopathological parameters," Dis Esoph., 19(6):482-486 (2006).

Cho, E. et al., "N-terminal processing is essential for release of epithin, a mouse type II membrane serine protease," JBC, 276(48):44581-44589 (2001).

Cleator et al., "Gene expression patterns for doxorubicin (Adriamycin) and cyclophosphamide (cytoxan) (AC) response and resistance," Breast Can Res. Treat., 95(3):229-233 (2006).

Desilets, A. et al., "Inhibition of human matriptase by eglin c variants," FEBS Lett., 580(9):2227-2232 (2006).

Ding, K. et al., "Effect of SNC19/ST14 gene overexpression on invasion of colorectal cancer cells," World J Gastro., 11(36):5651-5654 (2005).

Enyedy, I. et al., "Structure-based approach for the discovery of bis-benzamidines as novel inhibitors of matriptase.," J Med Chem., 44(9):1349-1355 (2001).

Everts et al., Drugs of the Future 30(1):1067-1076 (2005).

Farady, C. et al., "The mechanism of inhibition of antibody-based inhibitors of membrane-type serine protease 1 (MT-SP1).," J Mol Biol.,369(4):1041-1051 (2007).

Forbs, D. et al., "In vitro inhibition of matriptase prevents invasive growth of cell lines of prostate and colon carcinoma," Int J Oncol., 27(4):1061-1070 (2005).

Friedrich, R. et al., "Catalytic domain structures of MT-SP1/matriptase, a matrix-degrading transmembrane serine proteinase," J Biol Chem., 277(3):2160-2168 (2002).

Galkin, A. et al., "CVS-3983, a selective matriptase inhibitor, suppresses the growth of androgen independent prostate tumor xenografts," Prostate, 61(3):228-235 (2004).

Ge, W. et al., "Protein interaction analysis of ST14 domains and their point and deletion mutants," J Biol Chem., 281(11):7406-7412 (2006).

Habbe, N. et al., "Identification of methylation-associated gene expression in neuroendocrine pancreatic tumor cells," Pancreatology, 7:352-359 (2007).

Hoang, C. et al., "Gene expression profiling identifies matriptase overexpression in malignant mesothelioma," Chest, 125(5):1843-1852 (2004).

Hooper, J. et al., "Type II transmembrane serine proteases. Insights into an emerging class of cell surface proteolytic enzymes," J Biol Chem., 276(2):857-860 (2001).

Hung, R-J., et al., "Assembly of adherens junctions is required for sphingosine 1-phosphate-induced matriptase accumulation and activation at mammary epithelial cell—cell contacts," Am J Phys Cell Phys.,286(5): c1159-c1169 (2004).

Ihara, S. et al., "Addition of beta1-6 GlcNAc branching to the oligosaccharide attached to Asn 772 in the serine protease domain of matriptase plays a pivotal role in its stability and resistance against trypsin," Glycobio., 14(2):139-146 (2004).

Ihara, S. et al., "Prometastatic effect of N-acetylglucosaminyltransferase V is due to modification and stabilization of active matriptase by adding beta 1-6 GlcNAc branching," J Biol Chem., 277(19):16960-16967 (2002).

International Preliminary Report on Patentability, PCT/GB2014/053470, dated May 31, 2016, 5 pages.

International Search Report and Written Opinion, PCT/GB2014/053470, dated Feb. 13, 2015, 8 pages.

Ito, Y. et al., "Co-expression of matriptase and N-acetylglucosaminyltransferase V in thyroid cancer tissues—its possible role in prolonged stability in vivo by aberrant glycosylation," Glycobio., 16(5):368-374 (2006).

Jarzab, B. et al., "Gene expression profile of papillary thyroid cancer: sources of variability and diagnostic implications," Cancer Res., 65(4):1587-1597 (2005).

Jin et al., "Expression of Serine Protease Matriptase in Renal Cell Carcinoma: Correlation of Tissue Microarray Immunohistochemical Expression Analysis Results with Clinicopathological Parameters," Can Sci., 97(12):1327-1344 (2006).

Jin, J. et al., "Expression of the serine protease, matriptase, in breast ductal carcinoma of Chinese women: correlation with clinicopathological parameters," Histol Histop., 22(3):305-309 (2006).

Jin, J. et al., "Expression of serine protease matriptase in renal cell carcinoma: correlation of tissue microarray immunohistochemical expression analysis results with clinicopathological parameters," Int J Surg Path., 14(1):65-72 (2006).

Jin, J.S. et al., "Increasing expression of serine protease matriptase in ovarian tumors: tissue microarray analysis of immunostaining score with clinicopathological parameters," Mod Path., 19(3):447-452 (2006).

Jin, X. et al., "Production of soluble matriptase by human cancer cell lines and cell surface activation of its zymogen by trypsin," J Cell Bio., 95(3):632-647 (2005).

Johnson, M. et al., "Possible role of matriptase in the diagnosis of ovarian cancer," Exp Rev Mol Diagn., 3(3):331-338 (2003).

Journal Japan Society Obstetrics and Gynecology 56(2):384 S254 5-5 (2004).

Kang, J. et al., "Tissue microarray analysis of hepatocyte growth factor/Met pathway components reveals a role for Met, matriptase,

(56) References Cited

OTHER PUBLICATIONS and hepatocyte growth factor activator inhibitor 1 in the progression of node-negative breast cancer," Can Res., 63:1101-1105 (2003).
Kilpatrick, L. et al., "Initiation of plasminogen activation on the surface of monocytes expressing the type II transmembrane serine protease matriptase," Blood, 108(8):2616-2623 (2006).
Kirpotin et al., "Sterically Stabilized Anti-HER2 Immunoliposomes: Design and Targeting to Human Breast Cancer Cell In Vitro," Biochem., 36:66-75 (2007).
Kiyomiya, K. et al., "Matriptase activation and shedding with HAI-1 is induced by steroid sex hormones in human prostate cancer cells, but not in breast cancer cells," Am J Phys Cell Phys., 291(1):C40-C49 (2006).
Le Naour, F. et al., "Profiling of the tetraspanin web of human colon cancer cells," Mol Cell Prot., 5:845-857(2006).
Lee et al., "Increased expression of matriptase is associated with histopathologic grades of cervical neoplasia," Hum Path., 36(6):626-633 (2005).
Lee et al., "Matrix-Degrading Type II Transmembrane Serine Protease Matriptase: Its Role in Cancer Development and Malignancy," J Can Mol 2(5):183-190 (2006).
Lee et al., Am J Physiol Cell Physiol 293(1):C95-C1050 (2007).
Lee et al., Korean J Obstet Gyne 47(12):2465-2471 (2004).
Lee, M. et al., "Simultaneous activation and hepatocyte growth factor activator inhibitor 1-mediated inhibition of matriptase induced at activation foci in human mammary epithelial cells," Am J Physiol Cell Physiol., 288(4):C932-C941 (2005).
Lee, S. et al., "Activation of hepatocyte growth factor and urokinase/plasminogen activator by matriptase, an epithelial membrane serine protease," J Bio Chem., 275(47):36720-36725 (2000).
Li, P. et al., "Design and synthesis of novel and potent inhibitors of the type II transmembrane serine protease, matriptase, based upon the sunflower trypsin inhibitor-1," J Med Chem., 50(24):5976-5983 (2007).
Lin, C. et al., "Molecular cloning of cDNA for matriptase, a matrix-degrading serine protease with trypsin-like activity," J Biol Chem., 274(26):18231-18236 (1999).
Lin, C. et al., "Purification and characterization of a complex containing matriptase and a Kunitz-type serine protease inhibitor from human milk," J Biol Chem., 274(26):18237-18242 (1999).
List, K. et al., "Delineation of matriptase protein expression by enzymatic gene trapping suggests diverging roles in barrier function, hair formation, and squamous cell carcinogenesis," Am J Path., 168(5):1513-1525 (2006).
List, K. et al., "Deregulated matriptase causes ras-independent multistage carcinogenesis and promotes ras-mediated malignant transformation," Genes Dev., 19(16):1934-1950 (2005).
List, K. et al., "Loss of proteolytically processed filaggrin caused by epidermal deletion of Matriptase/MT-SP1," J Cell Bio., 163(4):901-910 (2003).
List, K. et al., "Matriptase/MT-SP1 is required for postnatal survival, epidermal barrier function, hair follicle development, and thymic homeostasis," Ongene, 21(23):3496-3779 (2002).
List, K. et al., "Matriptase: potent proteolysis on the cell surface," Mol Med 12(1-3):1-7 (2006).
Mildner, M. et al., "Gene silencing in a human organotypic skin model.," Bioc Biop Res Comm., 348(1):76-82 (2006).
Mori, M. et al., "The cytotrophoblast layer of human chorionic villi becomes thinner but maintains its structural integrity during gestation," Rio Rep., 76:164-172 (2007).
Netzel-Arnett, S. et al., "Evidence for a matriptase-prostasin proteolytic cascade regulating terminal epidermal differentiation," J Biol Chem., 281(44):32941-32945 (2006).
Niv, R. et al., "Targeting multidrug resistant tumor cells with a recombinant single-chain FV fragment directed to P-glycoprotein," Int J Cancer., 94:864-872 (2001).
Oberst, M et al., "The activation of matriptase requires its noncatalytic domains, serine protease domain, and its cognate inhibitor," JBC 278(28):26773-26779 (2003).

Oberst, M. et al., "Characterization of matriptase expression in normal human tissues," J Histochem Cytochem., 51(8):1017-1025 (2003).
Oberst, M. et al., "Expression of the serine protease matriptase and its inhibitor HAI-1 in epithelial ovarian cancer: correlation with clinical outcome and tumor clinicopathological parameters," Clin Can Res., 8(4):1101-1107 (2002).
Oberst, M. et al., "HAI-1 regulates activation and expression of matriptase, a membrane-bound serine protease," Am J Phys Cell Phys., 289(2):C462-C470 (2005).
Oberst, M. et al., "Matriptase and HAI-1 are expressed by normal and malignant epithelial cells in vitro and in vivo," Am j Path., 158(4):1301-1311 (2001).
Pedley et al., "Pharmacokinetics of Monoclonal Antibodies," Clin Immuno., 6(1):54-67 (1996).
Planes, C. et al., "Regulation of the epithelial Na+ channel by peptidases," Curr Top Dev Biol., 78:23-46 (2007).
Qiu, D. et al., "Roles and regulation of membrane-associated serine proteases," Bioc Soc Trans., 35(3):583-587 (2007).
Riddick, A. et al., "Identification of degradome components associated with prostate cancer progression by expression analysis of human prostatic tissues," Br J Can., 92(12):2171-2180 (2005).
Saleem, M et al., "A novel biomarker for staging human prostate adenocarcinoma: overexpression of matriptase with concomitant loss of its inhibitor, hepatocyte growth factor activator inhibitor-1," Can Epi Biomark., 15(2):217-227 (2006).
Sanders, A. et al., "Genetic reduction of matriptase-1 expression is associated with a reduction in the aggressive phenotype of prostate cancer cells in vitro and in vivo," J Exp Ther Onco, 6(1):39-48 (2006).
Santin, A. et al., "Gene expression profiles in primary ovarian serous papillary tumors and normal ovarian epithelium: identification of candidate molecular markers for ovarian cancer diagnosis and therapy," Int J Can., 112(1):14-25 (2004).
Santin, A. et al., "The novel serine protease tumor-associated differentially expressed gene-15 (matriptase/MT-SP1) is highly overexpressed in cervical carcinoma," Cancer, 98(9):1898-1904 (2003).
Sato, N. "Discovery of novel targets for aberrant methylation in pancreatic carcinoma using high-throughput microarrays," Can Res., 63(13):3735-3742 (2003).
Satomi, S. et al., "A role for membrane-type serine protease (MT-SP1) in intestinal epithelial turnover," Bioc Biop Res Com., 287(4):995-1002 (2001).
Seitz, I. et al., "Membrane-type serine protease-1/matriptase induces interleukin-6 and -8 in endothelial cells by activation of protease-activated receptor-2: potential implications in atherosclerosis," Art Thromb Vasc Biol., 27(4):769-775 (2007).
Shi, Y. et al., "Study on post-translational processing and active forms of the novel metastasis-associated protein SNC19," Zhejiang Da Xue Xue Bao Yi Xue Ban, 34(1):38-42 (2005).
Siddiqui, S. et al., "Coexpression of beta1,6-N-acetylglucosaminyltransferase V glycoprotein substrates defines aggressive breast cancers with poor outcome," Can Epi Biom Prev., 14(11);2517-2523 Part 1 (2005).
Steinmetzer, T. et al., "Secondary amides of sulfonylated 3-amidinophenylalanine. New potent and selective inhibitors of matriptase," J Med Chem., 49(14):4116-4126 (2006).
Stoop, A. et al., "Engineering of a macromolecular scaffold to develop specific protease inhibitors," Nat Biotech., 21:1063-1068 (2003).
Sun, J. et al., "Potent and selective inhibition of membrane-type serine protease 1 by human single-chain 28 antibodies," Biochem 42(4):895-900 (2003).
Sun, L. et al., "SNC19/ST14 gene transfection and expression influence the biological behavior of colorectal cancer cells," Zhonghua Yi Xue Za Zhi, 84(10):843-848 (2004).
Suzuki, M. et al., "Bikunin target genes in ovarian cancer cells identified by microarray analysis," J Biol Chem., 278(17):14640-14646 (2003).

(56) References Cited

OTHER PUBLICATIONS

Suzuki, M. et al., "Inhibition of tumor invasion by genomic down-regulation of matriptase through suppression of activation of receptor-bound pro-urokinase," J Biol Chem., 279(15):14899-14908 (2004).

Szabo, R. et al., "Matriptase-3 is a novel phylogenetically preserved membrane-anchored serine protease with broad serpin reactivity.," J Biochem. 390:231-242 (2005).

Takeuchi, T. et al., "Cellular localization of membrane-type serine protease 1 and identification of protease-activated receptor-2 and single-chain urokinase-type plasminogen activator as substrates," JBC, 275(34):26333-26342 (2000).

Takeuchi, T. et al., "Reverse biochemistry: use of macromolecular protease inhibitors to dissect complex biological processes and identify a membrane-type serine protease in epithelial cancer and normal tissue," PNAS, 96(20):11054-11061 (1999).

Tanimoto, H. "Ovarian tumor cells express a transmembrane serine protease: a potential candidate for early diagnosis and therapeutic intervention," Tumour Bio., 22(2):104-114(2001).

Tanimoto, H. et al., "Transmembrane serine protease TADG-15 (ST14/Matriptase/MT-SP1): expression and prognostic value in ovarian cancer," Br J Cancer., 92(2):278-283 (2005).

Tsai, W. et al., "Increasing EMMPRIN and matriptase expression in hepatocellular carcinoma: tissue microarray analysis of immunohistochemical scores with clinicopathological parameters," Histopath., 49(4):388-395 (2006).

Tsuzuki, S. et al., "Evidence for the occurrence of membrane-type serine protease 1/matriptase on the basolateral sides of enterocytes," J Biochem., 388(2):679-687 (2005).

Uhland, K. et al.,"Matriptase and its putative role in cancer," Cell Mol Life Sci., 63(24):2968-2978 (2006).

Vettel, U. et al., "Charge-dependent binding of granzyme A (MTSP-1) to basement membranes," Eur J Imm., 23(1):279-282 (1993).

Vogel, L. et al., "The ratio of Matriptase/HAI-1 mRNA is higher in colorectal cancer adenomas and carcinomas than corresponding tissue from control individuals," BMC Can., 6:176 (8 pages) (2006).

Welm, A. et al., "The macrophage-stimulating protein pathway promotes metastasis in a mouse model for breast cancer and predicts poor prognosis in humans," PNAS, 104(18):7570-7575 (2007).

Yamasaki Y. et al., "Inhibition of membrane-type serine protease 1/matriptase by natural and synthetic protease inhibitors," J Nut Sci Vit., 49(1):27-32 (2003).

Zeeuwen, P. et al., "Epidermal differentiation: the role of proteases and their inhibitors," Eur J Cell Biol., 83(11-12): 761-773 (2004).

Zeng, L. et al., "Expression of serine protease SNC19/matriptase and its inhibitor hepatocyte growth factor activator inhibitor type 1 in normal and malignant tissues of gastrointestinal tract," World J Gastro., 11(39):6202-6207 (2005).

Zhang, Y. et al., "Assignment1 of human putative tumor suppressor genes ST13 (alias SNC6) and ST14 (alias SNC19) to human chromosome bands 22q13 and 11q24→q25 by in situ hybridization," Cyto Cell Gene, 83(1-2):56-57 (1998).

Information Disclosure Submission Under 37 C.F.R. § 1.56, dated Oct. 23, 2017, 1 page.

* cited by examiner

```
SEQ ID NO: 26    MGSDRARKGGGGPKDFGAGLKYNSRHEKVNGLEEGVEFLPVNNVKKVEKH  50
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    GPGRWVVLAAVLIGLLLVLLGIGFLVWHLQYRDVRVQKVFNGYMRITNEN  100
SEQ ID NO: 24    -----------------------------------VQKVFNGYMRITNEN  15
SEQ ID NO: 23    -----------------------------------VQKVFNGYMRITNEN  15
SEQ ID NO: 22    -----------------------------------VQKVFNGYMRITNEN  15
SEQ ID NO: 21    -----------------------------------VQKVFNGYMRITNEN  15
                                                    **************

SEQ ID NO: 26    FVDAYENSNSTEFVSLASKVKDALKLLYSGVPFLGPYHKESAVTAFSEGS  150
SEQ ID NO: 24    FVDAYENSNSTEFVSLASKVKDALKLLYSGVPFLGPYHKESAVTAFSEGS  65
SEQ ID NO: 23    FVDAYENSNSTEFVSLASKVKDALKLLYSGVPFLGPYHKESAVTAFSEGS  65
SEQ ID NO: 22    FVDAYENSNSTEFVSLASKVKDALKLLYSGVPFLGPYHKESAVTAFSEG-  64
SEQ ID NO: 21    FVDAYENSNSTEFVSLASKVKDALKLLYSGVPFLGPYHKESAVTAFSEGS  65
                 *************************************************

SEQ ID NO: 26    VIAYYWSEFSIPQHLVEEAERVMAEERVVMLPPRARSLKSFVVTSVVAFP  200
SEQ ID NO: 24    VIAYYWSEFSIPQHLVEEAERVMAEERVVMLPPRARSLKSFVVTSVVAFP  115
SEQ ID NO: 23    VIAYYWSEFSIPQHLVEEAERVMAEERVVMLPPRARSLK-----------  104
SEQ ID NO: 22    --------------------------------------------------
SEQ ID NO: 21    VIAYYWSEFSIPQHLVEEAERVMAEERVVMLPPRARSLKSFVVTSVVAFP  115

SEQ ID NO: 26    TDSKTVQRTQDNSCSFGLHARGVELMRFTTPGFPDSPYPAHARCQWALRG  250
SEQ ID NO: 24    TDSK----------------------------------------------  119
SEQ ID NO: 23    --------------------------------------------------
SEQ ID NO: 22    --------------------------------------------------
SEQ ID NO: 21    T-------------------------------------------------  116

SEQ ID NO: 26    DADSVLSLTFRSFDLASCDERGSDLVTVYNTLSPMEPHALVQLCGTYPPS  300
SEQ ID NO: 24    --------------------------------------------------
SEQ ID NO: 23    --------------------------------------------------
SEQ ID NO: 22    --------------------------------------------------
SEQ ID NO: 21    --------------------------------------------------
```

*FIG. 1b*

```
SEQ ID NO: 26    YNLTFHSSQNVLLITLITNTERRHPGFEATFFQLPRMSSCGGRLRKAQGT  350
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    FNSPYYPGHYPPNIDCTWNIEVPNNQHVKVRFKFFYLLEPGVPAGTCPKD  400
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    YVEINGEKYCGERSQFVVTSNSNKITVRFHSDQSYTDTGFLAEYLSYDSS  450
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    DPCPGQFTCRTGRCIRKELRCDGWADCTDHSDELNCSCDAGHQFTCKNKF  500
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    CKPLFWVCDSVNDCGDNSDEQGCSCPAQTFRCSNGKCLSKSQQCNGKDDC  550
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    GDGSDEASCPKVNVVTCTKHTYRCLNGLCLSKGNPECDGKEDCSDGSDEK  600
SEQ ID NO: 24    --------------------------------------------------
SEQ ID NO: 23    --------------------------------------------------
SEQ ID NO: 22    --------------------------------------------------
SEQ ID NO: 21    --------------------------------------------------
```

FIG. 1b Cont'd

```
SEQ ID NO: 26    DCDCGLRSFTRQARVVGGTDADEGEWPWQVSLHALGQGHICGASLISPNW  650
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    LVSAAHCYIDDRGFRYSDPTQWTAFLGLHDQSQRSAPGVQERRLKRIISH  700
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    PFFNDFTFDYDIALLELEKPAEYSSMVRPICLPDASHVFPAGKAIWVTGW  750
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    GHTQYGGTGALILQKGEIRVINQTTCENLLPQQITPRMMCVGFLSGGVDS  800
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    CQGDSGGPLSSVEADGRIFQAGVVSWGDGCAQRNKPGVYTRLPLFRDWIK  850
SEQ ID NO: 24    --------------------------------------------------
SEQ ID NO: 23    --------------------------------------------------
SEQ ID NO: 22    --------------------------------------------------
SEQ ID NO: 21    --------------------------------------------------

SEQ ID NO: 26    ENTGV  855
SEQ ID NO: 24    -----
SEQ ID NO: 23    -----
SEQ ID NO: 22    -----
SEQ ID NO: 21    -----
```

*FIG. 1b* Cont'd

```
SEQ ID No: 17    EVQLLESGGGLVQPGGSLRLSCAASGFTFSSYAMSW
SEQ ID No: 18    ------------------------------------
SEQ ID No: 1     EVQLLESGGGLVQPGGSLRLSCAASGFTFRNYDMSW
                 *****************************  * ***

SEQ ID No: 17    VRQAPGKGLEWVSAISGSGGSTYYADSVKGRFTISR
SEQ ID No: 18    ------------------------------------
SEQ ID No: 1     VRQAPGKGLEWVSSISYSGGSTYYADSVKGRFTISR
                 ************ ** ********************

SEQ ID No: 17    DNSKNTLYLQMNSLRAEDTAVYYCAK----------
SEQ ID No: 18    -------------------------RGATPFDYWG
SEQ ID No: 1     DNSKNTLSLQMNSLRAEDTAVYYCAKRGATPFDYWG
                 *******  ***************************

SEQ ID No: 17    ---------
SEQ ID No: 18    QGTLVTVSS
SEQ ID No: 1     QGSLVTVSS
                 ** ******
```

FIG. 2a

```
SEQ ID No: 19    EIVLTQSPGTLSLSPGERATLSCRASQSVSSSYLAW
SEQ ID No: 20    ------------------------------------
SEQ ID No: 2     EIVLTQSPGTLSLSPGERATLSCRASQSVSSSYLAW
                 ************************************

SEQ ID No: 19    YQQKPGQAPRLLIYGASSRATGIPDRFSGSGSGTDF
SEQ ID No: 20    ------------------------------------
SEQ ID No: 2     YQQKPGQAPRLLIYGASSRATGIPDRFSGSGSGTDF
                 ************************************

SEQ ID No: 19    TLTISRLEPEDFAVYYCQQYGSSP------------
SEQ ID No: 20    ------------------------YTFGQGTKLEIK
SEQ ID No: 2     TLTISRLEPEDFAVYYCQQYGSSPYTFGQGTKLEIK
                 ************************************
```

FIG. 2b

SEQUENCE LISTING

<160> NUMBER OF SEQ ID NOS: 36

<210> SEQ ID NO 1
<211> LENGTH: 117
<212> TYPE: PRT
<213> ORGANISM: Human

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Asp Met Ser Trp Val Arg Gln Ala Pro Gly Lys Gly Leu Glu Trp Val
        35                  40                  45

Ser Ser Ile Ser Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Arg Gly Ala Thr Pro Phe Asp Tyr Trp Gly Gln Gly Ser Leu
            100                 105                 110

Val Thr Val Ser Ser
        115

<210> SEQ ID NO 2
<211> LENGTH: 108
<212> TYPE: PRT
<213> ORGANISM: Human

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 3
<211> LENGTH: 351
<212> TYPE: DNA
<213> ORGANISM: Human

<400> SEQUENCE: 3
gaggtgcaac tgttggagtc tgggggaggc ttggtacagc ctggggggtc cctgagactc    60
tcctgtgcag cctctggatt cacctttagg aactatgaca tgagctgggt ccgccaggct   120
ccagggaagg ggctggagtg ggtctcaagt attagttata gtggtggtag cacatactac   180
gcagactccg tgaagggccg gttcaccatc tccagagaca attccaagaa tacgctgtct   240
ctgcaaatga acagcctgag agccgaggac acggccgttt attactgtgc gaaaggggg    300 gctaccccat tgactactg gggccaggga tccctggtca ccgtctcctc a             351

<210> SEQ ID NO 4
<211> LENGTH: 324
<212> TYPE: DNA
<213> ORGANISM: Human

<400> SEQUENCE: 4
gaaattgtgt tgacgcagtc tccaggcacc ctgtctttgt ctccagggga aagagccacc    60
ctctcctgca gggccagtca gagtgttagc agcagttact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgta cacttttggc   300

```
cagggga cca agctggagat caaa                                              324
```

<210> SEQ ID NO 5
<211> LENGTH: 5
<212> TYPE: PRT
<213> ORGANISM: Human

<400> SEQUENCE: 5

Asn Tyr Asp Met Ser
1               5

<210> SEQ ID NO 6
<211> LENGTH: 17
<212> TYPE: PRT
<213> ORGANISM: Human

<400> SEQUENCE: 6

Ser Ile Ser Tyr Ser Gly Gly Ser Thr Tyr Tyr Ala Asp Ser Val Lys
1               5                   10                  15

Gly

<210> SEQ ID NO 7
<211> LENGTH: 12
<212> TYPE: PRT
<213> ORGANISM: Human

<400> SEQUENCE: 7

Arg Ala Ser Gln Ser Val Ser Ser Ser Tyr Leu Ala
1               5                   10

<210> SEQ ID NO 8
<211> LENGTH: 12
<212> TYPE: PRT
<213> ORGANISM: Human

<400> SEQUENCE: 8

Arg Ala Ser Gln Ser Val Ser Ser Ser Tyr Leu Ala
1               5                   10

<210> SEQ ID NO 9
<211> LENGTH: 7
<212> TYPE: PRT
<213> ORGANISM: Human

<400> SEQUENCE: 9

Gly Ala Ser Ser Arg Ala Thr
1               5

<210> SEQ ID NO 10
<211> LENGTH: 9
<212> TYPE: PRT
<213> ORGANISM: Human

<400> SEQUENCE: 10

Gln Gln Tyr Gly Ser Ser Pro Tyr Thr
1               5

<210> SEQ ID NO 11
<211> LENGTH: 15
<212> TYPE: DNA
<213> ORGANISM: Human

<400> SEQUENCE: 11
aactatgaca tgagc 15

<210> SEQ ID NO 12
<211> LENGTH: 51
<212> TYPE: DNA
<213> ORGANISM: Human

<400> SEQUENCE: 12
agtattagtt atagtggtgg tagcacatac tacgcagact ccgtgaaggg c        51

<210> SEQ ID NO 13
<211> LENGTH: 24
<212> TYPE: DNA
<213> ORGANISM: Human

<400> SEQUENCE: 13
aggggggcta ccccatttga ctac                                       24

<210> SEQ ID NO 14
<211> LENGTH: 36
<212> TYPE: DNA
<213> ORGANISM: Human

<400> SEQUENCE: 14
agggccagtc agagtgttag cagcagttac ttagcc                          36

<210> SEQ ID NO 15
<211> LENGTH: 21
<212> TYPE: DNA
<213> ORGANISM: Human

<400> SEQUENCE: 15
ggtgcatcca gcagggccac t                                          21

<210> SEQ ID NO 16
<211> LENGTH: 27
<212> TYPE: DNA
<213> ORGANISM: Human

<400> SEQUENCE: 16
cagcagtatg gtagctcacc gtacact                                    27

<210> SEQ ID NO 17
<211> LENGTH: 98
<212> TYPE: PRT
<213> ORGANISM: Human

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 18
<211> LENGTH: 19
<212> TYPE: PRT
<213> ORGANISM: Human

<400> SEQUENCE: 18

Arg Gly Ala Thr Pro Phe Asp Tyr Trp Gly Gln Gly Thr Leu Val Thr
1               5                   10                  15

Val Ser Ser

<210> SEQ ID NO 19
<211> LENGTH: 96
<212> TYPE: PRT
<213> ORGANISM: Human

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 20
<211> LENGTH: 12
<212> TYPE: PRT
<213> ORGANISM: Human

<400> SEQUENCE: 20

Tyr Thr Phe Gly Gln Gly Thr Lys Leu Glu Ile Lys
1               5                   10

<210> SEQ ID NO 21
<211> LENGTH: 116
<212> TYPE: PRT
<213> ORGANISM: Human

<400> SEQUENCE: 21

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
                20                  25                  30

Ser Lys Val Lys Asp Ala Leu Lys Leu Leu Tyr Ser Gly Val Pro Phe
            35                  40                  45

Leu Gly Pro Tyr His Lys Glu Ser Ala Val Thr Ala Phe Ser Glu Gly
        50                  55                  60

Ser Val Ile Ala Tyr Tyr Trp Ser Glu Phe Ser Ile Pro Gln His Leu
65                  70                  75                  80

Val Glu Glu Ala Glu Arg Val Met Ala Glu Glu Arg Val Val Met Leu
                85                  90                  95

Pro Pro Arg Ala Arg Ser Leu Lys Ser Phe Val Val Thr Ser Val Val
                100                 105                 110

Ala Phe Pro Thr
        115

<210> SEQ ID NO 22
<211> LENGTH: 64
<212> TYPE: PRT
<213> ORGANISM: Human

<400> SEQUENCE: 22

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
            20                  25                  30

Ser Lys Val Lys Asp Ala Leu Lys Leu Leu Tyr Ser Gly Val Pro Phe
        35                  40                  45

Leu Gly Pro Tyr His Lys Glu Ser Ala Val Thr Ala Phe Ser Glu Gly
    50                  55                  60

<210> SEQ ID NO 23
<211> LENGTH: 104
<212> TYPE: PRT
<213> ORGANISM: Human

<400> SEQUENCE: 23

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
            20                  25                  30

Ser Lys Val Lys Asp Ala Leu Lys Leu Leu Tyr Ser Gly Val Pro Phe
        35                  40                  45

Leu Gly Pro Tyr His Lys Glu Ser Ala Val Thr Ala Phe Ser Glu Gly
    50                  55                  60

Ser Val Ile Ala Tyr Tyr Trp Ser Glu Phe Ser Ile Pro Gln His Leu
65                  70                  75                  80

Val Glu Glu Ala Glu Arg Val Met Ala Glu Glu Arg Val Val Met Leu
            85                  90                  95

Pro Pro Arg Ala Arg Ser Leu Lys
            100

<210> SEQ ID NO 24
<211> LENGTH: 119
<212> TYPE: PRT
<213> ORGANISM: Human

<400> SEQUENCE: 24

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
            20                  25                  30

Ser Lys Val Lys Asp Ala Leu Lys Leu Leu Tyr Ser Gly Val Pro Phe
        35                  40                  45

Leu Gly Pro Tyr His Lys Glu Ser Ala Val Thr Ala Phe Ser Glu Gly
    50                  55                  60

Ser Val Ile Ala Tyr Tyr Trp Ser Glu Phe Ser Ile Pro Gln His Leu
65                  70                  75                  80

Val Glu Glu Ala Glu Arg Val Met Ala Glu Glu Arg Val Val Met Leu
            85                  90                  95

```
Pro Pro Arg Ala Arg Ser Leu Lys Ser Phe Val Val Thr Ser Val Val
            100                 105                 110

Ala Phe Pro Thr Asp Ser Lys
        115

<210> SEQ ID NO 25
<211> LENGTH: 241
<212> TYPE: PRT
<213> ORGANISM: Human

<400> SEQUENCE: 25

Val Val Gly Gly Thr Asp Ala Asp Glu Gly Glu Trp Pro Trp Gln Val
1               5                   10                  15

Ser Leu His Ala Leu Gly Gln Gly His Ile Cys Gly Ala Ser Leu Ile
            20                  25                  30

Ser Pro Asn Trp Leu Val Ser Ala Ala His Cys Tyr Ile Asp Asp Arg
        35                  40                  45

Gly Phe Arg Tyr Ser Asp Pro Thr Gln Trp Thr Ala Phe Leu Gly Leu
    50                  55                  60

His Asp Gln Ser Gln Arg Ser Ala Pro Gly Val Gln Glu Arg Arg Leu
65                  70                  75                  80

Lys Arg Ile Ile Ser His Pro Phe Phe Asn Asp Phe Thr Phe Asp Tyr
                85                  90                  95

Asp Ile Ala Leu Leu Glu Leu Glu Lys Pro Ala Glu Tyr Ser Ser Met
            100                 105                 110

Val Arg Pro Ile Cys Leu Pro Asp Ala Ser His Val Phe Pro Ala Gly
            115                 120                 125

Lys Ala Ile Trp Val Thr Gly Trp Gly His Thr Gln Tyr Gly Gly Thr
    130                 135                 140

Gly Ala Leu Ile Leu Gln Lys Gly Glu Ile Arg Val Ile Asn Gln Thr
145                 150                 155                 160

Thr Cys Glu Asn Leu Leu Pro Gln Gln Ile Thr Pro Arg Met Met Cys
                165                 170                 175

Val Gly Phe Leu Ser Gly Gly Val Asp Ser Cys Gln Gly Asp Ser Gly
            180                 185                 190

Gly Pro Leu Ser Ser Val Glu Ala Asp Gly Arg Ile Phe Gln Ala Gly
        195                 200                 205

Val Val Ser Trp Gly Asp Gly Cys Ala Gln Arg Asn Lys Pro Gly Val
    210                 215                 220

Tyr Thr Arg Leu Pro Leu Phe Arg Asp Trp Ile Lys Glu Asn Thr Gly
225                 230                 235                 240

Val

<210> SEQ ID NO 26
<211> LENGTH: 853
<212> TYPE: PRT
<213> ORGANISM: Human

<400> SEQUENCE: 26

Met Gly Ser Asp Arg Ala Arg Lys Gly Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
```

```
                50                  55                  60
Leu Leu Leu Val Leu Leu Gly Ile Gly Phe Leu Val Trp His Leu Gln
 65                  70                  75                  80

Tyr Arg Asp Val Arg Val Gln Lys Val Phe Asn Gly Tyr Met Arg Ile
                     85                  90                  95

Thr Asn Glu Asn Phe Val Asp Ala Tyr Glu Asn Ser Asn Ser Thr Glu
                100                 105                 110

Phe Val Ser Leu Ala Ser Lys Val Lys Asp Ala Leu Lys Leu Leu Tyr
                115                 120                 125

Ser Gly Val Pro Phe Leu Gly Pro Tyr His Lys Glu Ser Ala Val Thr
            130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
                180                 185                 190

Val Thr Ser Val Val Ala Phe Pro Thr Asp Ser Lys Thr Val Gln Arg
            195                 200                 205

Thr Gln Asp Asn Ser Cys Ser Phe Gly Leu His Ala Arg Gly Val Glu
            210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
                260                 265                 270

Ser Asp Leu Val Thr Val Tyr Asn Thr Leu Ser Pro Met Glu Pro His
            275                 280                 285

Ala Leu Val Gln Leu Cys Gly Thr Tyr Pro Pro Ser Tyr Asn Leu Thr
            290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
                340                 345                 350

Ser Pro Tyr Tyr Pro Gly His Tyr Pro Pro Asn Ile Asp Cys Thr Trp
                355                 360                 365

Asn Ile Glu Val Pro Asn Asn Gln His Val Lys Val Arg Phe Lys Phe
370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
                420                 425                 430

Gln Ser Tyr Thr Asp Thr Gly Phe Leu Ala Glu Tyr Leu Ser Tyr Asp
            435                 440                 445

Ser Ser Asp Pro Cys Pro Gly Gln Phe Thr Cys Arg Thr Gly Arg Cys
            450                 455                 460

Ile Arg Lys Glu Leu Arg Cys Asp Gly Trp Ala Asp Cys Thr Asp His
465                 470                 475                 480
```

```
Ser Asp Glu Leu Asn Cys Ser Cys Asp Ala Gly His Gln Phe Thr Cys
                485                 490                 495

Lys Asn Lys Phe Cys Lys Pro Leu Phe Trp Val Cys Asp Ser Val Asn
            500                 505                 510

Asp Cys Gly Asp Asn Ser Asp Glu Gln Gly Cys Ser Cys Pro Ala Gln
        515                 520                 525

Thr Phe Arg Cys Ser Asn Gly Lys Cys Leu Ser Lys Ser Gln Gln Cys
    530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
        595                 600                 605

Phe Thr Arg Gln Ala Arg Val Val Gly Gly Thr Asp Ala Asp Glu Gly
    610                 615                 620

Glu Trp Pro Trp Gln Val Ser Leu His Ala Gln Gly His Ile Cys Gly
625                 630                 635                 640

Ala Ser Leu Ile Ser Pro Asn Trp Leu Val Ser Ala Ala His Cys Tyr
                645                 650                 655

Ile Asp Asp Arg Gly Phe Arg Tyr Ser Asp Pro Thr Gln Trp Thr Ala
            660                 665                 670

Phe Leu Gly Leu His Asp Gln Ser Gln Arg Ser Ala Pro Gly Val Gln
        675                 680                 685

Glu Arg Arg Leu Lys Arg Ile Ile Ser His Pro Phe Phe Asn Asp Phe
    690                 695                 700

Thr Phe Asp Tyr Asp Ile Ala Leu Leu Glu Leu Glu Lys Pro Ala Glu
705                 710                 715                 720

Tyr Ser Ser Met Val Arg Pro Ile Cys Leu Pro Asp Ala Ser His Val
                725                 730                 735

Phe Pro Ala Gly Lys Ala Ile Trp Val Thr Gly Trp Gly His Thr Gln
            740                 745                 750

Tyr Gly Gly Thr Gly Ala Leu Ile Leu Gln Lys Gly Glu Ile Arg Val
        755                 760                 765

Ile Asn Gln Thr Thr Cys Glu Asn Leu Leu Pro Gln Gln Ile Thr Pro
    770                 775                 780

Arg Met Met Cys Val Gly Phe Leu Ser Gly Gly Val Asp Ser Cys Gln
785                 790                 795                 800

Gly Asp Ser Gly Gly Pro Leu Ser Ser Val Glu Ala Asp Gly Arg Ile
                805                 810                 815

Phe Gln Ala Gly Val Val Ser Trp Gly Asp Gly Cys Ala Gln Arg Asn
            820                 825                 830

Lys Pro Gly Val Tyr Thr Arg Leu Pro Leu Phe Arg Asp Trp Ile Lys
        835                 840                 845

Glu Asn Thr Gly Val
    850

<210> SEQ ID NO 27
<211> LENGTH: 241
<212> TYPE: PRT
<213> ORGANISM: Human
```

```
<400> SEQUENCE: 27

Val Val Gly Gly Thr Asp Ala Asp Glu Gly Glu Trp Pro Trp Gln Val
1               5                   10                  15

Ser Leu His Ala Leu Gly Gln Gly His Ile Cys Gly Ala Ser Leu Ile
            20                  25                  30

Ser Pro Asn Trp Leu Val Ser Ala His Cys Tyr Ile Asp Asp Arg
        35                  40                  45

Gly Phe Arg Tyr Ser Asp Pro Thr Gln Trp Thr Ala Phe Leu Gly Leu
    50                  55                  60

His Asp Gln Ser Gln Arg Ser Ala Pro Gly Val Gln Glu Arg Arg Leu
65                  70                  75                  80

Lys Arg Ile Ile Ser His Pro Phe Phe Asn Asp Phe Thr Phe Asp Tyr
                85                  90                  95

Asp Ile Ala Leu Leu Glu Leu Glu Lys Pro Ala Glu Tyr Ser Ser Met
            100                 105                 110

Val Arg Pro Ile Cys Leu Pro Asp Ala Ser His Val Phe Pro Ala Gly
            115                 120                 125

Lys Ala Ile Trp Val Thr Gly Trp Gly His Thr Gln Tyr Gly Gly Thr
        130                 135                 140

Gly Ala Leu Ile Leu Gln Lys Gly Glu Ile Arg Val Ile Asn Gln Thr
145                 150                 155                 160

Thr Cys Glu Asn Leu Leu Pro Gln Gln Ile Thr Pro Arg Met Met Cys
                165                 170                 175

Val Gly Phe Leu Ser Gly Gly Val Asp Ser Cys Gln Gly Asp Ser Gly
            180                 185                 190

Gly Pro Leu Ser Ser Val Glu Ala Asp Gly Arg Ile Phe Gln Ala Gly
        195                 200                 205

Val Val Ser Trp Gly Asp Gly Cys Ala Gln Arg Asn Lys Pro Gly Val
    210                 215                 220

Tyr Thr Arg Leu Pro Leu Phe Arg Asp Trp Ile Lys Glu Asn Thr Gly
225                 230                 235                 240

Val

<210> SEQ ID NO 28
<211> LENGTH: 359
<212> TYPE: PRT
<213> ORGANISM: Human

<400> SEQUENCE: 28

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
            20                  25                  30

Ser Lys Val Lys Asp Ala Leu Lys Leu Leu Tyr Ser Gly Val Pro Phe
        35                  40                  45

Leu Gly Pro Tyr His Lys Glu Ser Ala Val Thr Ala Phe Ser Glu Gly
    50                  55                  60

Ser Val Ile Ala Tyr Tyr Trp Ser Glu Phe Ser Ile Pro Gln His Leu
65                  70                  75                  80

Val Glu Glu Ala Glu Arg Val Met Ala Glu Glu Arg Val Val Met Leu
                85                  90                  95

Pro Pro Arg Ala Arg Ser Leu Lys Ser Phe Val Val Thr Ser Val Val
            100                 105                 110

Ala Phe Pro Thr Ala Ser Gly Ser Gly Ile Glu Gly Arg Gly Leu Glu
```

```
              115                 120                 125
Pro Lys Ser Ser Asp Lys Thr His Thr Cys Pro Pro Cys Pro Ala Pro
130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355

<210> SEQ ID NO 29
<211> LENGTH: 30
<212> TYPE: PRT
<213> ORGANISM: Human

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg
            20                  25                  30

<210> SEQ ID NO 30
<211> LENGTH: 14
<212> TYPE: PRT
<213> ORGANISM: Human

<400> SEQUENCE: 30

Trp Val Arg Gln Ala Pro Gly Lys Gly Leu Glu Trp Val Ser
1               5                   10

<210> SEQ ID NO 31
<211> LENGTH: 32
<212> TYPE: PRT
<213> ORGANISM: Human

<400> SEQUENCE: 31
```

```
Arg Phe Thr Ile Ser Arg Asp Asn Ser Lys Asn Thr Leu Ser Leu Gln
1               5                   10                  15

Met Asn Ser Leu Arg Ala Glu Asp Thr Ala Val Tyr Tyr Cys Ala Lys
            20                  25                  30

<210> SEQ ID NO 32
<211> LENGTH: 11
<212> TYPE: PRT
<213> ORGANISM: Human

<400> SEQUENCE: 32

Trp Gly Gln Gly Ser Leu Val Thr Val Ser Ser
1               5                   10

<210> SEQ ID NO 33
<211> LENGTH: 23
<212> TYPE: PRT
<213> ORGANISM: Human

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 34
<211> LENGTH: 15
<212> TYPE: PRT
<213> ORGANISM: Human

<400> SEQUENCE: 34

Trp Tyr Gln Gln Lys Pro Gly Gln Ala Pro Arg Leu Leu Ile Tyr
1               5                   10                  15

<210> SEQ ID NO 35
<211> LENGTH: 32
<212> TYPE: PRT
<213> ORGANISM: Human

<400> SEQUENCE: 35

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 36
<211> LENGTH: 10
<212> TYPE: PRT
<213> ORGANISM: Human

<400> SEQUENCE: 36

Phe Gly Gln Gly Thr Lys Leu Glu Ile Lys
1               5                   10
```

ANTIBODIES

CROSS REFERENCE TO RELATED APPLICATIONS

This application is a 35 U.S.C. 371 national stage filing of International Application No. PCT/GB2014/053470, filed on Nov. 25, 2014, which claims priority from U.S. Provisional Application No. 61/908,371, filed on Nov. 25, 2013. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on May 11, 2016, is named OTJ_009US_Sequence.txt and is 27,712 bytes in size.

BACKGROUND

Matriptase degrades extracellular matrix. According to SWISS-PROT, it is proposed to play a role in breast cancer invasion and metastasis. It exhibits trypsin-like activity as defined by cleavage of synthetic substrates with Arg or Lys as the P1 site. It has an essential physiological role in profilaggrin processing, corneocyte maturation and lipid matrix formation associated with terminal differentiation of the oral epithelium and the epidermis and is also critical for hair follicle growth. It is a type II transmembrane serine protease expressed in most human epithelia and it is a strictly epithelial protease. It is expressed in carcinomas of epithelial origin and not in tumours of mesenchymal origin. Matriptase has previously been described in WO2009/020645.

BRIEF SUMMARY OF THE INVENTION

The present disclosure provides antibodies directed against Matriptase (e.g., against human Matriptase comprising SEQ ID NO:26 or a functional fraction, such as the stem (SEQ ID No: 21-24) and related compositions, including nucleic acids encoding the antibodies and therapeutic proteins, and host cells comprising such nucleic acids. The invention further provides methods for preparing anti-Matriptase antibodies and methods of using the antibodies to treat diseases, such as the Matriptase mediated disorders, e.g. human cancers, including gastric cancer, colorectal cancer, prostate cancer, breast cancer, ovarian cancer, lung cancer, preferably SCLC, esophageal cancer, head and neck cancer, pancreatic cancer, lymphoma preferably non-Hodgkin's lymphoma and skin cancer.

In a particular embodiment, the anti-Matriptase antibody (or antigen binding fragment thereof) of the invention binds to the extracellular stem region of Matriptase (SEQ ID NO: 21-24) and is internalized by a cell expressing Matriptase.

In one aspect, the invention provides an antibody, or an antigen-binding portion thereof, which: (a) binds an epitope on Matriptase which is recognized by an antibody comprising a heavy chain variable region comprising the amino acid sequence set forth in SEQ ID NO: 1 and a light chain variable region comprising the amino acid sequence set forth in SEQ ID NO: 2, or (b) competes for binding to LY75 with an antibody comprising a heavy chain variable region comprising the amino acid sequence set forth in SEQ ID NO: 1, and a light chain variable region comprising the amino acid sequence set forth in SEQ ID NO: 2.

In one embodiment, the antibody or antigen-binding portion thereof binds to human LY75 and comprises a heavy chain variable region comprising 1, 2 or 3 CDRs selected from the group consisting of CDRs comprising SEQ ID NOs: 5, 6, and 7, and/or a light chain variable region comprising 1, 2 or 3 CDRs selected from the group consisting of CDRs comprising SEQ ID NOs: 8, 9 and 10.

In another embodiment, the antibody comprises the heavy and light chain complementarity determining regions (CDRs) or variable regions (VRs) of the particular antibodies described herein (e.g., referred to herein as "Matriptase_A1"). Accordingly, in one embodiment, the antibody comprises the CDR1, CDR2, and CDR3 domains of the heavy chain variable (VH) region of Matriptase_A1 having the sequence shown in SEQ ID NO:1, and/or the CDR1, CDR2 and CDR3 domains of the light chain variable (VL) region of A1 having the sequence shown in SEQ ID NO:2.

In another embodiment, the antibody comprises a heavy chain variable region comprising a first vhCDR comprising SEQ ID NO: 5; a second vhCDR comprising SEQ ID NO: 6; and a third vhCDR comprising SEQ ID NO:7; and/or a light chain variable region comprising a first vlCDR comprising SEQ ID NO:8; a second vlCDR comprising SEQ ID NO: 9; and a third vlCDR comprising SEQ ID NO:10.

In another embodiment, the antibodies of the invention bind to human Matriptase and include a heavy chain variable region including an amino acid sequence SEQ ID NO:1, and conservative sequence modifications thereof. The antibody may further include a light chain variable region including an amino acid sequence SEQ ID NO:2, and conservative sequence modifications thereof.

In a further embodiment, the antibodies of the invention bind to human Matriptase and include a heavy chain variable region and a light chain variable region including the amino acid sequences set forth in SEQ ID NOs:1 and/or 2, respectively, and conservative sequence modifications thereof.

In will be understood that the conservative sequence modifications can be amino acid substitutions, additions or deletions, but are preferably substitutions. As used herein, the term conservative sequence modification refers to, for example, the substitution of an amino acid with an amino acid having similar characteristics. It is common general knowledge for one skilled in the art what such substitutions may be considered conservative. Other modifications which can be considered to be conservative sequence modifications include, for example, glycosylation.

It will be further understood that the conservative sequence modifications may be present in one or more of the CDR regions (SEQ ID NOs: 5-10) and/or one or more of the framework regions (SEQ ID NOs: 29-36) of the heavy and/or light chain variable regions set forth in SEQ ID NOs: 1 and/or 2.

In preferred embodiments said antibodies are isolated antibodies.

Isolated antibodies which include heavy and light chain variable regions having at least 80%, or at least 85%, or at least 90%, or at least 91%, or at least 92%, or at least 93%, or at least 94%, or at least 95%, or at least 96%, or at least 97%, or at least 98%, or at least 99%, or more sequence identity to any of the above sequences are also included in the present invention. Ranges intermediate to the above-recited values, e.g., heavy and light chain variable regions having at least 80-85%, 85-90%, 90-95% or 95-100% sequence identity to any of the above sequences are also intended to be encompassed by the present invention. In one embodiment, the antibody comprises a heavy chain variable region comprising SEQ ID NO:1, or a sequence that is at least 90%, at least 91%, at least 92%, at least 93%, at least 94%, at least 95%, at least 96%, at least 97%, at least 98%, at least 99% identical to SEQ ID NO: 1. In another embodiment, the antibody comprises a light chain variable region comprising SEQ ID NO:2 or a sequence that is at least 90%, at least 91%, at least 92%, at least 93%, at least 94%, at least 95%, at least 96%, at least 97%, at least 98%, at least 99% identical to SEQ ID NO: 2. In another embodiment, the antibody comprises a heavy chain framework region comprising an amino acid sequence that is at least 90%, at least 91%, at least 92%, at least 93%, at least 94%, at least 95%, at least 96%, at least 97%, at least 98%, at least 99% identical to the framework of the heavy chain variable region of SEQ ID NO: 1 as shown in SEQ ID NOs 29, 30, 31 and 32. In another embodiment, the antibody comprises a light chain framework region comprising an amino acid sequence that is at least 90%, at least 91%, at least 92%, at least 93%, at least 94%, at least 95%, at least 96%, at least 97%, at least 98%, at least 99% identical to the framework of the light chain variable region of SEQ ID NO:2, as shown in SEQ ID NOs: 33, 34, 35, and 36.

Also encompassed by the present invention are isolated antibodies which compete for binding to Matripitase with the antibodies of the invention. In a particular embodiment, the antibody competes for binding to Matripitase with an antibody comprising heavy and/or light chain variable regions comprising the amino acid sequences set forth in SEQ ID NOs:1 and 2, respectively, or amino acid sequences at least 80%, at least 85%, at least 90%, at least 91%, at least 92%, at least 93%, at least 94%, at least 95%, at least 96%, at least 97%, at least 98%, at least 99% identical thereto. In another embodiment, the antibody competes for binding to Matriptase with an antibody comprising heavy and/or light chain variable regions comprising the amino acid sequences set forth in SEQ ID NOs:1 and 2 (A1).

Other antibodies of the invention bind to the same epitope or an epitope on Matriptase recognized by the antibodies described herein. In another particular embodiment, the antibody binds to an epitope on Matriptase recognized by an antibody comprising heavy and/or light chain variable regions comprising the amino acid sequences set forth in SEQ ID NOs:1 and 2, respectively, or amino acid sequences at least 80%, at least 85%, at least 90%, at least 91%, at least 92%, at least 93%, at least 94%, at least 95%, at least 96%, at least 97%, at least 98%, at least 99% identical thereto. In another embodiment, the antibody binds to an epitope on Matriptase recognized by an antibody comprising heavy and/or light chain variable regions comprising the amino acid sequences set forth in SEQ ID NOs:1 and 2 (A1).

In a further embodiment, the antibodies of the invention comprise variable CDRs as compared to the parent antibodies described herein. Thus, the invention provides variant antibodies comprising variant variable regions of a parent antibody, wherein the parent antibody comprises a first vhCDR comprising SEQ ID NO:5, a second vhCDR comprising SEQ ID NO: 6, a third vhCDR comprising SEQ ID NO:7, a first vlCDR comprising SEQ ID NO:8, a second vlCDR comprising SEQ ID NO:9 and a third vlCDR comprising a SEQ ID NO:10, and wherein the variant antibody has 1, 2, 3, 4, 5 or 6 amino acid substitutions collectively in the set of the first vhCDR, the second vhCDR, the third vhCDR, the first vlCDR, the second vlCDR and the third vlCDR, with from 1 to 4, 1 to 3 or 1 to 2 substitutions of particular use, and wherein the antibody retains specific binding to Matriptase.

The antibodies of the invention can either be full-length, for example, any of the following isotypes: IgG1, IgG2, IgG3, IgG4, IgM, IgA1, IgA2, IgAsec, IgD, and IgE. Alternatively, the antibodies can be fragments such as an antigen-binding portion or a single chain antibody (e.g., a Fab, F(ab')$_2$, Fv, a single chain Fv fragment, an isolated complementarity determining region (CDR) or a combination of two or more isolated CDRs). The antibodies can be any kind of antibody, including, but not limited to, human, humanized, and chimeric antibodies.

In other embodiments, the antibodies of the invention are in the form of an immunoconjugate (i.e., further include a covalently attached moiety). In a particular embodiment, the moiety is a drug, such as a maytansinoid, a hemiasterlin, a dolastatin, an auristatin, a trichothecene, a calicheamicin, a CC1065 or derivatives thereof. In a preferred embodiment the drug is an auristatin, more preferably MMAE or MMAF.

In other embodiments, the antibodies of the invention are in the form of a bispecific molecule, for example, which elicits an antibody dependent cellular cytotoxicity (ADCC) response in the presence of effector cells, thus killing Matriptase-expressing cells.

In another aspect, the invention provides nucleic acids encoding heavy and/or light chain variable regions of the foregoing antibodies. In one embodiment, the invention provides an isolated monoclonal antibody that binds human Matriptase, wherein the antibody comprises a heavy chain variable region and a light chain variable region encoded by nucleic acid sequences comprising SEQ ID NOs:3 and 4, respectively, or nucleic acid sequences having at least 85%, 86%, 87%, 88%, 89%, 90%, 91%, 92%, 93%, 94%, 95%, 96%, 97%, 98% or 99% identity to the aforementioned nucleic acid sequences or sequences which differ from SEQ ID NOs: 3 and 4 due to degeneracy of the genetic code.

In another aspect of the present invention there are provided expression vectors comprising nucleic acids encoding heavy and/or light chain variable regions of the antibodies of the invention operably linked to one or more regulatory elements.

In another aspect, the invention provides host cells containing nucleic acids encoding heavy and/or light chain variable regions or the antigen binding portions thereof of the foregoing antibodies. Preferably, wherein the host cell expresses said heavy and/or light chain variable regions or the antigen binding portions thereof when the host cell is grown under condition wherein the nucleic acid(s) is expressed. In other embodiments, a method of recovering one or more antibodies of the invention are provided. In a preferred embodiment the host cell comprises: (i) an expression vector according to the present invention; or
(ii) a first expression vector comprising the nucleic acid sequence encoding the heavy chain of the antibody of the invention or the antigen-binding portion thereof and a second expression vector comprising the nucleic acid sequence encoding the light chain of the antibody of the invention or the antigen-binding portion thereof.

In a further aspect of the present invention there is provided of making an antibody or an antigen-binding portion thereof, comprising culturing a host cell according to the present invention under conditions where the antibody or an antigen-binding portion thereof is expressed and optionally isolating the antibody or an antigen-binding portion thereof.

In still another aspect, the invention provides a method of treating cancer, wherein a patient in need thereof is administered an antibody or antibodies, or binding portions thereof of the invention. In a particular embodiment, the patient is administered an antibody which binds to the extracellular stem region of Matriptase (SEQ ID NO:21-24). In another embodiment, the antibody or antibodies of the invention are internalized. In one embodiment the antibody or antigen binding portion comprises a covalently attached drug moiety. In another embodiment, the antibody comprises a heavy chain variable region comprising a first vhCDR comprising SEQ ID NO: 5; a second vh CDR comprising SEQ ID NO: 6; and a third vhCDR comprising SEQ ID NO: 7 and a light chain variable region comprising a first vlCDR comprising Seq ID NO: 8, a second vlCDR comprising SEQ ID NO: 9 and a third vlCDR comprising SEQ ID NO: 10.

In a further aspect, there is provided a method of treating cancer, wherein a patient in need thereof is adminstered an antibody or antibodies or an antigen-binding portion thereof of the invention and wherein such antibody or antibodies or an antigen-binding portion thereof of the invention elicit an ADCC response in the presence of effector cells. Preferably, the antibody or an antigen-binding portion thereof comprises a heavy chain variable region comprising a first vhCDR comprising SEQ ID NO: 5; a second vhCDR comprising SEQ ID NO: 6; and a third vhCDR comprising SEQ ID NO: 7; and a light chain variable region comprising a first vlCDR comprising SEQ ID NO: 8; a second vlCDR comprising SEQ ID NO: 9; and a third vlCDR comprising SEQ ID NO: 10.

In a further aspect there is provided a method of treating cancer, wherein a patient in need thereof is adminstered an antibody or antibodies or an antigen-binding portion thereof of the invention and wherein such antibody or antibodies or an antigen-binding portion thereof of the invention elicit a cytotoxic T-cell response in the presence of effector cells. Preferably, the antibody comprises a heavy chain variable region comprising a first vhCDR comprising SEQ ID NO: 5; a second vhCDR comprising SEQ ID NO: 6; and a third vhCDR comprising SEQ ID NO: 7; and a light chain variable region comprising a first vlCDR comprising SEQ ID NO: 8; a second vlCDR comprising SEQ ID NO: 9; and a third vlCDR comprising SEQ ID NO: 10.

In a further aspect of the present invention there is provided one or more antibodies of the invention for use in the treatment of cancer.

Also provided is the use of one or more antibodies of the invention in the manufacture of a medicament for the treatment of cancer.

In one embodiment, the cancer is selected from the group of gastric cancer, colorectal cancer, prostate cancer, breast cancer, ovarian cancer lung cancer, preferably SCLC, esophageal cancer, head and neck cancer, pancreatic cancer, lymphoma preferably non-Hodgkin's lymphoma and skin cancer.

According to a still further aspect of the invention there is provided method of detecting, diagnosing and/or screening for or monitoring the progression of a cancer wherein Matriptase is expressed in said cancer, or of monitoring the effect of a cancer drug or therapy directed to said cancer, in a subject which comprises detecting the presence or level of antibodies capable of immunospecific binding to Matriptase, or one or more fragments thereof.

Preferably the cancer is selected from the group of gastric cancer, colorectal cancer, prostate cancer, breast cancer, ovarian cancer lung cancer, preferably SCLC, esophageal cancer, head and neck cancer, pancreatic cancer, lymphoma preferably non-Hodgkin's lymphoma and skin cancer.

Also within the scope of the invention are kits comprising the compositions (e.g., antibodies) of the invention and, optionally, instructions for use. The kit can further contain a least one additional reagent or one or more additional antibodies of the invention.

Other features and advantages of the instant invention will be apparent from the following detailed description and claims.

BRIEF DESCRIPTION OF THE DRAWINGS

FIGS. 1a and 1b depict cleavage sites of Matriptase resulting in the stem regions (SEQ ID Nos: 21-24).

FIG. 2a depicts the alignment of Matriptase_A1 heavy chain, the human VH 3-23 Germline and the human JH4b Germline. The CDR regions of Matriptase_A1 heavy chain are underlined.

FIG. 2b depicts the alignment of Matriptase_A1 light chain, the human VK A27 Germline and the human JK2 Germline. The CDR regions of Matriptase_A1 light chain are underlined.

DETAILED DESCRIPTION OF THE INVENTION

In one embodiment, the present disclosure relates to isolated antibodies which bind specifically to the stem region of Matriptase described in SEQ ID No: 21-24 with high affinity, as outlined herein.

In particular embodiments, the Matriptase antibodies of the present invention may be in the form of a bispecific molecule, for example, which enhances an antibody dependent cellular cytotoxicity (ADCC) response in the presence of effector cells, thus killing Matriptase-expressing cells.

In other embodiments, the Matriptase antibodies of the present invention are internalized when contacted with cells expressing the Matriptase receptor. As discussed herein, the Matriptase receptor is overexpressed and/or differentially expressed on certain cancer cells, including but not limited to, tumors of gastric cancer, colorectal cancer, prostate cancer, breast cancer, ovarian cancer lung cancer, preferably SCLC, esophageal cancer, head and neck cancer, pancreatic cancer, lymphoma preferably non-Hodgkin's lymphoma and skin cancer.

Accordingly, when such Matriptase antibodies of the present invention are conjugated to drugs (sometimes referred to herein as "antibody-drug conjugates" or "ADCs"), the internalization of these ADC molecules into cancer cells results in cell death and thus tumor treatment.

Thus, the disclosure provides antibodies particularly isolated antibodies (which, as outlined below, includes a wide variety of well known antibody structures, derivatives, mimetics and conjugates), nucleic acids encoding these antibodies, host cells used to make the antibodies, methods of making the antibodies, and pharmaceutical compositions comprising the antibodies and optionally including a pharmaceutical carrier.

Matriptase Proteins

Figure 1A:
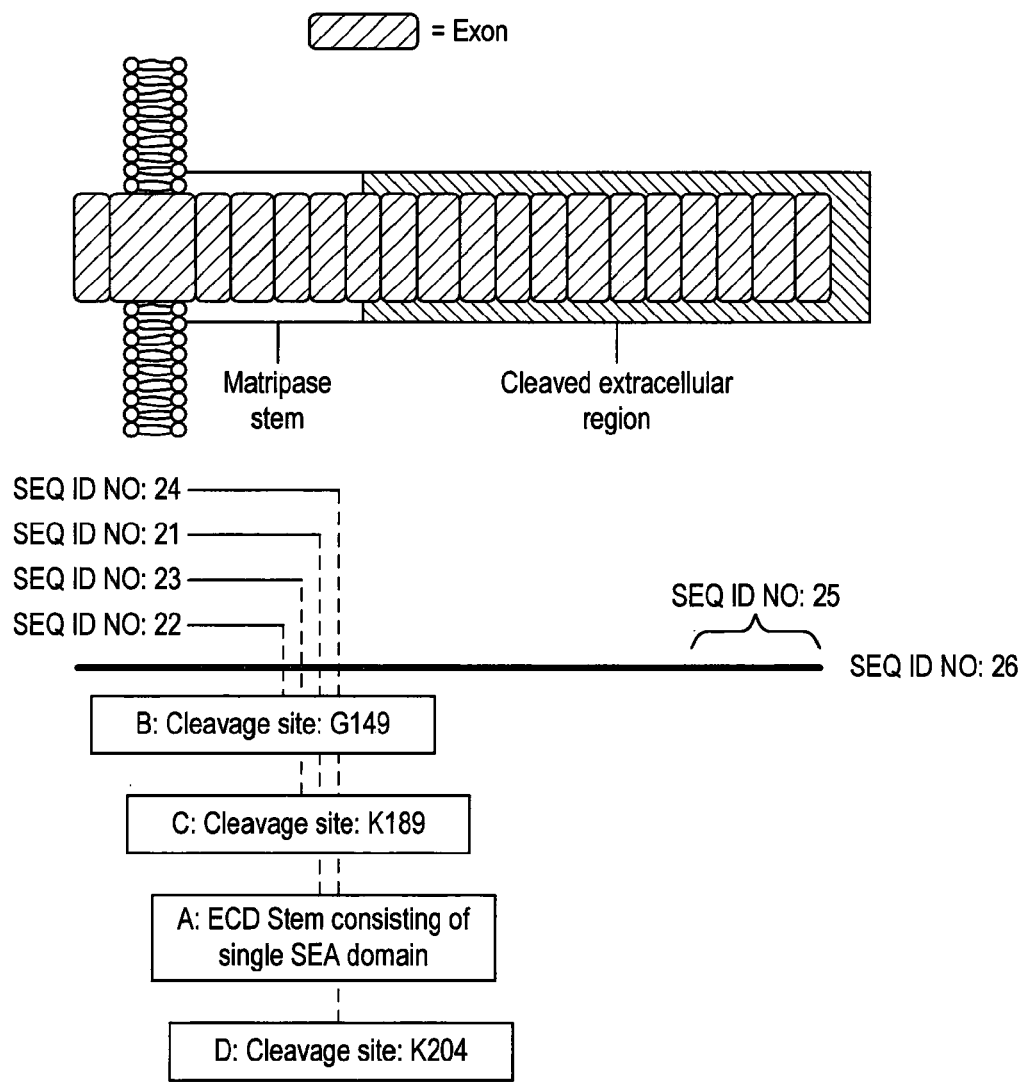

The extracellular stem region of Matriptase has been reported to consist of a single SEA domain comprising amino acid residues 86-201 (SEQ ID No: 21). Activation of Matriptase requires sequential endoproteolytic cleavages and activation site autocleavage. Cleavage occurs after amino acid Gly149, resulting in a stem region comprising amino acid residues 86-149 (Matriptase Stem Sequence B, SEQ ID No: 22). Further proteolytic cleavage can occur after amino acid K189, which results in a stem region comprising amino acid sequences 86-189 (Matriptase Stem Sequence C, SEQ ID No: 23) or amino acid K204, which results in a stem region comprising amino acid sequences 86-204 (Matriptase Stem Sequence D, SEQ ID No: 24). Matriptase is then converted into its active conformation by proteolytic cleavage after Arg614. The catalytic C-terminal serine protease domain consists of amino acid residues 615-855 (SEQ ID No: 27) (FIG. 1). See, for example, Matriptase: Potent Proteolysis on the Cell Surface; List, Bugge and Szabo; Mol Med 12(1-3)1-7, January-March 2006 and Regulation of the activity of Matriptase on epithelial cell surfaces by a blood derived factor; Benaud, Dickson and Lin; Eur J Biochem 268, 1439-1447, 2001 which are herein incorporated in their entirety.

Accordingly, the present invention provides isolated anti-Matriptase antibodies that specifically bind the stem region of human Matriptase. By "human Matriptase" or "human Matriptase antigen" refers to the protein of SEQ ID NO:26 or a functional fraction such as the stem (SEQ ID No: 21-24), as defined herein. In general, Matriptase possesses a short intracytoplasmic tail, a transmembrane domain, and an extracellular domain which when cleaved produces the Matriptase stem region. In specific embodiments, the antibodies of the invention bind to the stem region of the Matriptase protein.

The antibodies of the invention may, in certain cases, cross-react with the Matriptase from species other than human. For example, to facilitate clinical testing, the antibodies of the invention may cross react with murine or primate Matriptase molecules. Alternatively, in certain embodiments, the antibodies may be completely specific for one or more human Matriptase and may not exhibit species or other types of non-human cross-reactivity.

Antibodies

The present invention provides anti-Matriptase antibodies, generally therapeutic and/or diagnostic antibodies as described herein. Antibodies that find use in the present invention can take on a number of formats as described herein, including traditional antibodies as well as antibody derivatives, fragments and mimetics, described below.

Essentially, the invention provides antibody structures that contain a set of 6 CDRs as defined herein (including small numbers of amino acid changes as described below).

"Antibody" as used herein includes a wide variety of structures, as will be appreciated by those in the art, that at a minimum contain a set of 6 CDRs as defined herein; including, but not limited to traditional antibodies (including both monoclonal and polyclonal antibodies), humanized and/or chimeric antibodies, antibody fragments, engineered antibodies (e.g. with amino acid modifications as outlined below), multispecific antibodies (including bispecific antibodies), and other analogs known in the art and discussed herein.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. It should be understood that therapeutic antibodies can also comprise hybrids of any combination of isotypes and/or subclasses.

In many embodiments, IgG isotypes are used in the present invention, with IgG1 finding particular use in a number of applications.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96

(LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)).

The CDRs contribute to the formation of the antigen-binding, or more specifically, epitope binding site of antibodies. The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from Matriptase are tested for reactivity with the given anti-Matriptase antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)). The term "epitope mapping" refers to the process of identification of the molecular determinants for antibody-antigen recognition "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope. In the present invention, the exact epitope is not determinative; rather, the ability of the antibodies of the invention to bind to the Matriptase receptor and be internalized or elicit an ADCC response in the presence of effector cells is important.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Of particular interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Structures that rely on the use of a set of CDRs are included within the definition of "antibody".

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference).

Chimeric and Humanized Antibodies

In some embodiments, the antibody can be a mixture from different species, e.g. a chimeric antibody and/or a humanized antibody. That is, in the present invention, the CDR sets can be used with framework and constant regions other than those specifically described by sequence herein.

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

In one embodiment, the antibodies of the invention can be multispecific antibodies, and notably bispecific antibodies, also sometimes referred to as "diabodies". These are antibodies that bind to two (or more) different antigens, or different epitopes on the same antigen. Diabodies can be manufactured in a variety of ways known in the art (Holliger and Winter, 1993, Current Opinion Biotechnol. 4:446-449, entirely incorporated by reference), e.g., prepared chemically or from hybrid hybridomas.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region. It should be noted that minibodies are included within the definition of "antibody" despite the fact it does not have a full set of CDRs.

The antibodies of the present invention are generally isolated or recombinant. "Isolated," when used to describe the various polypeptides disclosed herein, means a polypeptide that has been identified and separated and/or recovered from a cell or cell culture from which it was expressed. Thus an isolated antibody is intended to refer to an antibody that is substantially free of other antibodies having different antigenic specificities (e.g. an isolated antibody that specifically binds to the Matriptase is substantially free of antibodies that specifically bind antigens other than the Matriptase). Thus, an "isolated" antibody is one found in a form not normally found in nature (e.g. non-naturally occurring).

In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced. Ordinarily, an isolated polypeptide will be prepared by at least one purification step. An "isolated antibody," refers to an antibody which is substantially free of other antibodies having different antigenic specificities. For instance, an isolated antibody that specifically binds to Matriptase is substantially free of antibodies that specifically bind antigens other than Matriptase.

Isolated monoclonal antibodies, having different specificities, can be combined in a well defined composition. Thus for example, the antibody of the invention can optionally and individually be included or excluded in a formulation, as is further discussed below.

The anti-Matriptase antibodies of the present invention specifically bind Matriptase (e.g. Matriptase-stem (SEQ ID Nos: 21-24)). "Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a $K_D$ for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where $K_D$ refers to a dissociation rate of a particular antibody-antigen interaction. Typically, an antibody that specifically binds an antigen will have a $K_D$ that is 20-, 50-, 100-, 500-, 1000-, 5,000-, 10,000- or more times greater for a control molecule relative to the antigen or epitope. However, in the present invention, when administering ADCs of the Matriptase antibodies of the invention, what is important is that the KD is sufficient to allow internalization and thus cell death without significant side effects.

Also, specific binding for a particular antigen or an epitope can be exhibited, for example, by an antibody having a $K_A$ or $K_a$ for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

Standard assays to evaluate the binding ability of the antibodies toward Matriptase can be done on the protein or cellular level and are known in the art, including for example, ELISAs, Western blots, RIAs, BIAcore® assays and flow cytometry analysis. Suitable assays are described in detail in the Examples. The binding kinetics (e.g. binding affinity) of the antibodies also can be assessed by standard assays known in the art, such as by Biacore® system analysis. To assess binding to Raji or Daudi B cell tumor cells, Raji (ATCC Deposit No. CCL-86) or Daudi (ATCC Deposit No. CCL-213) cells can be obtained from publicly available sources, such as the American Type Culture Collection, and used in standard assays, such as flow cytometric analysis.

Matriptase Antibodies

The present invention provides Matriptase antibodies that specifically bind the stem of human Matriptase (SEQ ID No: 21-24) and are internalized when contacted with cells expressing Matriptase on the cell surface. These antibodies are referred to herein either as "anti-Matriptase" antibodies or, for ease of description, "Matriptase antibodies".

The Matriptase antibodies maybe internalized upon contact with cells, particularly tumor cells that express Matriptase on the surface. Accordingly, Matriptase antibodies as defined herein that also comprise drug conjugates are internalized by tumor cells, resulting in the release of the drug and subsequent cell death, allowing for treatment of cancers that exhibit Matriptase expression. Internalization in this context can be measured in several ways. In one embodiment, the Matriptase antibodies of the invention are contacted with cells, such as a cell line as outlined herein, using standard assays such as MAbZap and HuZap. It would be clear to the skilled person that the MabZap assay is representative of the effect that would be expected to be seen with an antibody-drug conjugate (ADC). In the latter case, the ADC would be internalised, thus taking the drug into the cell. A toxic drug would have the capacity to kill the cell, i.e. to kill the targeted cancer cell. Data from MabZap assays are readily accepted by persons of skill in the art to be representative of ADC assays (Kohls, M and Lappi, D., [2000] Biotechniques, vol. 28, no. 1, 162-165). In these in vitro assay embodiments, the Matriptase antibodies of the invention are added, along with an anti-Matriptase antibody comprising a toxin; for example, the Matriptase antibody may be murine or humanized and the anti-Matriptase antibody can be anti-murine or anti-humanized and contain a toxin such as saporin. Upon formation of the [Matriptase antibody of the invention]-[anti-Matriptase antibody-drug conjugate] complex, the complex is internalized and the drug (e.g. saporin) is released, resulting in cell death. Only upon internalization does the drug get released, and thus cells remain viable in the absence of internalization. As outlined below, without being bound by theory, in therapeutic applications, the anti-Matriptase antibody contains the toxin, and upon internalization, the bond between the antibody and the toxin is cleaved, releasing the toxin and killing the cell.

In addition, the Matriptase antibody may elicit an ADCC response in the presence of effector cells, particularly tumor cells that express Matriptase on the surface.

In one embodiment, the antibody comprises the heavy and light chain complementarity determining regions (CDRs) or variable regions (VRs) of the particular antibodies described herein (e.g., referred to herein as "Matriptase_A1"). Accordingly, in one embodiment, the antibody comprises the CDR1, CDR2, and CDR3 domains of the heavy chain variable (VH) region of antibody A1 having the sequence shown in SEQ ID NO:1, and the CDR1, CDR2 and CDR3 domains of the light chain variable (VL) region of A1 having the sequence shown in SEQ ID NO:2.

In another embodiment, the antibody comprises a heavy chain variable region comprising a first vhCDR comprising SEQ ID NO: 5; a second vhCDR comprising SEQ ID NO: 6; and a third vhCDR comprising SEQ ID NO:7; and a light chain variable region comprising a first vlCDR comprising SEQ ID NO:8; a second vlCDR comprising SEQ ID NO: 9; and a third vlCDR comprising SEQ ID NO:10. In another embodiment, the antibodies of the invention bind to human Matriptase and include a heavy chain variable region including an amino acid sequence selected from the group consisting of SEQ ID NOs:1, and conservative sequence modifications thereof. The antibody may further include a light chain variable region including an amino acid sequence selected from the group consisting of SEQ ID NOs:2, and conservative sequence modifications thereof.

In a further embodiment, the antibodies of the invention bind to human Matriptase and include a heavy chain variable region and a light chain variable region including the amino acid sequences set forth in SEQ ID NOs:1 and/or 2, respectively, and conservative sequence modifications thereof.

Isolated antibodies which include heavy and light chain variable regions having at least 80%, or at least 85%, or at least 90%, or at least 91%, or at least 92%, or at least 93%, or at least 94%, or at least 95%, or at least 96%, or at least 97%, or at least 98%, or at least 99%, or more sequence identity to any of the above sequences are also included in the present invention. Ranges intermediate to the above-recited values, e.g., heavy and light chain variable regions having at least 80-85%, 85-90%, 90-95% or 95-100% sequence identity to any of the above sequences are also intended to be encompassed by the present invention. In one embodiment, the antibody comprises a heavy chain variable region comprising SEQ ID NO:1, or a sequence that is at least 90%, at least 91%, at least 92%, at least 93%, at least 94%, at least 95%, at least 96%, at least 97%, at least 98%, at least 99% identical to SEQ ID NO: 1. In another embodiment, the antibody comprises a light chain variable region comprising SEQ ID NO:2 or a sequence that is at least 90%, at least 91%, at least 92%, at least 93%, at least 94%, at least 95%, at least 96%, at least 97%, at least 98%, at least 99% identical to SEQ ID NO: 2. In another embodiment, the antibody comprises a heavy chain framework region comprising an amino acid sequence that is at least 90%, at least 91%, at least 92%, at least 93%, at least 94%, at least 95%, at least 96%, at least 97%, at least 98%, at least 99% identical to the framework of the heavy chain variable region of SEQ ID NO: 1 comprising SEQ ID NOs: 29, 30, 31 and 32. In another embodiment, the antibody comprises a light chain framework region comprising an amino acid sequence that is at least 90%, at least 91%, at least 92%, at least 93%, at least 94%, at least 95%, at least 96%, at least 97%, at least 98%, at least 99% identical to the framework of the light chain variable region of SEQ ID NO:2, comprising SEQ ID NOs: 33, 34, 35 and 36. In one embodiment, the antibody of the invention is an anti-Matriptase antibody (referred to herein as "A1" antibody) comprising the following CDRs, as well as variants containing a limited number of amino acid variants:

| A1 | SEQ ID NOs |
|---|---|
| variable heavy CDR1 | 5 |
| variable heavy CDR2 | 6 |
| variable heavy CDR3 | 7 |
| variable light CDR1 | 8 |
| variable light CDR2 | 9 |
| variable light CDR3 | 10 |

Disclosed herein are also variable heavy and light chains that comprise the CDR sets of particular Matriptase antibodies of the invention, such as A1, as well as full length heavy and light chains (e.g. comprising constant regions as well). As will be appreciated by those in the art, the CDR sets of the invention can be incorporated into murine, humanized or human constant regions (including framework regions). As shown for A1 and huA1, the amino acid identity between the murine and human sequences is about 90%. Accordingly, the present invention provides variable heavy and light chains that are at least about 90%-99% identical to the SEQ IDs disclosed herein, with 90, 91, 92, 93, 94, 95, 96, 97, 98 and 99% all finding use in the present invention.

Antibodies that Bind to the Same Epitope as the Matriptase Antibodies of the Invention In another embodiment, the invention provides antibodies that bind to the same epitope on the human Matriptase as any of the Matriptase monoclonal antibodies of the invention The term "binds to the same epitope" with reference to two or more antibodies means that the antibodies compete for binding to an antigen and bind to the same, overlapping or encompassing continuous or discontinuous segments of amino acids. Those of skill in the art understand that the phrase "binds to the same epitope" does not necessarily mean that the antibodies bind to exactly the same amino acids. The precise amino acids to which the antibodies bind can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

Accordingly, also, encompassed by the present invention are antibodies that bind to an epitope on Matriptase which comprises all or a portion of an epitope recognized by the particular antibodies described herein (e.g., the same or an overlapping region or a region between or spanning the region).

Also encompassed by the present invention are antibodies that bind the same epitope and/or antibodies that compete for binding to human Matriptase with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as Matriptase. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% % 75-80% 80-85% 85-90% 90-95% 95-99% or more.

Other techniques include, for example, epitope mapping methods, such as, x-ray analyses of crystals of antigen: antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

In a particular embodiment, the antibody competes for binding to Matriptase with an antibody comprising heavy and/or light chain variable regions comprising the amino acid sequences set forth in SEQ ID NOs:1 and 2, respectively, or amino acid sequences at least 80% identical thereto. In another embodiment, the antibody competes for binding to Matriptase with an antibody comprising heavy and/or light chain variable regions comprising the amino acid sequences set forth in SEQ ID NOs:1 and 2 (A1).

Other antibodies of the invention bind to an epitope on Matriptase recognized by the antibodies described herein. In another particular embodiment, the antibody binds to an epitope on Matriptase recognized by an antibody comprising heavy and/or light chain variable regions comprising the amino acid sequences set forth in SEQ ID NOs:1 and 2, or amino acid sequences at least 80%, at least 85%, at least 90%, at least 95%, at least 96%, at least 97%, at least 98% or at least 99% identical thereto. In another embodiment, the antibody binds to an epitope on Matriptase recognized by an antibody comprising heavy and/or light chain variable regions comprising the amino acid sequences set forth in SEQ ID NOs:1 and 2 (A1).

Characterization of Monoclonal Antibodies to Matriptase

Monoclonal antibodies of the invention can be characterized for binding to Matriptase using a variety of known techniques. Generally, the antibodies are initially characterized by ELISA. Briefly, microtiter plates can be coated with purified Matriptase in PBS, and then blocked with irrelevant proteins such as bovine serum albumin (BSA) diluted in PBS. Dilutions of plasma from Matriptase-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the Matriptase immunogen. Hybridomas that bind, preferably with high affinity, to Matriptase can then be subcloned and further characterized. One clone from each hybridoma, which retains the reactivity of the parent cells (by ELISA), can then be chosen for making a cell bank, and for antibody purification.

To purify anti-Matriptase antibodies, selected hybridomas can be grown in roller bottles, two-liter spinner-flasks or other culture systems. Supernatants can be filtered and concentrated before affinity chromatography with protein A-Sepharose (Pharmacia, Piscataway, N.J.) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected anti-Matriptase monoclonal antibodies bind to unique epitopes, each antibody can be biotinylated using commercially available reagents (Pierce, Rockford, Ill.). Biotinylated MAb binding can be detected with a streptavidin labeled probe. To determine the isotype of purified antibodies, isotype ELISAs can be performed using art recognized techniques. For example, wells of microtiter plates can be coated with 10 µg/ml of anti-Ig overnight at 4° C. After blocking with 5% BSA, the plates are reacted with 10 µg/ml of monoclonal antibodies or purified isotype controls, at ambient temperature for two hours. The wells can then be reacted with either IgGI or other isotype specific conjugated probes. Plates are developed and analyzed as described above.

To test the binding of monoclonal antibodies to live cells expressing Matriptase, flow cytometry can be used. Briefly, cell lines and/or human PBMCs expressing membrane-bound Matriptase (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-Matriptase IgGs can be further tested for reactivity with the Matriptase antigen by Western blotting. Briefly, cell extracts from cells expressing Matriptase can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-Matriptase antibodies include standard assays known in the art, for example, Biacore™ surface plasmon resonance (SPR) analysis using a Biacore™ 2000 SPR instrument (Biacore AB, Uppsala, Sweden).

In one embodiment, the antibody specifically binds to human Matriptase comprising SEQ ID NO:26 or a functional fraction, such as the stem (SEQ ID Nos: 21-24). Preferably, an antibody of the invention binds to human Matriptase with high affinity.

Preferably, an antibody of the invention binds to a Matriptase protein with a $K_D$ of $5\times10^{-8}$ M or less, binds to a Matriptase protein with a $K_D$ of $2\times10^{-8}$ M or less, binds to a Matriptase protein with a $K_D$ of $5\times10^{-9}$ M or less, binds to a Matriptase protein with a $K_D$ of $4\times10^{-9}$ M or less, binds to a Matriptase protein with a $K_D$ of $3\times10^{-9}$ M or less, binds to a Matriptase protein with a $K_D$ of $2\times10^{-9}$ M or less, binds to a Matriptase protein with a $K_D$ of $1\times10^{-9}$ M or less, binds to a Matriptase protein with a $K_D$ of $5\times10^{-10}$ M or less, or binds to a Matriptase protein with a $K_D$ of $1\times10^{-10}$ M or less.

In one embodiment, antibodies of the invention compete (e.g., cross-compete) for binding to Matriptase with the particular anti-Matriptase antibodies described herein (e.g., _A1). Such competing antibodies can be identified based on their ability to competitively inhibit binding to Matriptase of one or more of mAbs in standard Matriptase binding assays. For example, standard ELISA assays can be used in which a recombinant human Matriptase protein is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of an anti-Matriptase antibody of the invention to human Matriptase demonstrates that the test antibody can compete with the antibody for binding to human Matriptase In one embodiment, the competing antibody is an antibody that binds to the same epitope on human Matriptase as the particular anti-Matriptase monoclonal antibodies described herein (e.g., A1). Standard epitope mapping techniques, such as x-ray crystallography and 2-dimensional nuclear magnetic resonance, can be used to determine whether an antibody binds to the same epitope as a reference antibody (see, e.g., Epitope Mapping Protocols in Methods in Molecular Biology, Vol. 66, G. E. Morris, Ed. (1996)).

In one embodiment, the antibody that competes for binding to Matriptase and/or binds to the same epitope on human Matriptase is a human antibody. Such human monoclonal antibodies can be prepared and isolated as described in the Examples.

Once a single, archtypal anti-Matriptase mAb has been isolated that has the desired properties described herein, it is straightforward to generate other mAbs with similar properties, e.g., having the same epitope, by using art-known methods. For example, mice may be immunized with Matriptase as described herein, hybridomas produced, and the resulting mAbs screened for the ability to compete with the archtypal mAb for binding to Matriptase. Mice can also be immunized with a smaller fragment of Matriptase containing the epitope to which the archtypal mAb binds. The epitope can be localized by, e.g., screening for binding to a series of overlapping peptides spanning Matriptase. Alternatively, the method of Jespers et al., Biotechnology 12:899, 1994 may be used to guide the selection of mAbs having the same epitope and therefore similar properties to the archtypal mAb. Using phage display, first the heavy chain of the archtypal antibody is paired with a repertoire of (preferably human) light chains to select a Matriptase-binding mAb, and then the new light chain is paired with a repertoire of (preferably human) heavy chains to select a (preferably human) Matriptase-binding mAb having the same epitope as the archtypal mAb. Alternatively variants of the archetypal mAb can be obtained by mutagenesis of cDNA encoding the heavy and light chains of the antibody.

Epitope mapping, e.g., as described in Champe et al. (1995) J. Biol. Chem. 270:1388-1394, can be performed to determine whether the antibody binds an epitope of interest. "Alanine scanning mutagenesis," as described by Cunningham and Wells (1989) Science 244: 1081-1085, or some other form of point mutagenesis of amino acid residues in human Matriptase may also be used to determine the functional epitope for an anti-Matriptase antibody of the present invention. Mutagenesis studies, however, may also reveal amino acid residues that are crucial to the overall three-dimensional structure of Matriptase but that are not directly involved in antibody-antigen contacts, and thus other methods may be necessary to confirm a functional epitope determined using this method.

The epitope bound by a specific antibody may also be determined by assessing binding of the antibody to peptides comprising fragments of human Matriptase. A series of overlapping peptides encompassing the sequence of Matriptase may be synthesized and screened for binding, e.g. in a direct ELISA, a competitive ELISA (where the peptide is assessed for its ability to prevent binding of an antibody to Matriptase bound to a well of a microtiter plate), or on a chip. Such peptide screening methods may not be capable of detecting some discontinuous functional epitopes, i.e. functional epitopes that involve amino acid residues that are not contiguous along the primary sequence of the Matriptase polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in Matriptase when free and when bound in a complex with an antibody of interest (Zinn-Justin et al. (1992) Biochemistry 31, 11335-11347; Zinn-Justin et al. (1993) Biochemistry 32, 6884-6891).

With regard to X-ray crystallography, crystallization may be accomplished using any of the known methods in the art (e.g. Giege et al. (1994) Acta Crystallogr. D50:339-350; McPherson (1990) Eur. J. Biochem. 189:1-23), including microbatch (e.g. Chayen (1997) Structure 5:1269-1274), hanging-drop vapor diffusion (e.g. McPherson (1976) J. Biol. Chem. 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) Meth. Enzymol. 114 & 115, H. W. Wyckoff et al., eds., Academic Press; U.S. Patent Application Publication No. 2004/0014194), and BUSTER (Bricogne (1993) Acta Cryst. D49:37-60; Bricogne (1997) Meth. Enzymol. 276A:361-423, Carter & Sweet, eds.; Roversi et al. (2000) Acta Cryst. D56:1313-1323), the disclosures of which are hereby incorporated by reference in their entireties.

Antibody competition assays, as described herein, can be used to determine whether an antibody "binds to the same epitope" as another antibody. Typically, competition of 50% or more, 60% or more, 70% or more, such as 70%, 71%, 72%, 73%, 74%, 75%, 80%, 85%, 90%, 95%, 96%, 97%, 98%, 99% or more, of an antibody known to interact with the epitope by a second antibody under conditions in which the second antibody is in excess and the first saturates all sites, is indicative that the antibodies "bind to the same epitope." To assess the level of competition between two antibodies, for example, radioimmunoassays or assays using other labels for the antibodies, can be used. For example, a Matriptase antigen can be incubated with a saturating amount of a first anti-Matriptase antibody or antigen-binding fragment thereof conjugated to a labeled compound (e.g., $^3$H, $^{125}$I, biotin, or rubidium) in the presence the same amount of a second unlabeled anti-Matriptase antibody. The amount of labeled antibody that is bound to the antigen in the presence of the unlabeled blocking antibody is then assessed and compared to binding in the absence of the unlabeled blocking antibody. Competition is determined by the percentage change in binding signals in the presence of the unlabeled blocking antibody compared to the absence of the blocking antibody. Thus, if there is a 50% inhibition of binding of the labeled antibody in the presence of the blocking antibody compared to binding in the absence of the blocking antibody, then there is competition between the two antibodies of 50%. Thus, reference to competition between a first and second antibody of 50% or more, 60% or more, 70% or more, such as 70%, 71%, 72%, 73%, 74%, 75%, 80%, 85%, 90%, 95%, 96%, 97%, 98%, 99% or more, means that the first antibody inhibits binding of the second antibody (or vice versa) to the antigen by 50%, 60%, 70%, 71%, 72%, 73%, 74%, 75%, 80%, 85%, 90%, 95%, 96%, 97%, 98%, 99% or more (compared to binding of the antigen by the second antibody in the absence of the first antibody). Thus, inhibition of binding of a first antibody to an antigen by a second antibody of 50%, 605, 70%, 71%, 72%, 73%, 74%, 75%, 80%, 85%, 90%, 95%, 96%, 97%, 98%, 99% or more indicates that the two antibodies bind to the same epitope.

Antibody Modifications

The present invention further provides variant antibodies, sometimes referred to as "antibody derivatives" or "antibody analogs" as well. That is, there are a number of modifications that can be made to the antibodies of the invention, including, but not limited to, amino acid modifications in the CDRs (affinity maturation), amino acid modifications in the Fc region, glycosylation variants, covalent modifications of other types (e.g. for attachment of drug conjugates, etc.

By "variant" herein is meant a polypeptide sequence that differs from that of a parent polypeptide by virtue of at least one amino acid modification. In one embodiment, the parent polypeptide is either the full length variable heavy and/or light chains, listed in SEQ ID Nos: 1 and 2. Amino acid modifications can include substitutions, insertions and deletions, with the former being preferred in many cases.

In general, variants can include any number of modifications, as long as the function of the antibody is still present, as described herein. Accordingly, variant antibodies of the invention, for example, should still specifically bind to human Matriptase. Similarly, if amino acid variants are generated with the Fc region, for example, the variant antibodies should maintain the required receptor binding functions for the particular application or indication of the antibody.

"Variants" in this case can be made in either the listed CDR sequences, the framework or Fc regions of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications (e.g. individual amino acid substitutions, insertions or deletions), with from 1-2, 1-3 and 1-4 also finding use in many embodiments. The number of modifications can depend on the size of the region being modified; for example, in general, fewer modifications are desired in CDR regions. However, as shown herein, the CDRs of the A1 herein are similar, such that a number of amino acid changes can be made and preserve binding.

It should be noted that the number of amino acid modifications may be within functional domains: for example, it may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 91%, 92%, 93%, 94%, 95%, 96%, 97%, 98% or 99% identity to the parent sequences (e.g. the variable regions, the constant regions, and/or the heavy and light chain sequences A1). It should be noted that depending on the size of the sequence, the percent identity will depend on the number of amino acids.

For variable region modification within the VH and/or VL CDR1, CDR2 and/or CDR3 regions, site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed herein) are introduced. The mutations can be amino acid substitutions, additions or deletions, but are preferably substitutions. Moreover, typically no more than one, two, three, four or five residues within a CDR region are altered.

Accordingly, in another embodiment, the instant invention provides isolated anti-Matriptase monoclonal antibodies, or antigen binding portions thereof, comprising: (a) a VH CDR1 region comprising an amino acid sequence selected from the group consisting of SEQ ID NOs:5 or an amino acid sequence having one, two, three, four or five amino acid substitutions, deletions or additions as compared to SEQ ID NOs:5; (b) a VH CDR2 region comprising an amino acid sequence selected from the group consisting of SEQ ID NOs:6, or an amino acid sequence having one, two, three, four or five amino acid substitutions, deletions or additions as compared to SEQ ID NOs:6; (c) a VH CDR3 region comprising an amino acid sequence selected from the group consisting of SEQ ID NOs:7, or an amino acid sequence having one, two, three, four or five amino acid substitutions, deletions or additions as compared to SEQ ID NOs:7; (d) a VL CDR1 region comprising an amino acid sequence selected from the group consisting of SEQ ID NOs:8, or an amino acid sequence having one, two, three, four or five amino acid substitutions, deletions or additions as compared to SEQ ID NOs:8; (e) a VL CDR2 region comprising an amino acid sequence selected from the group consisting of SEQ ID NOs:9, or an amino acid sequence having one, two, three, four or five amino acid substitutions, deletions or additions as compared to SEQ ID NOs: 9; and (f) a VL CDR3 region comprising an amino acid sequence selected from the group consisting of SEQ ID NOs:10, or an amino acid sequence having one, two, three, four or five amino acid substitutions, deletions or additions as compared to SEQ ID NOs:10.

By "amino acid substitution" or "substitution" herein is meant the replacement of an amino acid at a particular position in a parent polypeptide sequence with another amino acid. For example, the substitution S100A refers to a variant polypeptide in which the serine at position 100 is replaced with alanine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "parent polypeptide", "parent protein", "precursor polypeptide", or "precursor protein" as used herein is meant an unmodified polypeptide that is subsequently modified to generate a variant. In general, the parent polypeptides herein are A1) Accordingly, by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

In some embodiments, one or more amino acid modifications are made in one or more of the CDRs of the antibody (any of A1). In general, only 1 or 2 or 3 amino acids are substituted in any single CDR, and generally no more than from 4, 5, 6, 7, 8 9 or 10 changes are made within a set of CDRs. However, it should be appreciated that any combination of no substitutions, 1, 2 or 3 substitutions in any CDR can be independently and optionally combined with any other substitution. In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be done to increase the binding affinity of the antibody for the antigen by at least about 10%, about 20%, about 30%, about 40%, about 50%, about 60%, about 70%, about 80%, about 90%, about 100%, about 110%, about 120%, about 130%, about 140%, about 150% or more, or from 1, 2, 3, 4 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation with variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155: 1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of A1. In addition, as outlined below, amino acid modifications can also independently and optionally be made in any region outside the CDRs, including framework and constant regions as described herein.

In some embodiments, the anti-Matriptase antibodies of the invention are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in U.S. patent application Ser. No. 11/841,654 and references cited therein, US 2004/013210, US 2005/0054832, US 2006/0024298, US 2006/0121032, US 2006/0235208, US 2007/0148170, U.S. Ser. No. 12/341, 769, U.S. Pat. No. 6,737,056, U.S. Pat. No. 7,670,600, U.S. Pat. No. 6,086,875 all of which are expressly incorporated by reference in their entirety, and in particular for specific amino acid substitutions that increase binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference).

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Bispecific Molecules

In another aspect, the present invention features bispecific molecules comprising an anti-Matriptase antibody, or a fragment thereof, of the invention. An antibody of the invention, or antigen-binding portions thereof, can be derivatized or linked to another functional molecule, e.g. another peptide or protein (e.g. another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g. by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for Matriptase and a second binding specificity for a second target epitope. In a particular embodiment of the invention, the second target epitope is an Fc receptor, e.g. human Fcγ RI (CD64) or a human Fcα receptor (CD89). Therefore, the invention includes bispecific molecules capable of binding both to FcγR or FcαR expressing effector cells (e.g. monocytes, macrophages or polymorphonuclear cells (PMNs), and to target cells expressing Matriptase. These bispecific molecules target Matriptase expressing cells to effector cell and trigger Fc receptor-mediated effector cell activities, such as phagocytosis of Matriptase expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-Matriptase binding specificity. In one embodiment, the third binding specificity is an anti-enhancement factor (EF) portion, e.g. a molecule which binds to a surface protein involved in cytotoxic activity and thereby increases the immune response against the target cell. The "anti-enhancement factor portion" can be an antibody, functional antibody fragment or a ligand that binds to a given molecule, e.g. an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g. an Fab, Fab', F(ab')$_2$, Fv, Fd, dAb or a single chain Fv. The antibody may also be a light chain or heavy chain dimer, or any minimal fragment thereof such as an Fv or a single chain construct as described in U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FORM (CD16). In one preferred embodiment, the Fcγ receptor is a human high affinity FcγRI. The human FcγRI is a 72 kDa molecule, which shows high affinity for monomeric IgG ($10^8$-$10^9$ $M^{-1}$).

The production and characterization of certain preferred anti-Fcγ monoclonal antibodies are described in PCT Publication WO 88/00052 and in U.S. Pat. No. 4,954,617, the teachings of which are fully incorporated by reference herein. These antibodies bind to an epitope of FcγRI, FcγRII or Fc γRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g. an Fc-alpha receptor [FcαRI (CD89)], the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ $M^{-1}$) for both IgA1 and IgA2, which is increased upon exposure to cytokines such as G-CSF or GM-CSF [Morton, H. C. et al. (1996) *Critical Reviews in Immunology* 16:423-440]. Four FcαRI-specific monoclonal antibodies, identified as A3, A59, A62 and A77, which bind FcαRI outside the IgA ligand binding domain, have been described [Monteiro, R. C. et al. (1992) *J. Immunol.* 148:1764].

FcαRI and FcγRI are preferred trigger receptors for use in the bispecific molecules of the invention because they are (1) expressed primarily on immune effector cells, e.g. monocytes, PMNs, macrophages and dendritic cells; (2) expressed at high levels (e.g. 5,000-100,000 per cell); (3) mediators of cytotoxic activities (e.g. ADCC, phagocytosis); and (4) mediate enhanced antigen presentation of antigens, including self-antigens, targeted to them.

Antibodies which can be employed in the bispecific molecules of the invention are murine, human, chimeric and humanized monoclonal antibodies.

The bispecific molecules of the present invention can be prepared by conjugating the constituent binding specificities, e.g. the anti-FcR and anti-Matriptase binding specificities, using methods known in the art. For example, the binding specificity of each bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) [see e.g. Karpovsky et al. (1984) *J. Exp. Med.* 160:1686; Liu, M A et al. (1985) *Proc. Natl. Acad. Sci. USA* 82:8648]. Other methods include those described in Paulus (1985) *Behring Ins. Mitt. No.* 78, 118-132; Brennan et al. (1985) *Science* 229:81-83, and Glennie et al. (1987) *J. Immunol.* 139: 2367-2375. Preferred conjugating agents are SATA and sulfo-SMCC, both available from Pierce Chemical Co. (Rockford, Ill.)].

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g. growth inhibition), or Western Blot assay. Each of these assays generally detects the presence of protein-antibody complexes of particular interest by employing a labeled reagent (e.g. an antibody) specific for the complex of interest. For example, the FcR-antibody complexes can be detected using e.g. an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Glycosylation

Another type of covalent modification is alterations in glycosylation. In some embodiments, the antibodies disclosed herein can be modified to include one or more engineered glycoforms. By "engineered glycoform" as used herein is meant a carbohydrate composition that is covalently attached to the antibody, wherein the carbohydrate composition differs chemically from that of a parent antibody. Engineered glycoforms may be useful for a variety of purposes, including but not limited to enhancing or reducing effector function. For example, an aglycoslated antibody can be made (i.e. the antibody that lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al., and can be accomplished by removing the asparagine at position 297.

A preferred form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g. 90-95-98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (POTELLIGENT® technology [Biowa, Inc., Princeton, N.J.]; GlycoMAb® glycosylation engineering technology [Glycart Biotechnology AG, Zurich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example US/2009/0317869, hereby incorporated by reference in its entirety. "Engineered glycoform" typically refers to the different carbohydrate or oligosaccharide as compared to the antibody made in the absence of the glycosylation technology; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference, including removal of fucose residues using a fucosidase enzyme as is known in the art. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689;

4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

In additional embodiments, for example in the use of the antibodies of the invention for diagnostic or detection purposes, the antibodies may comprise a label. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include, but are not limited to, fluorescent lanthanide complexes (including those of Europium and Terbium), and fluorescent labels including, but not limited to, quantum dots, fluorescein, rhodamine, tetramethylrhodamine, eosin, erythrosin, coumarin, methyl-coumarins, pyrene, Malacite green, stilbene, Lucifer Yellow, Cascade Blue, Texas Red, the Alexa dyes, the Cy dyes, and others described in the 6th Edition of the Molecular Probes Handbook by Richard P. Haugland, hereby expressly incorporated by reference.

Antibody-Drug Conjugates

In some embodiments, the anti-Matriptase antibodies of the invention are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety.

Thus the invention provides anti-Matriptase antibodies conjugated to drugs. Generally, conjugation is done by covalent attachment to the antibody, as further described below, and generally relies on a linker, often a peptide linkage (which, as described below, may be designed to be sensitive to cleavage by proteases at the target site or not). In addition, as described above, linkage of the linker-drug unit (LU-D) can be done by attachment to cysteines within the antibody. As will be appreciated by those in the art, the number of drug moieties per antibody can change, depending on the conditions of the reaction, and can vary from 1:1 to 10:1 drug:antibody. As will be appreciated by those in the art, the actual number is an average.

Thus the invention provides anti-Matriptase antibodies conjugated to drugs. As described below, the drug of the ADC can be any number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate) are provided. In other embodiments, the invention further provides methods of using the ADCs.

Drugs for use in the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, taxol, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). Toxins may exert their cytotoxic and cytostatic effects by mechanisms including tubulin binding, DNA binding, or topoisomerase inhibition.

Conjugates of an anti-Matriptase antibody and one or more small molecule toxins, such as a maytansinoids, dolastatins, a hemiasterlin, auristatins, a trichothecene, calicheamicin, and CC1065, and the derivatives of these toxins that have toxin activity, are contemplated. In a preferred embodiment, the toxin is an auristatin, more preferably MMAE or MMAF.

Examples of Conjugates

Examples of conjugates made with an antibody Z(SH)m of this invention (where m is 1, 2, 3, 4, or 5) are shown below. Conjugates A 1 to A 6 and A 8 to A 15 are conjugates in which cleavable group C comprises a peptide bond. Conjugates A 7 and A 16 are conjugates in which cleavable group C is a hydrazone. Conjugates A 17 and A 18 are conjugates in which cleavable group C is a disulfide. In conjugates A 1 to A 2, A 5 to A 9, A 11 to A 14, and A 16, partner molecule D is a cytotoxin having a prodrug moiety attached thereto. Conjugates A 10, A 11, A 14, and A 15 are conjugates having a self-immolating moiety (two in the case of conjugate A 10). Conjugates A 1 through A 8 and A 10 through A 18 illustrate the use of spacers having modular segments.

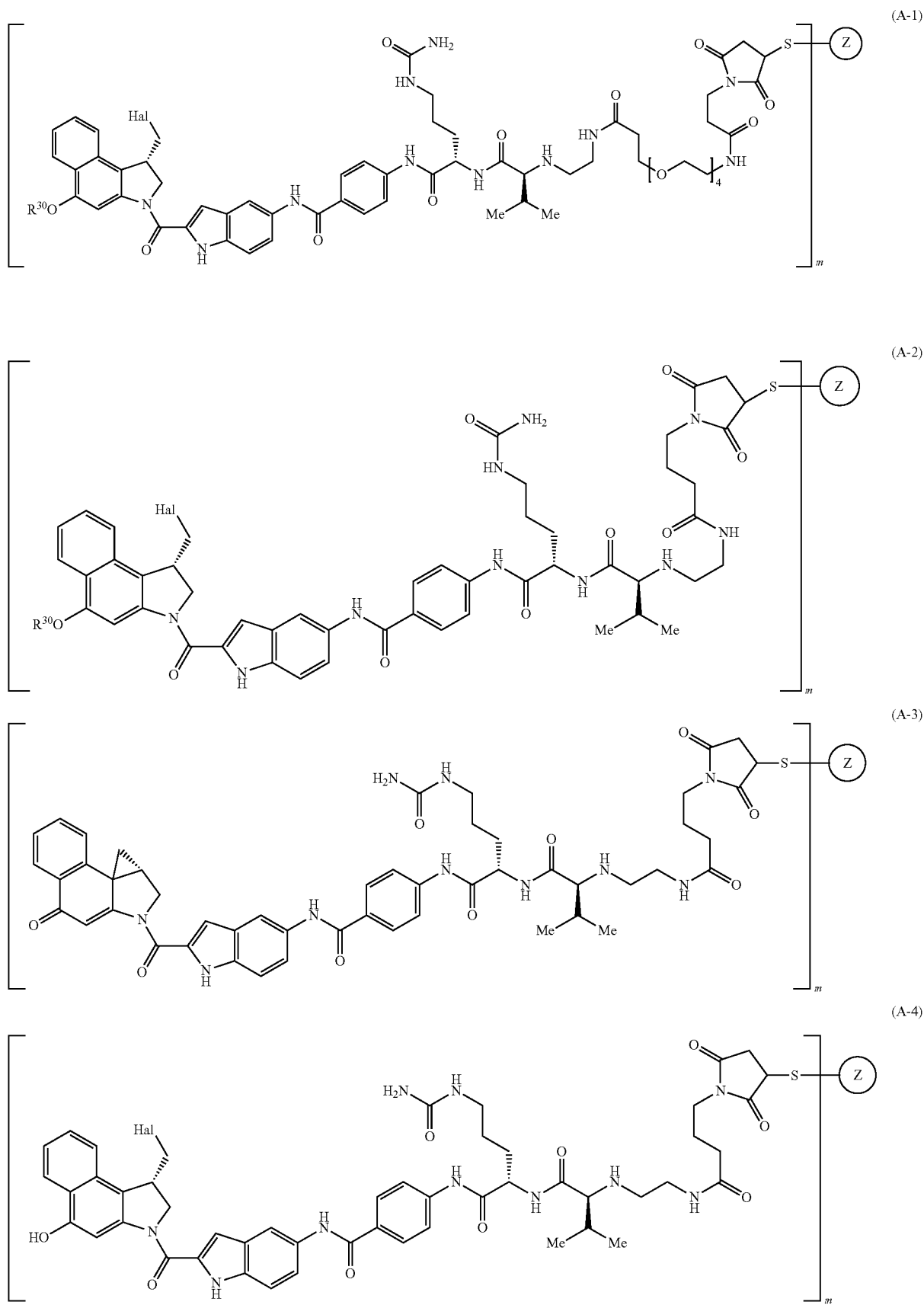

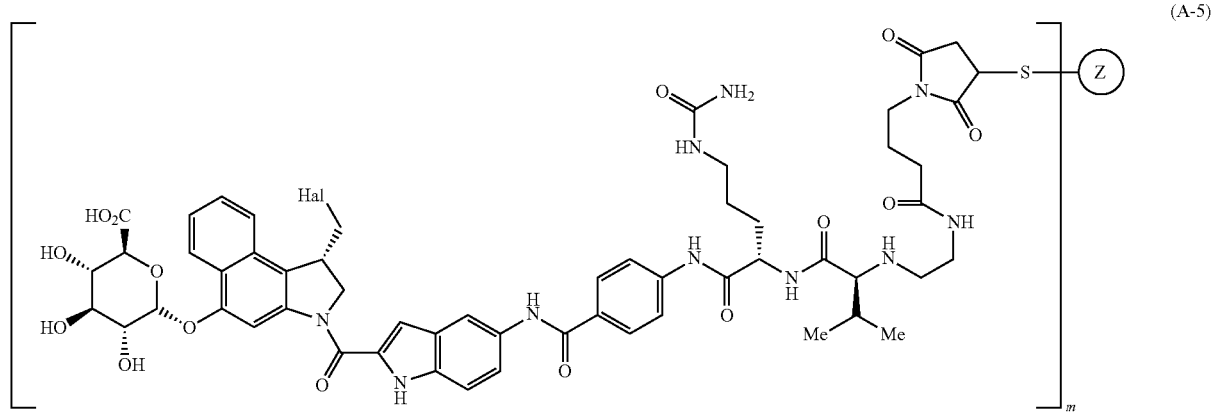
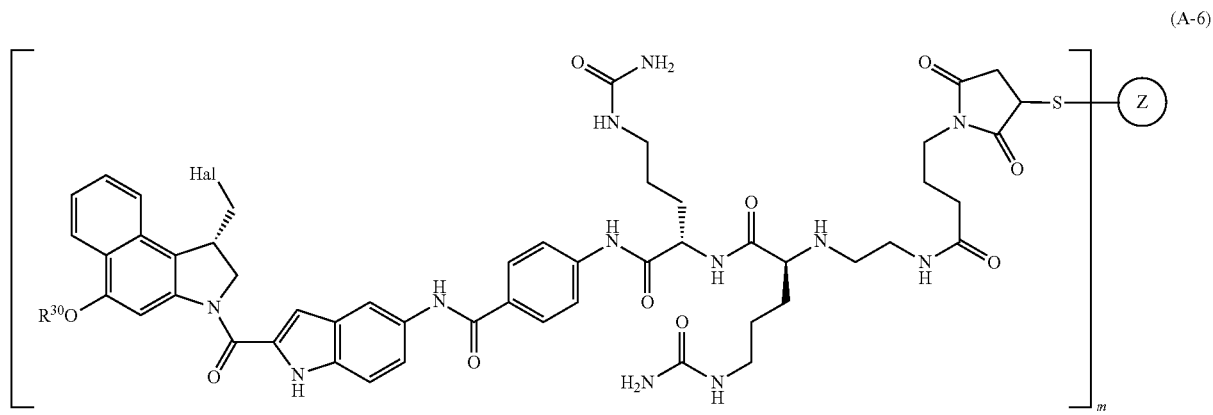
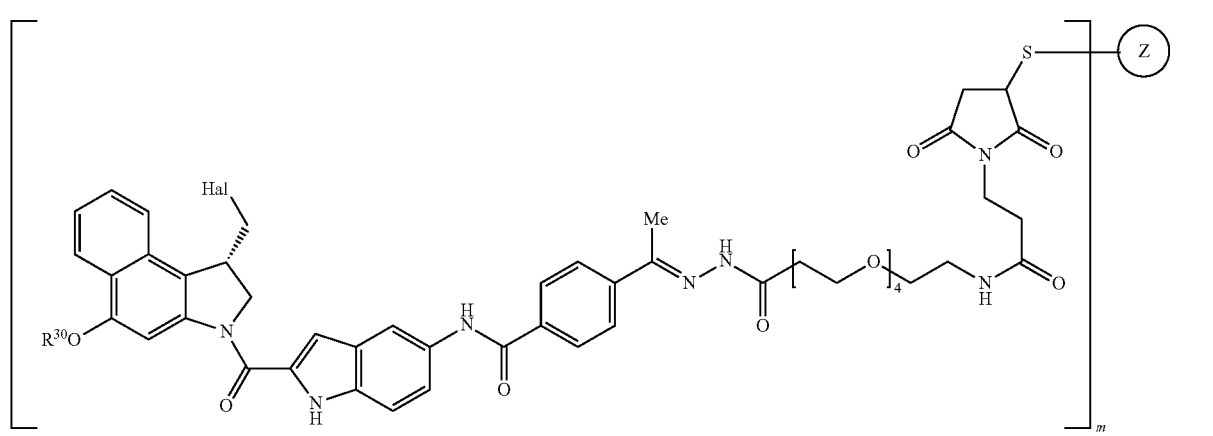

-continued
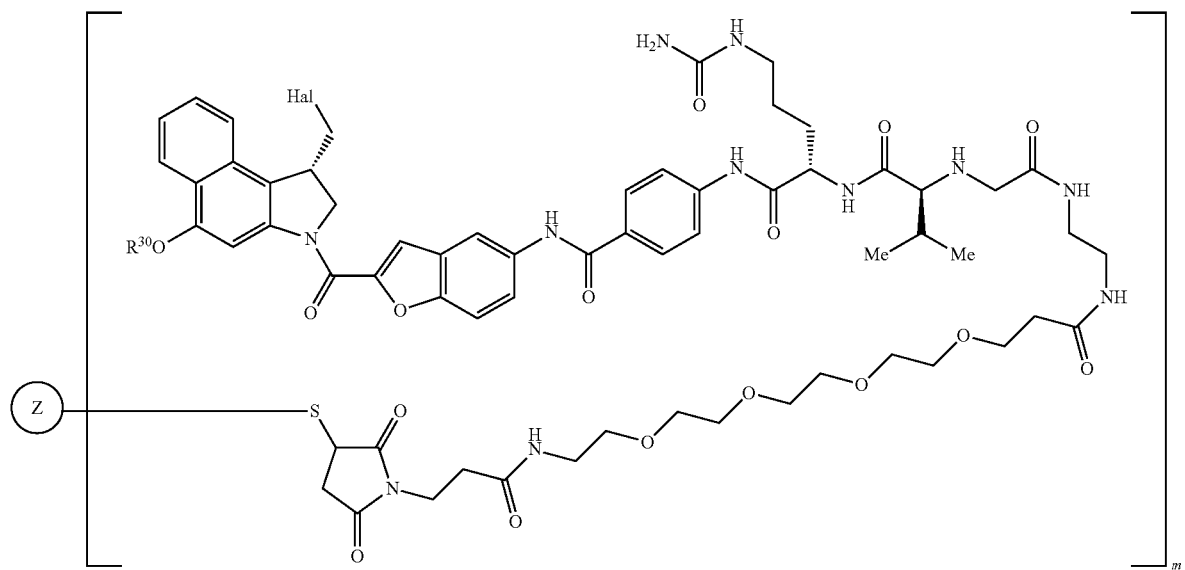
(A-8)
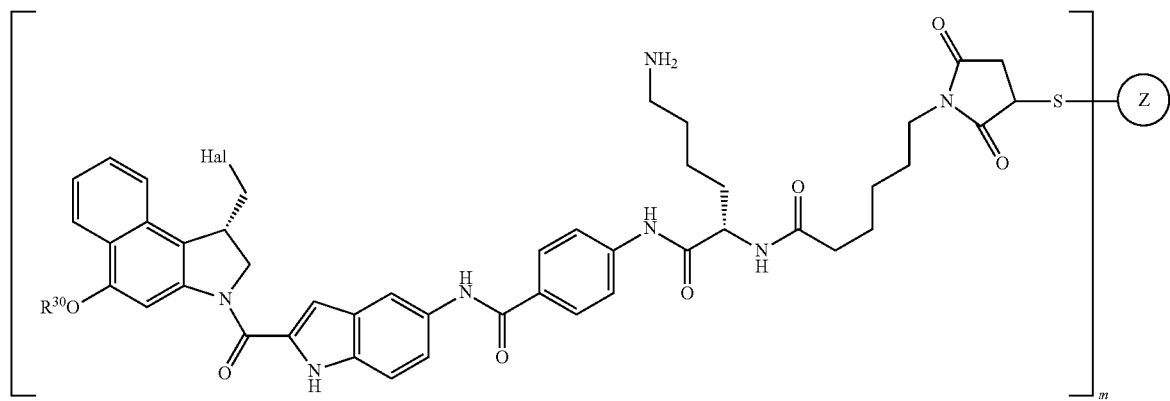
(A-9)
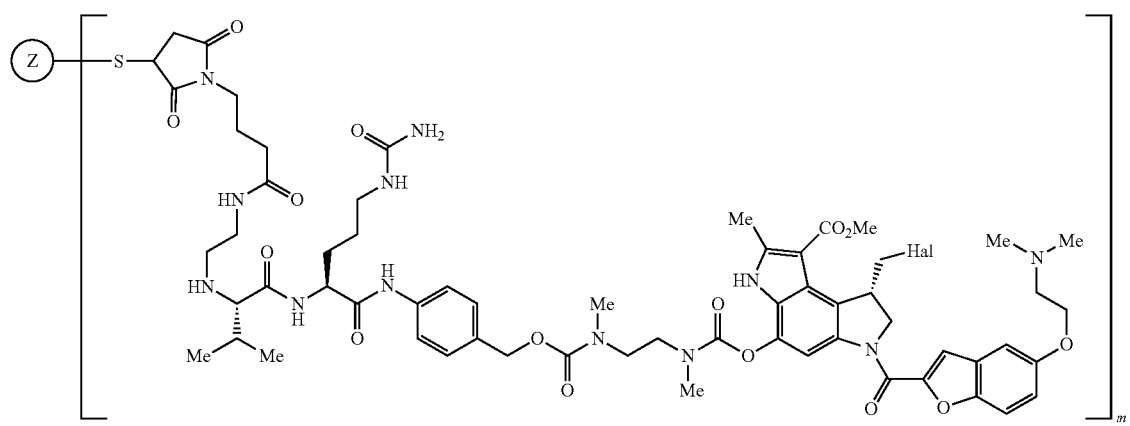
(A-10)

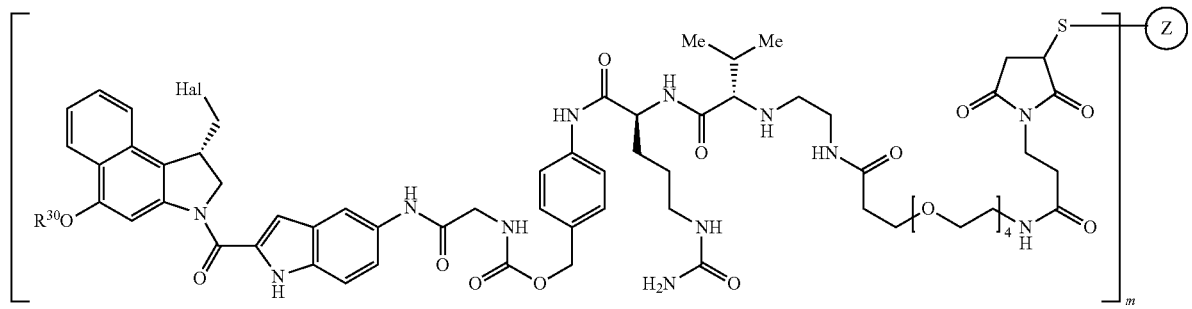
(A-11)
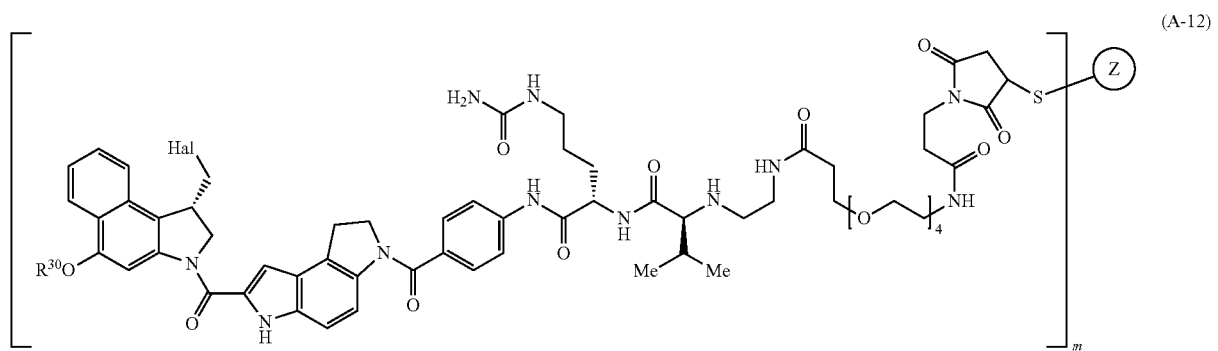
(A-12)
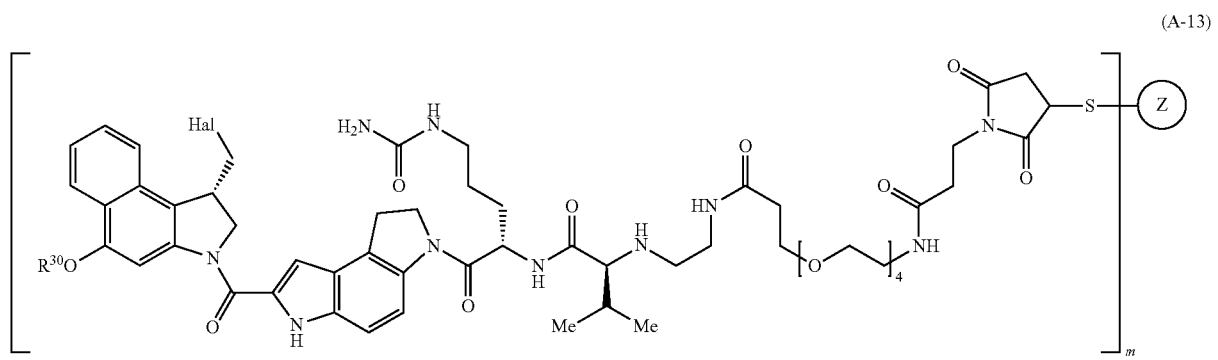
(A-13)
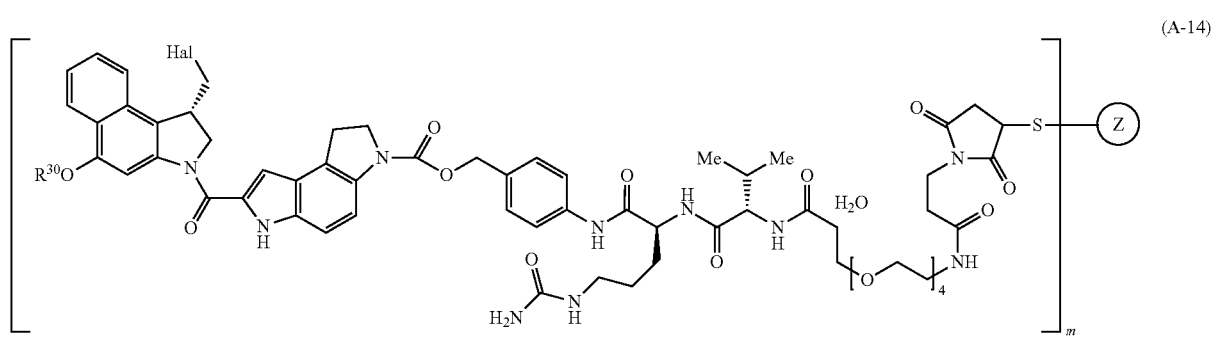
(A-14)

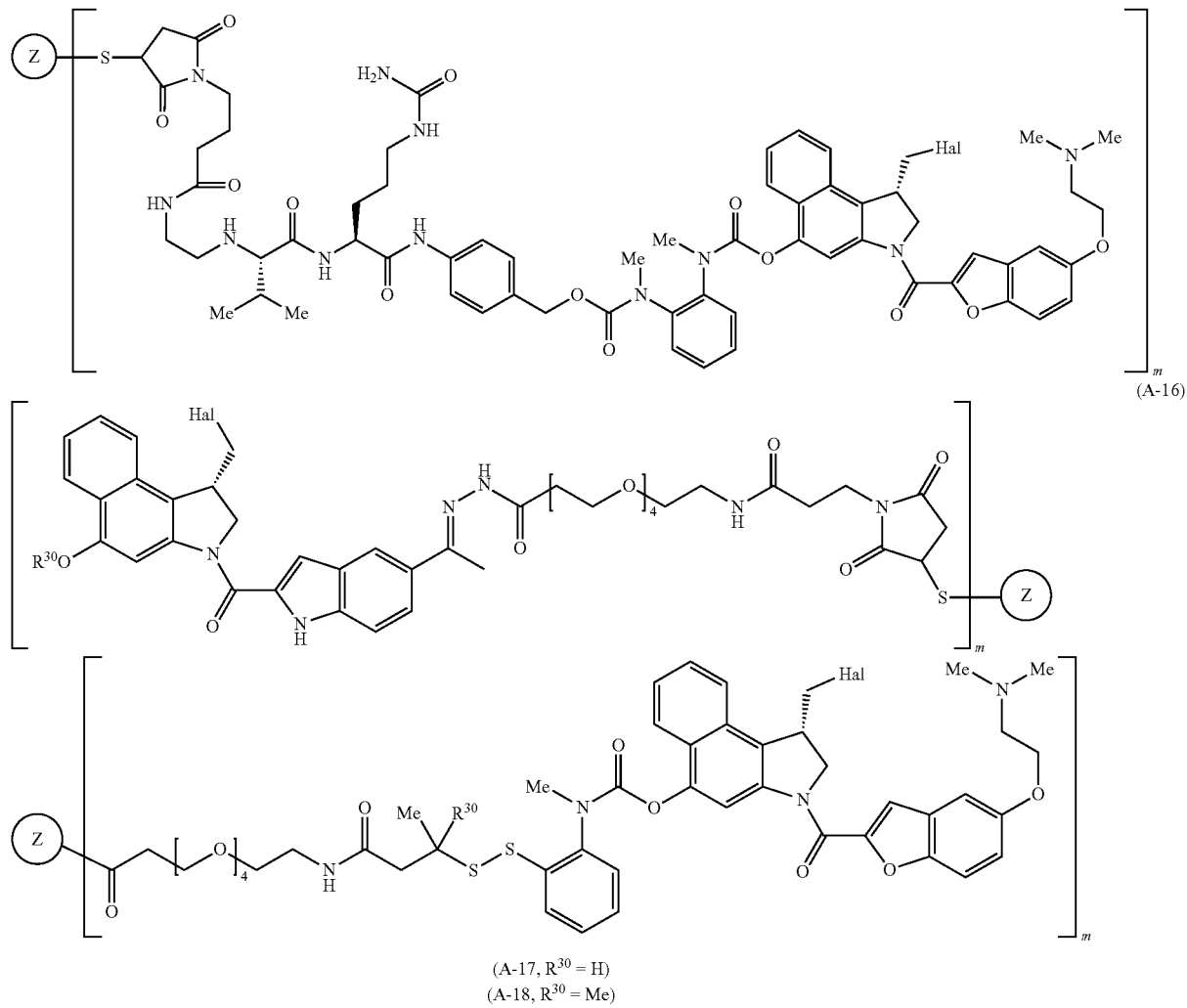

(A-15)
(A-16)
(A-17, R³⁰ = H)
(A-18, R³⁰ = Me)

Where present in the preceding formulae, Hal is Cl or Br and R30 is the carboxyesterase-cleavable carbamate prodrug group shown below:

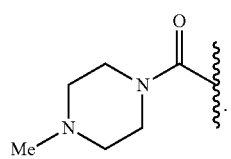

Preparation of Conjugates

Conjugates of this invention preferably are prepared by first joining partner molecule D and linker (XZ)aC(XD)b to form a moiety D (XZ)aC(XD)b R31, where R31 is a functional group suitable for reacting with a functional group on antibody Z, to form the conjugate. Examples of suitable groups R21 include:

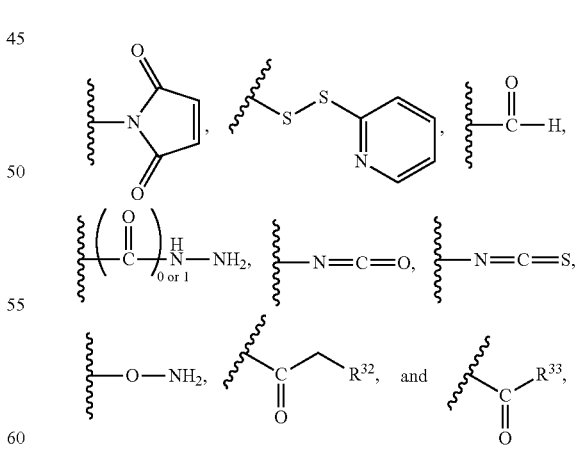

Where R32 is Cl, Br, F, mesylate, or tosylate and R33 is Cl, Br, I, F, OH, O N succinimidyl, O (4-nitrophenyl), O pentafluorophenyl, or —O tetrafluorophenyl. The preparation of suitable moieties D (XZ)aC(XD)b R31 is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1 (2002); Boyd et al., US 2006/0024317 A1 (2006); Chen et al., US 2006/0004081 A1 (2006); Gangwar et al., US 2006/0247295 A1 (2006); Boyd et al., WO 2007/038658 A2 (2007); Gangwar et al., WO 2007/051081 A1 (2007); Gangwar et al., WO 2007/059404 A2 (2007); Sufi et al., WO 2008/083312 A2 (2008); and Chen et al., PCT Application No. PCT/US2008/054362, filed Feb. 20, 2008; the disclosures of which are incorporated herein by reference.

In a preferred embodiment (formula M), R31 is a maleimide group and the functional group on antibody Z is a thiol group as illustrated following, using conjugate A-2 where Hal is Cl and antibody Z(SH)m:

dine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at room temperature. Blank samples of buffer alone plus DTDP are also incubated alongside. After 10 min, absorbance at 324 nm is measured and the number of thiol groups is quantitated using an extinction coefficient for thiopyridine of 19,800 M-1.

Typically a thiolation level of three thiol groups per antibody is desired in this procedure. For example, with

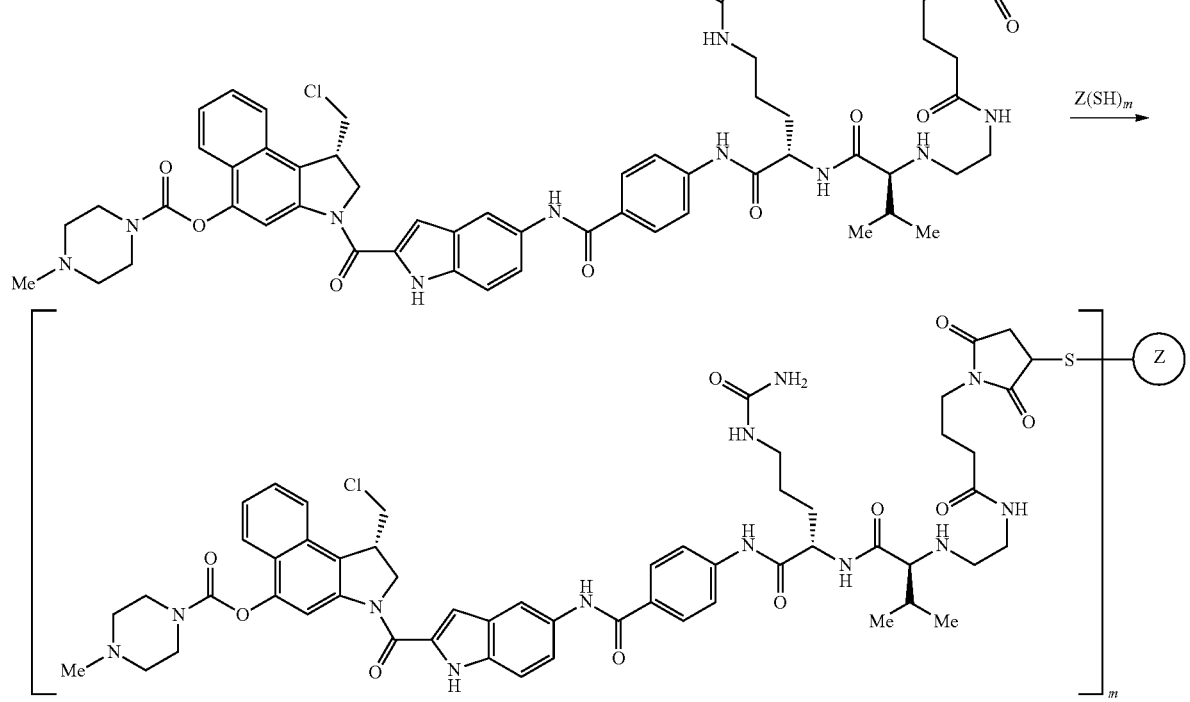

Formula M

The following is an illustrative procedure, based on introduction of free thiol groups into an antibody by reaction of its lysine & amino groups with 2-iminothiolane, followed by reaction with a drug-linker moiety D (XZ)aC(XD)b R31, where R31 is maleimide. Initially the antibody is buffer exchanged into 0.1 M phosphate buffer (pH 8.0) containing 50 mM NaCl and 2 mM DTPA and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at room temperature, the antibody is desalted into 50 mM pH 6.0 HEPES buffer using a Sephadex G-25 column and the number of thiol groups introduced determined rapidly by reaction with dithiodipyrisome antibodies this can be achieved by adding a 15-fold molar excess of 2-iminothiolane followed by incubation at room temperature for 1 h. The antibody is then incubated with 2-iminothiolane at the desired molar ratio and then desalted into conjugation buffer (50 mM pH 6.0 HEPES buffer containing 5 mM glycine and 2 mM DTPA). The thiolated material is maintained on ice while the number of thiols introduced is quantitated as described above.

After verification of the number of thiols introduced, the drug-linker moiety D (XZ)aC(XD)b R31 is added at a 3-fold molar excess per thiol. The conjugation reaction is allowed to proceed in conjugation buffer also containing a final concentration of 5% dimethylsulfoxide (DMSO), or similar alternative solvent. Commonly, the drug-linker stock solution is dissolved in 100% DMSO. The stock solution is added directly to the thiolated antibody, which has enough DMSO added to bring the final concentration to 10%, or pre-diluted in conjugation buffer containing a final concentration of 10% DMSO, followed by addition to an equal volume of thiolated antibody.

The conjugation reaction mixture is incubated at room temperature for 2 h with stirring. Following incubation, the conjugation reaction mixture is centrifuged and filtered through a 0.2 μm filter. Purification of the conjugate can be achieved through chromatography using a number of methods. In one method, the conjugate is purified using size-exclusion chromatography on a Sephacryl S200 column pre-equilibrated with 50 mM pH 7.2 HEPES buffer containing 5 mM glycine and 50 mM NaCl. Chromatography is carried out at a linear flow rate of 28 cm/h. Fractions containing conjugate are collected, pooled and concentrated. In an alternative method, purification can be achieved through ion-exchange chromatography. Conditions vary from antibody to antibody and should to be optimized in each case. For example, antibody-drug conjugate reaction mix is applied to an SP-Sepharose column pre-equilibrated in 50 mM pH 5.5 HEPES containing 5 mM glycine. The antibody conjugate is eluted using a gradient of 0-1 M NaCl in equilibration buffer at pH 5.5. Relevant fractions containing the conjugate are pooled and dialyzed against formulation buffer (50 mM pH 7.2 HEPES buffer containing 5 mM glycine and 100 mM NaCl).

Those skilled in the art will understand that the above-described conditions and methodology are exemplary and non-limiting and that other approaches for conjugating antibodies are known in the art and usable in the present invention.

Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. As described below, drugs may be modified by the incorporation of a functionally active group such as a thiol or amine group for conjugation to the antibody.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions.

Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH2OR) (U.S. Pat. No. 4,331,598); C-14-hydroxymethyl or acyloxymethyl (CH2OH or CH2OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Of particular use are DM1 (disclosed in U.S. Pat. No. 5,208,020, incorporated by reference) and DM4 (disclosed in U.S. Pat. No. 7,276,497, incorporated by reference). See also a number of additional maytansinoid derivatives and methods in U.S. Pat. No. 5,416,064, WO/01/24763, U.S. Pat. Nos. 7,303,749, 7,601,354, U.S. Ser. No. 12/631,508, WO02/098883, 6,441,163, 7,368,565, WO02/16368 and WO04/1033272, all of which are expressly incorporated by reference in their entirety.

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Auristatins and Dolastatins

In some embodiments, the ADC comprises an anti-Matriptase antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238648, the disclosure of which is expressly incorporated by reference in its entirety.

An exemplary preferred auristatin embodiment is MMAE (see U.S. Pat. No. 6,884,869 expressly incorporated by reference in its entirety).

Another exemplary auristatin embodiment is MMAF, (US 2005/0238649, U.S. Pat. Nos. 5,767,237 and 6,124,431, expressly incorporated by reference in their entirety).

Additional exemplary embodiments comprising MMAE or MMAF and various linker components (described further herein) have the following structures and abbreviations (wherein Ab means antibody and p is 1 to about 8, for example 1, 2, 3, 4, 5, 6, 7 or 8).

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

Calicheamicin

In other embodiments, the ADC comprises an antibody of the invention conjugated to one or more calicheamicin molecules. For example, Mylotarg is the first commercial ADC drug and utilizes calicheamicin γ1 as the payload (see U.S. Pat. No. 4,970,198, incorporated by reference in its entirety). Additional calicheamicin derivatives are described in U.S. Pat. Nos. 5,264,586, 5,384,412, 5,550,246, 5,739,116, 5,773,001, 5,767,285 and 5,877,296, all expressly incorporated by reference. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α2I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Duocarmycins

CC-1065 (see U.S. Pat. No. 4,169,888, incorporated by reference) and duocarmycins are members of a family of antitumor antibiotics utilized in ADCs. These antibiotics appear to work through sequence-selectively alkylating DNA at the N3 of adenine in the minor groove, which initiates a cascade of events that result in apoptosis.

Important members of the duocamycins include duocarmycin A (U.S. Pat. No. 4,923,990, incorporated by reference) and duocarmycin SA (U.S. Pat. No. 5,101,038, incorporated by reference), and a large number of analogues as described in U.S. Pat. Nos. 7,517,903, 7,691,962, 5,101,038; 5,641,780; 5,187,186; 5,070,092; 5,070,092; 5,641,780; 5,101,038; 5,084,468, 5,475,092, 5,585,499, 5,846,545, WO2007/089149, WO2009/017394A1, U.S. Pat. Nos. 5,703,080, 6,989,452, 7,087,600, 7,129,261, 7,498,302, and 7,507,420, all of which are expressly incorporated by reference.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate Iodine-123. "Monoclonal Antibodies in Immunoscintigraphy" (Chatal, CRC Press 1989) describes other methods in detail.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined.

In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is 2, 3, 4, 5, 6, 7, or 8 or a fraction thereof The generation of Antibody-drug conjugate compounds can be accomplished by any technique known to the skilled artisan. Briefly, the Antibody-drug conjugate compounds can include an anti-Matriptase antibody as the Antibody unit, a drug, and optionally a linker that joins the drug and the binding agent.

A number of different reactions are available for covalent attachment of drugs and/or linkers to binding agents. This is can be accomplished by reaction of the amino acid residues of the binding agent, for example, antibody molecule, including the amine groups of lysine, the free carboxylic acid groups of glutamic and aspartic acid, the sulfhydryl groups of cysteine and the various moieties of the aromatic amino acids. A commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule.

Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention In some embodiments, an intermediate, which is the precursor of the linker, is reacted with the drug under appropriate conditions. In other embodiments, reactive groups are used on the drug and/or the intermediate. The product of the reaction between the drug and the intermediate, or the derivatized drug, is subsequently reacted with an anti-Matriptase antibody of the invention under appropriate conditions.

It will be understood that chemical modifications may also be made to the desired compound in order to make reactions of that compound more convenient for purposes of preparing conjugates of the invention. For example a functional group e.g. amine, hydroxyl, or sulfhydryl, may be appended to the drug at a position which has minimal or an acceptable effect on the activity or other properties of the drug.

Linker Units

Typically, the antibody-drug conjugate compounds comprise a Linker unit between the drug unit and the antibody unit. In some embodiments, the linker is cleavable under intracellular or extracellular conditions, such that cleavage of the linker releases the drug unit from the antibody in the appropriate environment. For example, solid tumors that secrete certain proteases may serve as the target of the cleavable linker; in other embodiments, it is the intracellular proteases that are utilized. In yet other embodiments, the linker unit is not cleavable and the drug is released, for example, by antibody degradation in lysosomes.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers that are cleavable by enzymes that are present in Matriptase-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: X)). Other examples of such linkers are described, e.g., in U.S. Pat. No. 6,214,345, incorporated herein by reference in its entirety and for all purposes In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

In many embodiments, the linker is self-immolative. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved. See for example, WO 2007059404A2, WO06110476A2, WO05112919A2, WO2010/062171, WO09/017394, WO07/089149, WO 07/018431, WO04/043493 and WO02/083180, which are directed to drug-cleavable substrate conjugates where the drug and cleavable substrate are optionally linked through a self-immolative linker and which are all expressly incorporated by reference.

Often the linker is not substantially sensitive to the extracellular environment. As used herein, "not substantially sensitive to the extracellular environment," in the context of a linker, means that no more than about 20%, 15%, 10%, 5%, 3%, or no more than about 1% of the linkers, in a sample of antibody-drug conjugate compound, are cleaved when the antibody-drug conjugate compound presents in an extracellular environment (for example, in plasma).

Whether a linker is not substantially sensitive to the extracellular environment can be determined, for example, by incubating with plasma the antibody-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the antibody-drug conjugate compound as described herein). In yet other embodiments, the linker promotes cellular internalization when conjugated to both the auristatin compound and the anti-Matriptase antibodies of the invention.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

Drug Loading

Drug loading is represented by p and is the average number of Drug moieties per antibody in a molecule. Drug loading ("p") may be 1, 2, 3, 4, 5, 6, 7, 8, 9, 10, 11, 12, 13, 14, 15, 16, 17, 18, 19, 20 or more moieties (D) per antibody, although frequently the average number is a fraction or a decimal. Generally, drug loading of from 1 to 4 is frequently useful, and from 1 to 2 is also useful. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography.

In some embodiments, a homogeneous ADC with a single loading value may be isolated from the conjugation mixture by electrophoresis or chromatography.

Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug conjugate is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16).

In vivo, the effect of a therapeutic composition of the anti-Matriptase antibody of the invention can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3: 402-408). Efficacy can be measured using assays that measure inhibition of tumor formation, tumor regression or metastasis, and the like.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed 1980).

Methods for Producing the Antibodies of the Invention

The present invention further provides methods for producing the disclosed anti-Matriptase antibodies. These methods encompass culturing a host cell containing isolated nucleic acid(s) encoding the antibodies of the invention. As will be appreciated by those in the art, this can be done in a variety of ways, depending on the nature of the antibody. In some embodiments, in the case where the antibodies of the invention are full length traditional antibodies, for example, a heavy chain variable region and a light chain variable region under conditions such that an antibody is produced and can be isolated.

The variable heavy and light chains of antibodies A1-A14 are disclosed herein (both protein and nucleic acid sequences); as will be appreciated in the art, these can be easily augmented to produce full length heavy and light chains. That is, having provided the DNA fragments encoding $V_H$ and $V_K$ segments as outlined herein, these DNA fragments can be further manipulated by standard recombinant DNA techniques, for example, to convert the variable region genes to full-length antibody chain genes, to Fab fragment genes, or to a scFv gene. In these manipulations, a $V_K$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$). The sequences of murine heavy chain constant region genes are known in the art [see e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the VL/VK region can be converted to a full-length light chain gene (as well as a Fab light chain gene) by operatively linking the $V_L$-encoding DNA to another DNA molecule encoding the light chain constant region, $C_L$. The sequences of murine light chain constant region genes are known in the art [see, e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. In preferred embodiments, the light chain constant region can be a kappa or lambda constant region.

To create a scFv gene, the $V_H$- and $V_L/V_K$-encoding DNA fragments are operatively linked to another fragment encoding a flexible linker, e.g. encoding the amino acid sequence $(Gly_4\text{-}Ser)_3$, such that the $V_H$ and $V_L/V_K$ sequences can be expressed as a contiguous single-chain protein, with the $V_L/V_K$ and $V_H$ regions joined by the flexible linker [see e.g. Bird et al. (1988) Science 242:423-426; Huston et al. (1988) Proc. Natl. Acad. Sci. USA 85:5879-5883; McCafferty et al., (1990) Nature 348:552-554].

In general, nucleic acids are provided which encode the antibodies of the invention. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs, and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, Va. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

General methods for antibody molecular biology, expression, purification, and screening are well known, for example, see U.S. Pat. Nos. 4,816,567, 4,816,397, 6,331,415 and 7,923,221, as well as Antibody Engineering, edited by Kontermann & Dubel, Springer, Heidelberg, 2001 and 2010 Hayhurst & Georgiou, 2001, Curr Opin Chem Biol 5:683-689; Maynard & Georgiou, 2000, Annu Rev Biomed Eng 2:339-76; and Morrison, S. (1985) Science 229:1202.

Pharmaceutical Compositions

In another aspect, the present invention provides a composition, e.g. a pharmaceutical composition, containing one or a combination of Matriptase antibodies, or antigen-binding portion(s) thereof, of the present invention, formulated together with a pharmaceutically acceptable carrier. Such compositions may include one or a combination of (e.g. two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e. combined with other agents. For example, the combination therapy can include an anti-antibody of the present invention combined with at least one other anti-tumor agent, or an anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion). Depending on the route of administration, the active compound, i.e. antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects [see, e.g. Berge, S. M., et al. (1977) J. Pharm. Sci. 66:1-19]. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of 100 percent, this amount will range from about 0.01 percent to about 99 percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-Matriptase antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-Matriptase antibody of the invention preferably results in a decrease in severity of disease symptoms, an increase in frequency and duration of disease symptom-free periods, or a prevention of impairment or disability due to the disease affliction. For example, for the treatment of the Matriptase mediated tumors, a "therapeutically effective dosage" preferably inhibits cell growth or tumor growth by at least about 20%, at least about 30%, more preferably by at least about 40%, at least about 50%, even more preferably by at least about 60%, at least about 70% and still more preferably by at least about 80% or at least about 90% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art [see, e.g. *Sustained and Controlled Release Drug Delivery Systems* (1978) J. R. Robinson, ed., Marcel Dekker, Inc., N.Y].

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery [see, e.g. V. V. Ranade (1989) *J. Clin. Pharmacol.* 29:685]. Exemplary targeting moieties include folate or biotin (see, e.g. U.S. Pat. No. 5,416,016.); mannosides [Umezawa et al. (1988) *Biochem. Biophys. Res. Commun.* 153:1038]; antibodies [P. G. Bloeman et al. (1995) *FEBS Lett.* 357:140; M. Owais et al. (1995) *Antimicrob. Agents Chemother.* 39:180]; surfactant protein A receptor [Briscoe et al. (1995) *Am. J. Physiol.* 1233:134]; p 120 [Schreier et al. (1994) *J. Biol. Chem.* 269:9090]; see also K. Keinanen; M. L. Laukkanen (1994) *FEBS Lett.* 346:123; J. J. Killion; I. J. Fidler (1994) *Immunomethods* 4:273.

Uses and Methods

The antibodies, antibody compositions and methods of the present invention have numerous in vitro and in vivo diagnostic and therapeutic utilities involving the diagnosis and treatment of Matriptase mediated disorders.

In some embodiments, these molecules can be administered to cells in culture, in vitro or ex vivo, or to human subjects, e.g. in vivo, to treat, prevent and to diagnose a variety of disorders. As used herein, the term "subject" is intended to include human and non-human animals. Non-human animals include all vertebrates, e.g. mammals and non-mammals, such as non-human primates, sheep, dogs, cats, cows, horses, chickens, amphibians, and reptiles. Preferred subjects include human patients having disorders mediated by Matriptase activity. The methods are particularly suitable for treating human patients having a disorder associated with the aberrant Matriptase expression. When antibodies to Matriptase are administered together with another agent, the two can be administered in either order or simultaneously.

Given the specific binding of the antibodies of the invention for Matriptase, the antibodies of the invention can be used to specifically detect Matriptase expression on the surface of cells and, moreover, can be used to purify Matriptase via immunoaffinity purification.

Furthermore, given the expression of Matriptase on tumor cells, the antibodies, antibody compositions and methods of the present invention can be used to treat a subject with a tumorigenic disorder, e.g. a disorder characterized by the presence of tumor cells expressing Matriptase including, for example gastric cancer, colorectal cancer, prostate cancer, breast cancer, ovarian cancer lung cancer, preferably SCLC, esophageal cancer, head and neck cancer, pancreatic cancer, lymphoma preferably non-Hodgkin's lymphoma and skin cancer. Matriptase has been demonstrated to be internalised on antibody binding as illustrated in Examples 5 and 7 below, thus enabling the antibodies of the invention to be used in any payload mechanism of action e.g. an ADC approach, radioimmunoconjugate, or ADEPT approach.

In one embodiment, the antibodies (e.g. monoclonal antibodies, antibody fragments, Nanobodies, multispecific and bispecific molecules and compositions, etc.) of the invention can be used to detect levels of Matriptase, or levels of cells which contain Matriptase on their membrane surface, which levels can then be linked to certain disease symptoms. Alternatively, the antibodies, generally administered as ADCs, can be used to inhibit or block Matriptase function which, in turn, can be linked to the prevention or amelioration of certain disease symptoms, thereby implicating the Matriptase as a mediator of the disease. This can be achieved by contacting a sample and a control sample with the anti-Matriptase antibody under conditions that allow for the formation of a complex between the antibody and Matriptase. Any complexes formed between the antibody and the Matriptase are detected and compared in the sample and the control.

In another embodiment, the antibodies (e.g. monoclonal antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g. monoclonal antibodies, multispecific and bispecific molecules, immunoconjugates and compositions) of the invention have additional utility in therapy and diagnosis of Matriptase related diseases. For example, the monoclonal antibodies, the multispecific or bispecific molecules and the immunoconjugates can be used to elicit in vivo or in vitro one or more of the following biological activities: to inhibit the growth of and/or kill a cell expressing Matriptase; to mediate phagocytosis or ADCC of a cell expressing Matriptase in the presence of human effector cells, or to block Matriptase ligand binding to Matriptase.

In a particular embodiment, the antibodies (e.g. monoclonal antibodies, multispecific and bispecific molecules and compositions) are used in vivo to treat, prevent or diagnose a variety of Matriptase-related diseases. Examples of Matriptase-related diseases include, among others, human cancer tissues representing gastric cancer, colorectal cancer, prostate cancer, breast cancer, ovarian cancer lung cancer, preferably SCLC, esophageal cancer, head and neck cancer, pancreatic cancer, lymphoma preferably non-Hodgkin's lymphoma and skin cancer.

Suitable routes of administering the antibody compositions (e.g. monoclonal antibodies, multispecific and bispecific molecules and immunoconjugates) of the invention in vivo and in vitro are well known in the art and can be selected by those of ordinary skill. For example, the antibody compositions can be administered by injection (e.g. intravenous or subcutaneous). Suitable dosages of the molecules used will depend on the age and weight of the subject and the concentration and/or formulation of the antibody composition.

As previously described, the anti-Matriptase antibodies of the invention can be co-administered with one or other more therapeutic agents, e.g. a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g. an anti-cancer therapy, e.g. radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Other agents suitable for co-administration with the antibodies of the invention include other agents used for the treatment of cancers, e.g. gastric cancer, colorectal cancer, prostate cancer, breast cancer, ovarian cancer or lung cancer, esophageal cancer, head and neck cancer, pancreatic cancer, lymphoma preferably non-Hodgkin's lymphoma and skin cancer, such as Avastin®, 5FU and gemcitabine. Co-administration of the anti-Matriptase antibodies or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g. effector cells linked to compositions (e.g. monoclonal antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$, but will vary depending on the therapeutic purpose. In general, the amount will be sufficient to obtain localization at the target cell, e.g. a tumor cell expressing Matriptase, and to affect cell killing by, e.g. phagocytosis. Routes of administration can also vary.

Therapy with target-specific effector cells can be performed in conjunction with other techniques for removal of targeted cells. For example, anti-tumor therapy using the compositions (e.g. monoclonal antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-Matriptase antibodies linked to anti-Fc-gamma RI or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g. monoclonal antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g. monoclonal antibodies, multispecific and bispecific molecules) of the invention can also be lysed by complement. In yet another embodiment, the compositions of the invention do not activate complement.

The compositions (e.g. monoclonal antibodies, multispecific and bispecific molecules and immunoconjugates) of the invention can also be administered together with complement. In certain embodiments, the instant disclosure provides compositions comprising antibodies, multispecific or bispecific molecules and serum or complement. These compositions can be advantageous when the complement is located in close proximity to the antibodies, multispecific or bispecific molecules. Alternatively, the antibodies, multispecific or bispecific molecules of the invention and the complement or serum can be administered separately.

Also within the scope of the present invention are kits comprising the antibody compositions of the invention (e.g. monoclonal antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional antibodies of the invention (e.g. an antibody having a complementary activity which binds to an epitope in the Matriptase antigen distinct from the first antibody).

Accordingly, patients treated with antibody compositions of the invention can be additionally administered (prior to, simultaneously with, or following administration of an antibody of the invention) with another therapeutic agent, such as a cytotoxic or radiotoxic agent, which enhances or augments the therapeutic effect of the antibodies.

In other embodiments, the subject can be additionally treated with an agent that modulates, e.g. enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g. antibodies, multispecific and bispecific molecules) of the invention can also be used to target cells expressing FcγR or Matriptase, for example, for labeling such cells. For such use, the binding agent can be linked to a molecule that can be detected. Thus, the invention provides methods for localizing ex vivo or in vitro cells expressing Fc receptors, such as FcγR, or Matriptase. The detectable label can be, e.g. a radioisotope, a fluorescent compound, an enzyme, or an enzyme co-factor.

In a particular embodiment, the invention provides methods for detecting the presence of the Matriptase antigen in a sample, or measuring the amount of the Matriptase antigen, comprising contacting the sample, and a control sample, with a monoclonal antibody, or an antigen binding portion thereof, which specifically binds to Matriptase, under conditions that allow for formation of a complex between the antibody or portion thereof and Matriptase. The formation of a complex is then detected, wherein a difference complex formation between the sample compared to the control sample is indicative the presence of the Matriptase antigen in the sample.

In other embodiments, the invention provides methods for treating an Matriptase mediated disorder in a subject, e.g. human cancers, including gastric cancer, colorectal cancer, prostate cancer, breast cancer, ovarian cancer lung cancer, preferably SCLC, esophageal cancer, head and neck cancer, pancreatic cancer, lymphoma preferably non-Hodgkin's lymphoma and skin cancer.

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependant claims.

The present invention is further illustrated by the following examples which should not be construed as further limiting.

Example 1: Generation of Human Monoclonal Antibodies Against Matriptase-Antigen

The Matriptase-stem protein is known to be abundantly expressed in MCF7 cells. These cells were used in the following protocol for immunization.

Transgenic HuMAb Mouse® Strains

Fully human monoclonal antibodies to Matriptase were prepared using HCo12 strains of the transgenic HuMAb Mouse®, which express human antibody genes. In these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187.

HuMab Immunizations

To generate fully human monoclonal antibodies to Matriptase, HuMab mice of the HCo12 Mouse strains were immunized with Matriptase-expressing MCF7 cells. General immunization schemes for these mice are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of Matriptase-expressing MCF7 cells.

Transgenic mice were immunized with the Matriptase-expressing MCF7 cells in Ribi adjuvant either intraperitonealy (IP), subcutaneously (Sc) or via footpad (FP) in 3-21 days intervals (up to a total of 9 immunizations). The immune response was monitored by retroorbital bleeds. The plasma was screened by ELISA (as described below), and mice with sufficient titers of anti-Matriptase human immunoglobulin were used for fusions. Mice were boosted intravenously with antigen 3 and 2 days before sacrifice and removal of the spleen. Typically, 10-20 fusions for each antigen were performed. Several dozen mice were immunized for each antigen.

Selection of a HuMab Mouse® Animal Producing Anti-Matriptase Antibodies

To select a HuMab Mouse® animal producing antibodies that bound Matriptase, sera from immunized mice was tested by ELISA as described by Fishwild, D. et al. (1996) (supra). Briefly, microtiter plates were coated with purified recombinant Matriptase at 1-2 µg/ml in PBS, 50 µl/wells incubated 4° C. overnight then blocked with 200 µl/well of 5% chicken serum in PBS/Tween (0.05%). Dilutions of plasma from Matriptase-immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Moss Inc, product: ABTS-1000) and analyzed by spectrophotometer at OD 415-495. Mice that developed the highest titers of anti-Matriptase antibodies were used for fusions. Fusions were performed as described below and hybridoma supernatants were tested for anti-Matriptase activity by ELISA and FACS.

Generation of Hybridomas Producing Human Monoclonal Antibodies to Matriptase

The mouse splenocytes, isolated from a HuMab Mouse®, were fused with a mouse myeloma cell line using electric field based electrofusion using a Cyto Pulse large chamber cull fusion electroporator (Cyto Pulse Sciences, Inc., Glen Burnie, Md.). Briefly, single cell suspensions of splenic lymphocytes from immunized mice were fused to equal number of Sp2/0 nonsecreting mouse myeloma cells (ATCC, CRL 1581). Cells were plated at a density of approximately $2 \times 10^4$/well in flat bottom microtiter plates, which were then incubated in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Approximately 10-14 days after cell plating, supernatants from individual wells were screened first for whether they contained human g,k antibodies. The supernatants which were scored positive for human g,k were then subsequently screened-by ELISA and FACS (described above) for human anti-Matriptase monoclonal IgG antibodies. The antibody secreting hybridomas were transferred to 24 well plates, screened again and, if still positive for human anti-Matriptase IgG monoclonal antibodies, were subcloned at least twice by limiting dilution. The stable subclones were then cultured in vitro to generate small amounts of antibody in tissue culture medium for further characterization.

Hybridoma clone coding for Matriptase_A1 generated from a HuMab Mouse®, was selected for further analysis.

Example 2: Structural Characterization of Monoclonal Antibodies to Matriptase

The cDNA sequences encoding the heavy and light chain variable regions of the Matriptase_A1 monoclonal antibodies were obtained using standard PCR techniques and were sequenced using standard DNA sequencing techniques.

The antibody sequences may be mutagenized to revert back to germline residues at one or more residues.

The nucleotide and amino acid sequences of the heavy chain variable region of Matriptase_A1 are set forth in SEQ ID NOs:3 and 1, respectively.

The nucleotide and amino acid sequences of the light chain variable region of Matriptase_A1 are set forth in SEQ ID NOs:4 and 2, respectively.

Comparison of the Matriptase_A1 heavy chain immunoglobulin sequence to the known human germline immunoglobulin heavy chain sequences demonstrated that the Matriptase_A1 heavy chain utilizes a $V_H$ segment from murine germline $V_H$ 3-23 and a $J_H$ segment from human germline $J_H$JH4b. Further analysis of the Matriptase_A1 $V_H$ sequence using the Kabat system of CDR region determination led to the delineation of the heavy chain CDR1, CDR2 and CDR3 regions as shown in SEQ ID NOs: 5, 6 and 7, respectively. The alignments of the Matriptase_A1 CDR1, CDR2 and CDR3 $V_H$ sequences to the germline $V_H$ 3-23 and germline $J_H$ JH4b sequence are shown in FIG. 2a.

Comparison of the Matriptase_A1 light chain immunoglobulin sequence to the known murine germline immunoglobulin light chain sequences demonstrated that the Matriptase_A1 light chain utilizes a $V_K$ segment from human germline $V_K$ A27 and a $J_K$ segment from human germline $J_K$JK2. Further analysis of the Matriptase_A1 $V_K$ sequence using the Kabat system of CDR region determination led to the delineation of the light chain CDR1, CDR2 and CDR3 regions as shown in SEQ ID NOs:8, 9 and 10, respectively. The alignments of the Matriptase_A1 CDR1, CDR2 and CDR3 $V_K$ sequences to the germline $V_K$ A27 and germline $J_K$JK2 sequences are shown in FIG. 2b.

Example 3: Screening Antigen Specific Antibody Using Enzyme-Linked Immunosorbent Assay (ELISA)

The specificity of Matriptase_A1 to the extra-cellular stem region of matriptase was determined by Enzyme-Linked Immunosorbent Assay (ELISA).

310 ug/ml of Matripase Stem protein was diluted in ELISA coating buffer (100 mm Sodium Carbonate/Bicarbonate) to 0.1 ug/ml, transferred into wells at 100 ul and incubated at 4° C. overnight.

After incubation, the wells were washed three times with PBST. 200 ul of SuperBlock (Thermo Scientific) was then added to each well and incubated for 30 min at 25° C., after which the wells were washed three more times with PBST.

Matriptase_A1, serially diluted from 0.01 to 30 umol/L in PBS and 0.1% BSA, was transferred into wells at 100 ul and incubated at 25° C. for 1 hr, the wells were then washed three times with PBST. Goat-anti-human IgG kappa specific-HRP (Lot# NG1876246) and Goat-anti-human IgG FC specific (Lot#96091) were serially diluted from 0.01 to 30 umol/L and transferred at 100 ul to each of the wells, which were then incubated at 25° C. for 1 hr and then washed again three times with PBST. 100 ul of TMB substrate was then added to each well and incubated again at 25° C. for approximately 1 hr, after which 100 ul of 1N HCL was added to each well.

Figure 3:
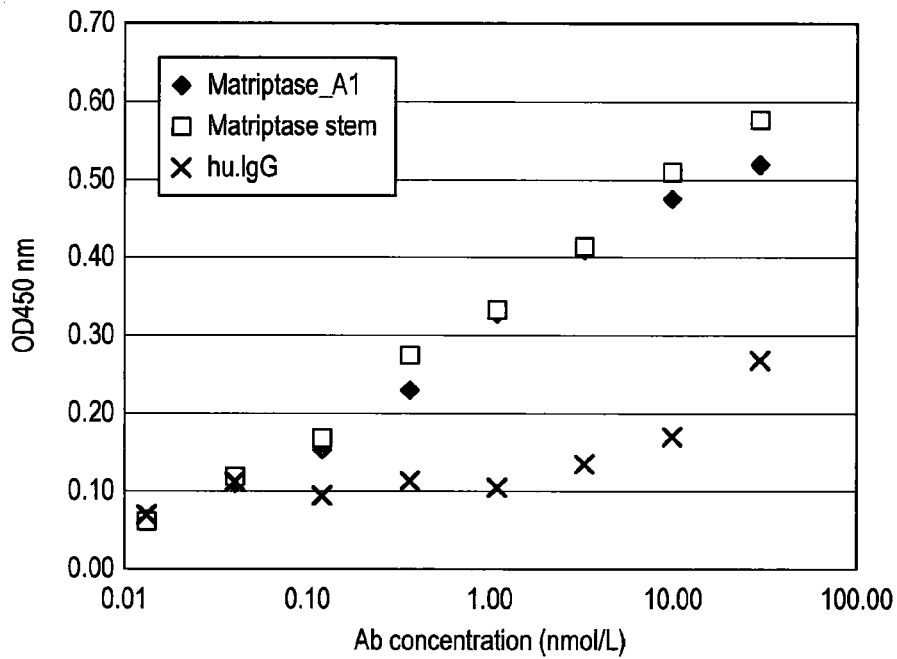
FIG. 3 shows Matriptase_A1 binding to the Matriptase-Stem using ELISA.

The results were read using Thermo Varioskan at 450 nm (See FIG. 3). These show that Matriptase_A1 binds to the stem of matriptase.

Example 4: Immunohistochemistry Using Monoclonal Antibody to Matriptase

Using the following Reference Protocol, Matriptase_A1 was used in IHC experiments at 20 ug/ml. Under these conditions significant staining was observed in colorectal cancer, gastric cancer, prostate cancer and breast cancer for tissue sections prepared as FFPE or frozen formats. The same conditions were used to test binding of Matriptase_A1 on normal human tissues Deparaffinisation and Rehydration Slides were heated for 2 hr at 60° C. in 50 ml Falcons in a water bath with no buffer. Each Falcon had one slide or two slides back-to back with long gel loading tip between them to prevent slides from sticking to each other. Slides were deparaffinised in EZ-DeWax (BioGenex, CA, USA) for 5 min in black slide rack, then rinsed well with the same DeWax solution using 1 ml pipette, then washed with water. Slides were placed in a coplin jar filled with water until the pressure cooker was ready; the water was changed a couple of times.

Antigen Retrieval

Water was exchanged for antigen retrieval solution=1× citrate buffer, pH 6 (DAKO). Antigen was retrieved by the pressure cooker method. The slides in the plastic coplin jar in antigen retrieval solution were placed into a pressure cooker which was then heated up to position 6 (the highest setting). 15-20 min into the incubation, the temperature was reduced to position 3 and left at that (when the temperature inside the pressure cooker was 117° C.) for another 20-25 min. Then the hob was switched off and the cooker was placed onto the cold hob and the pressure was released by carefully moving the handle into the position between "open" and "closed". The whole system was left to release the pressure and to cool down for another 20 min. The lid was opened and samples taken out to rest on the bench. The slides were washed 1×5 min with PBS-3T (0.5 L PBS+3 drops of Tween-20) and the slides were placed in PBS.

Staining

After antigen retrieval, slides were mounted in the Shandon Coverplate system. Trapping of air bubbles between the slide and plastic coverplate was prevented by placing the coverplate into the coplin jar filled with PBS and gently sliding the slide with tissue sections into the coverplate. The slide was pulled out of the coplin jar while holding it tightly together with the coverplate. The assembled slide was placed into the rack, letting PBS trapped in the funnel and between the slide and coverplate to run through. Slides were washed with 2×2 ml (or 4×1 ml) PBS-3T and 1×2 ml PBS, waiting until all PBS had gone through the slide and virtually no PBS was left in the funnel.

Endogenous peroxide blockade was performed using peroxidase blocking reagent (S2001, DAKO). 1-4 drops of peroxide solution was used per slide and incubated for 5 minutes. The slides were rinsed with water and then once with 2 ml PBS-3T and once with 2 ml PBS; it was important to wait until virtually no liquid was left in the funnel before adding a new portion of wash buffer.

The primary antibody was diluted with an Antibody diluent reagent (DAKO). Optimal dilution was determined to be 0.5 µg/ml. 50-200 µl of diluted primary antibody was applied to each section and/or tissue microarray; taking care to cover the whole tissue. The slide was gently tapped to distribute the antibody evenly over the section or a pipette tip was used over the top of the section. The slide was incubated for 45 min in a moist chamber at room temperature. Slides were washed with 2×2 ml (or 4×1 ml) PBS-3T and then 1×2 ml PBS, waiting until all PBS had gone through the slide and virtually no PBS was left in the funnel. The corresponding donkey anti-goat IgG:HRP (1500P, 1 mg/ml, Serotec) was applied at 1:1000 and incubated for 35 min at room temperature. The slides were washed as above. The DAB substrate was made up in dilution buffer; 2 ml containing 2 drops of substrate was enough for 10 slides. The DAB reagent was applied to the slides by applying a few drops at a time. All of the DAB was distributed between the slides. The slides were incubated for 10 min. The slides were washed 1×2 ml (or 2×1 ml) with PBS-3T and 1×2 ml (or 2×1 ml) with PBS, waiting until all PBS had gone through the slide and virtually no PBS was left in the funnel. Hematoxylin (DAKO) was applied; 1 ml was enough for 10 slides and slides were incubated for 1 min at room temperature. The funnels of the Shandon Coverplate system were filled with 2 ml of water and let to run through. When slides were clear of the excess of hematoxylin, the system was disassembled, tissue sections and/or arrays were washed with water from the wash bottle and placed into a black slide rack. Tissues were rehydrated by incubating in EZ-DeWax for 5 min and then in 95% ethanol for 2-5 min. Slides were left to dry on the bench at room temperature and then mounted in mounting media and covered with coverslip.

Results

Expression of Matriptase was found in 95%-100% of colorectal cancer (Table 2) clinical samples, 97% of gastric cancer (Table 1) samples, 100% of prostate cancer samples and 75% of breast cancer samples tested.

In the epithelial origin cells where the target was observed, detected expression levels were significantly lower than comparable tumor tissues. Normal expression was observed sporadically in kidney tubules and also the gastrointestinal tract.

TABLE 1

IHC with Matriptase_A1 in Gastric cancer: The table below summarizes the expression of the stem protein on the cell surface of an array of 41 stomach cancer samples and 8 normal stomach samples.

| Pathology | Grade | TMN | Type | Result |
|---|---|---|---|---|
| Adenocarcinoma | 1 | T2N0M0 | Malignant | ++ |
| Adenocarcinoma | 1 | T2N1M0 | Malignant | 0 |
| Adenocarcinoma | 1 | T3N2M0 | Malignant | +++ |
| Adenocarcinoma | 1 | T3N1M0 | Malignant | +++ |
| Adenocarcinoma | 1 | T3N4M1 | Malignant | +++ |
| Adenocarcinoma | 1 | T3N0M0 | Malignant | +++ |
| Adenocarcinoma | 1 | T3N0M0 | Malignant | ++ |
| Adenocarcinoma | 1 | T3N1M0 | Malignant | + |
| Adenocarcinoma | 1 | T3N0M0 | Malignant | +++ |
| Papillary adenocarcinoma | 1-2 | T3N1M0 | Malignant | ++ |
| Adenocarcinoma | 1-2 | T3N3M0 | Malignant | ++ |
| Adenocarcinoma | 1 | T3N1M0 | Malignant | ++ |
| Adenocarcinoma | 1 | T3N1M0 | Malignant | +++ |
| Papillary adenocarcinoma | 2 | T3N1M0 | Malignant | +++ |
| Adenocarcinoma | 1 | T3N1M0 | Malignant | ++ |
| Adenocarcinoma | 2 | T3N1M0 | Malignant | ++ |
| Adenocarcinoma | 2 | T3N1M0 | Malignant | ++ |
| Adenocarcinoma | 1-2 | T3N1M0 | Malignant | ++ |
| Adenocarcinoma | 2 | T2N1M0 | Malignant | ++ |

TABLE 1-continued

IHC with Matriptase_A1 in Gastric cancer: The table below summarizes the expression of the stem protein on the cell surface of an array of 41 stomach cancer samples and 8 normal stomach samples.

| Pathology | Grade | TMN | Type | Result |
|---|---|---|---|---|
| Papillary adenocarcinoma | 2 | T3N1M0 | Malignant | ++ |
| Adenocarcinoma | 2 | — | Malignant | +++ |
| Adenocarcinoma | 2 | T3N1M0 | Malignant | +++ |
| Papillary adenocarcinoma | 2 | T3N2M0 | Malignant | +++ |
| Adenocarcinoma | 2 | T3N3M0 | Malignant | +++ |
| Adenocarcinoma | 2 | T2N0M0 | Malignant | ++ |
| Adenocarcinoma | 2 | T3N1M0 | Malignant | +++ |
| Adenocarcinoma | 2-3 | T3N1M0 | Malignant | + |
| Adenocarcinoma | 2 | T2N3M0 | Malignant | 0 |
| Adenocarcinoma | 2 | T3N1M0 | Malignant | ++ |
| Adenocarcinoma | 3 | T3N0M0 | Malignant | +++ |
| Adenocarcinoma | 2-3 | T2N1M0 | Malignant | +++ |
| Adenocarcinoma | 3 | T3N2M0 | Malignant | ++ |
| Adenocarcinoma | 3 | T3N1M0 | Malignant | − |
| Adenocarcinoma | 3 | T3N0M0 | Malignant | + |
| Adenocarcinoma | 3 | T3N0M0 | Malignant | +++ |
| Adenocarcinoma | 3 | T2N0M0 | Malignant | ++ |
| Adenocarcinoma | 3 | T3N2M0 | Malignant | + |
| Adenocarcinoma | 3 | T3N0M0 | Malignant | +++ |
| Adenocarcinoma | 3 | T3N2M0 | Malignant | + |
| Adenocarcinoma | 3 | T3N1M0 | Malignant | ++ |
| Normal gastric tissue (smooth muscle tissue) | — | — | Normal | − |
| Normal gastric tissue | — | — | Normal | − |
| Normal gastric tissue | — | — | Normal | + |
| Normal gastric tissue | — | — | Normal | + |
| Normal gastric tissue | — | — | Normal | + |
| Normal gastric tissue | — | — | Normal | − |
| Normal gastric tissue | — | — | Normal | − |
| Normal gastric tissue | — | — | Normal | − |

TABLE 2

IHC with Matriptase_A1 in colorectal cancer: The table below summarizes the expression of the stem protein on the cell surface of an array of 54 colon cancer samples.

| Pathology | Grade | Type | TMN | Result |
|---|---|---|---|---|
| Papillary adenocarcinoma | 1 | T3N0M0 | Malignant | ++ |
| Papillary adenocarcinoma | 1 | T3N0M0 | Malignant | ++ |
| Tubular papillary adenocarcinoma | 1 | T3N0M0 | Malignant | ++ |
| Adenocarcinoma | 1 | T3N1M0 | Malignant | + |
| Adenocarcinoma | 1 | T3N1M0 | Malignant | + |
| Adenocarcinoma | 1 | T3N1M0 | Malignant | + |
| Adenocarcinoma | 1 | T3N1M0 | Malignant | + |
| Adenocarcinoma | 1-2 | T3N1M0 | Malignant | + |
| Adenocarcinoma | 1 | T3N1M0 | Malignant | + |
| Adenocarcinoma | 2 | T2N0M0 | Malignant | ++ |
| Adenocarcinoma | 2 | T2N0M0 | Malignant | ++ |
| Adenocarcinoma | 2 | T2N0M0 | Malignant | +++ |
| Adenocarcinoma | 1 | T3N1M0 | Malignant | + |
| Adenocarcinoma | 1 | T3N1M0 | Malignant | + |
| Adenocarcinoma | 1 | T3N1M0 | Malignant | + |
| Adenocarcinoma | 1 | T3 N0 | Malignant | +++ |
| Adenocarcinoma | 1 | T3 N0 | Malignant | ++ |
| Adenocarcinoma | 1 | T3 N0 | Malignant | ++ |
| Adenocarcinoma | 2 | T2N1M0 | Malignant | ++ |

TABLE 2-continued

IHC with Matriptase_A1 in colorectal cancer: The table below summarizes the expression of the stem protein on the cell surface of an array of 54 colon cancer samples.

| Pathology | Grade | Type | TMN | Result |
|---|---|---|---|---|
| Adenocarcinoma | 2 | T2N1M0 | Malignant | ++ |
| Adenocarcinoma | 2 | T2N1M0 | Malignant | ++ |
| Mucinous adenocarcinoma | 2 | T3N1M0 | Malignant | + |
| Mucinous adenocarcinoma | 2 | T3N1M0 | Malignant | + |
| Mucinous adenocarcinoma | 2 | T3N1M0 | Malignant | ++ |
| Adenocarcinoma | 2 | T3N0M0 | Malignant | ++ |
| Adenocarcinoma | 2 | T3N0M0 | Malignant | ++ |
| Adenocarcinoma | 2 | T3N0M0 | Malignant | ++ |
| Adenocarcinoma | 2 | T1N0M0 | Malignant | ++ |
| Adenocarcinoma | 2 | T1N0M0 | Malignant | ++ |
| Adenocarcinoma | 2 | T1N0M0 | Malignant | ++ |
| Adenocarcinoma | 2 | T3N0M0 | Malignant | +++ |
| Adenocarcinoma | 2 | T3N0M0 | Malignant | +++ |
| Adenocarcinoma | 2 | T3N0M0 | Malignant | +++ |
| Adenocarcinoma | 3 | T3N1M0 | Malignant | + |
| Adenocarcinoma | 3 | T3N1M0 | Malignant | ++ |
| Adenocarcinoma | 3 | T3N1M0 | Malignant | ++ |
| Adenocarcinoma | 2-3 | T3N1M0 | Malignant | + |
| Adenocarcinoma | 2-3 | T3N1M0 | Malignant | + |
| Adenocarcinoma | 2-3 | T3N1M0 | Malignant | + |
| Adenocarcinoma | 3 | T3N1M0 | Malignant | + |
| Adenocarcinoma | 3 | T3N1M0 | Malignant | + |
| Adenocarcinoma | 3 | T3N1M0 | Malignant | +++ |
| Adenocarcinoma | 2 | T3N1M0 | Malignant | ++ |
| Adenocarcinoma | 2 | T3N1M0 | Malignant | 0 |
| Adenocarcinoma | 2-3 | T3N1M0 | Malignant | +++ |
| Adenocarcinoma (sparse) | 2 | T3N0M0 | Malignant | ++ |
| Adenocarcinoma (sparse) | — | T3N0M0 | Malignant | 0 |
| Adenocarcinoma | 2 | T3N0M0 | Malignant | ++ |
| Adenocarcinoma | 3 | T3N1M0 | Malignant | + |
| Adenocarcinoma | 3 | T3N1M0 | Malignant | + |
| Adenocarcinoma | 3 | T3N1M0 | Malignant | + |
| Adenocarcinoma | 3 | T2N0M0 | Malignant | + |
| Adenocarcinoma with necrosis | 3 | T2N0M0 | Malignant | + |
| Adenocarcinoma | 3 | T2N0M0 | Malignant | + |

Example 5: Specificity of Monoclonal Antibodies to Matriptase. Determined by Flow Cytometry Analysis The specificity of antibodies against the Matriptase selected in Example 1 was tested by flow cytometry. To test the ability of the antibodies to bind to the cell surface Matriptase protein, the antibodies were incubated with the Matriptase-expressing cells. Cells were washed in FACS buffer (DPBS, 2% FBS), centrifuged and resuspended in 100 µl of the diluted primary Matriptase antibody (also diluted in FACS buffer). The antibody-cell line complex was incubated on ice for 60 min and then washed twice with FACS buffer as described above. The cell-antibody pellet was resuspended in 100 µl of the diluted secondary antibody (also diluted in FACS buffer) and incubated on ice for 60 min on ice. The pellet was washed as before and resuspended in 200 µl FACS buffer. The samples were loaded onto the BD FACScanto II flow sytometer and the data analyzed using the BD FACSdiva software.

Figure 4A:
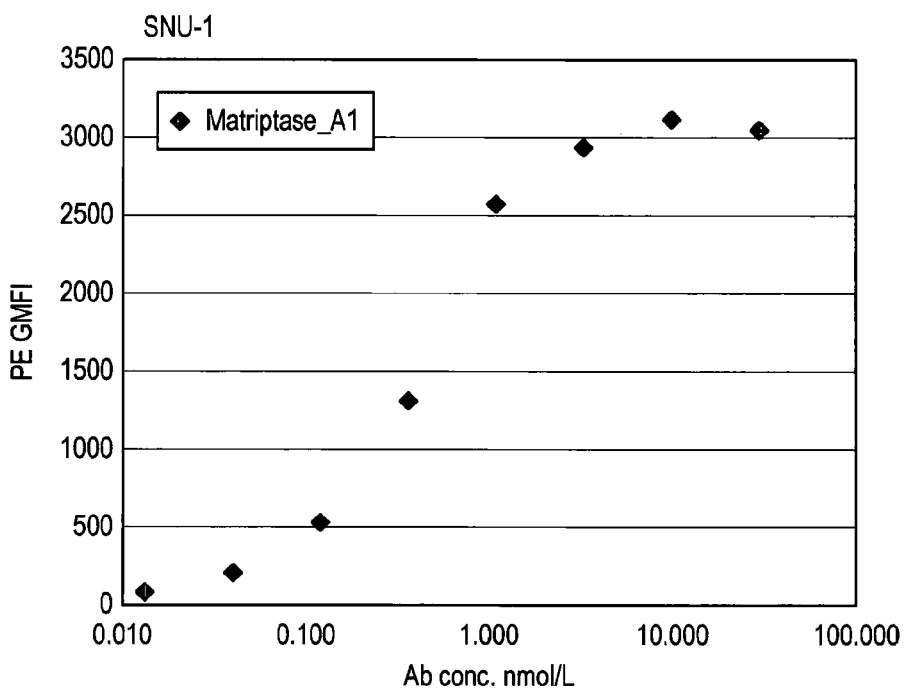
FIG. 4a shows results of flow cytometric analysis of Matriptase_A1 on SNU1 cells.
Figure 4B:
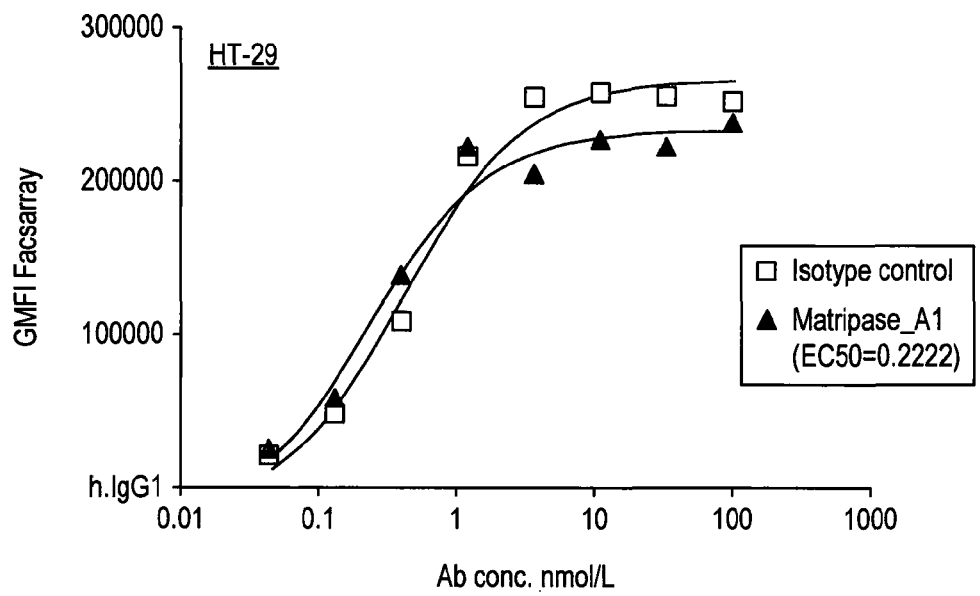
FIG. 4b depicts results of flow cytometric analysis of Matriptase_A1 on HT-29 cells.
Figure 4C:
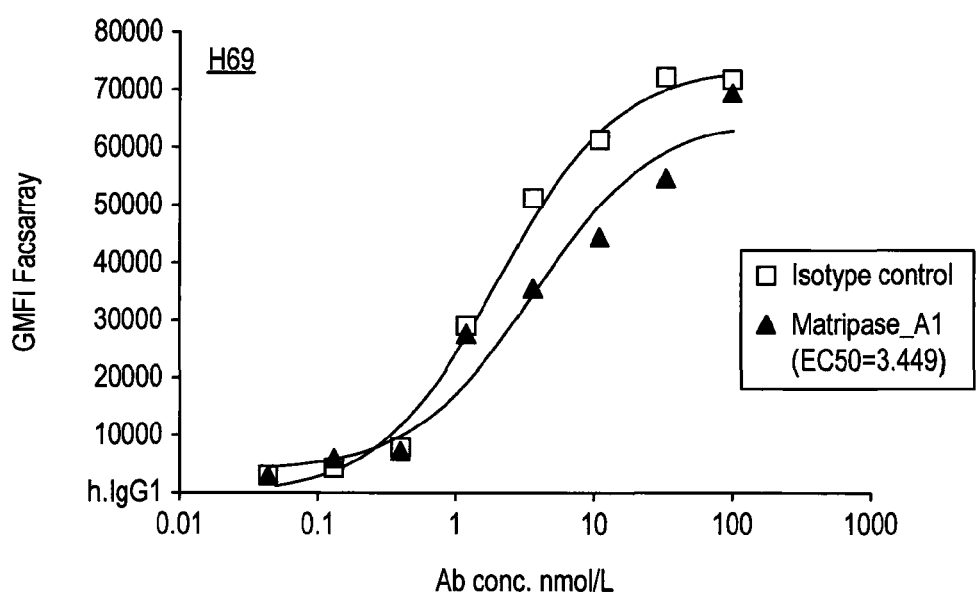
FIG. 4c depicts results of flow cytometric analysis of Matriptase_A1 on H69 cells.

The results of the flow cytometry analysis demonstrated that the monoclonal antibody Matriptase_A1 bound effectively to the cell-surface human Matriptase expressed in HT-29 and H69 cells (FIG. 4b). In addition to those cell-lines, Matriptase_A1 was also found to bind with high affinity to a number of other cell-lines including SNU-1 (FIG. 4a), A431 (epidermoid carcinoma), SW620 (colorectal adenocarcinoma), SKOV-3 (ovarian adenocarcinoma), MCF-7 (breast cancer) and A549 (human alveolar adenocarcinoma).

Example 6: Antibody-Dependent Cellular Cytotoxicity Mediated by Matriptase_A1

Following standard procedures, the CytoTox 96® Non-Radioactive Cytotoxicity Assay (Promega UK Ltd) was used to determine the ability of Matriptase_A1 anti-Matriptase mAb to kill Matriptase-expressing cells in the presence of effector cells via antibody dependent cellular cytotoxicity (ADCC with HT-29 and OVCAR8 cells).

Figure 5:
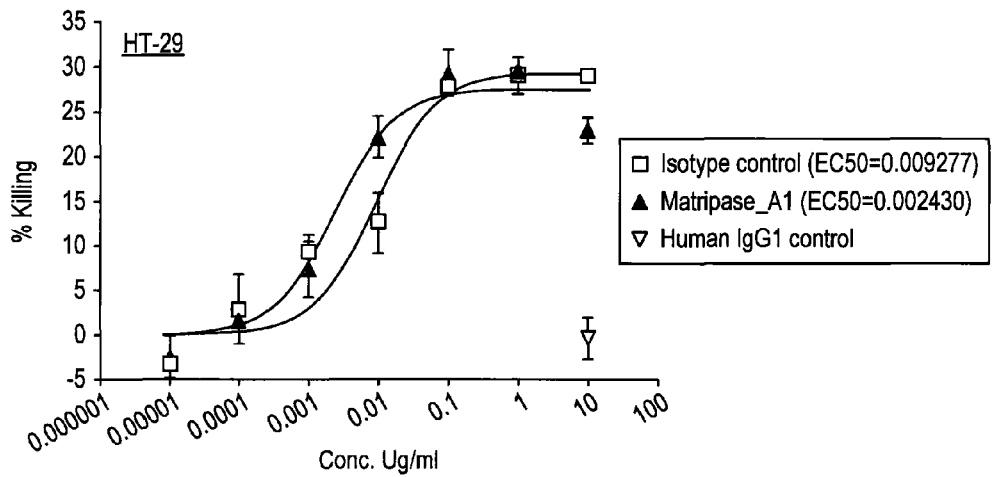
FIG. 5 depicts of Matriptase_A1 eliciting an antibody dependent cellular cytotoxicity (ADCC) response in the presence of effector cells

Using an antibody known to incite cell-kill via ADCC as a positive control and a human IgG1 isotype control as a negative control, the results show Matriptase_A1 was capable of eliciting ADCC on HT-29 cells. FIG. 5 shows Matriptase_A1 eliciting ADCC on HT-29 cells.

Example 7: Internalization of Matriptase_A1 Monoclonal Antibodies by HT-29 and H69 Cells Matriptase_A1 antibodies were shown to be internalized by HT-29 cells (human colon carcinoma cell line) and H69 cells (human small cell lung cancer cell line), upon binding to the cells using MabZAP assays. The MabZAP antibodies were bound to the primary antibodies. Next, the MabZAP complex was internalized by the cells. The entrance of Saporin into the cells resulted in protein synthesis inhibition and eventual cell death.

The MabZAP assay was conducted as follows. Each of the cells was seeded at a density of 5×103 cells per well. The anti-Matriptase monoclonal antibodies or an isotype control human IgG were serially diluted then added to the cells. The MabZAP were then added at a concentration of 50 µg/ml and the plates allowed to incubate for 48 and 72 hours. Cell viability in the plates was detected by CellTiter-Glo® Luminescent Cell Viability Assay kit (Promega, G7571) and the plates were read at 490 nM by a Luminomitor (Tuner BioSystems, Sunnyvale, Calif.). The data was analyzed by Prism (Graphpad).

Figure 6:
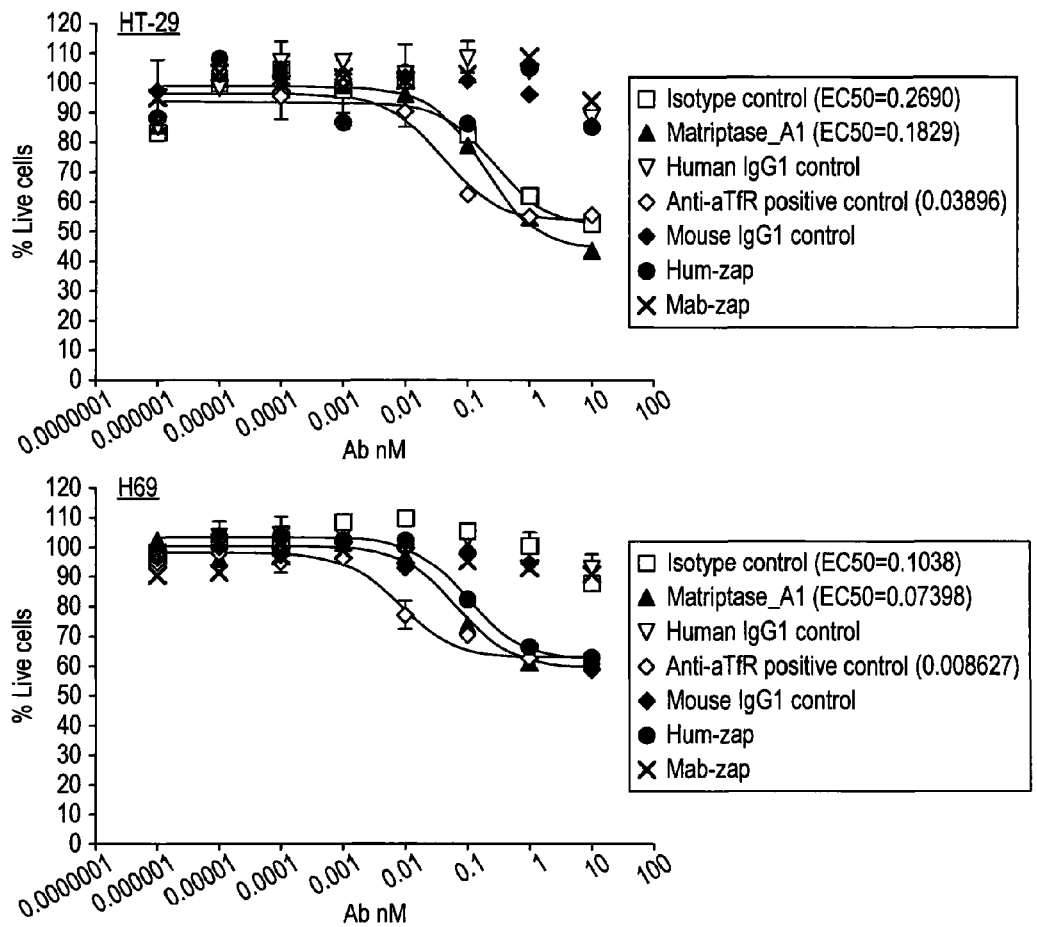
FIG. 6 depicts the internalization of Matriptase_A1 by HT-29 and H69 cells, using MabZAP assay.

FIG. 6 shows that Matriptase_A1 was efficiently internalized by HT-29 and H69 cells, with an EC50 of 0.1829 and 0.07398, respectively. These results demonstrate an increase in cytotoxic activity of Matriptase_A1 proportional to antibody concentration and other anti-Matriptase antibodies.

Example 8: Anti-Matriptase Antibody-Drug Conjugate Inhibits HT-29 Cell Growth in a Mouse Xenograft Model The effect of a Matriptase_A1 conjugate according to formula M (hereinafter referred to as "Matriptase_A1-Formula M conjugate") on the growth of colorectal carcinoma derived HT-29 cells in a mouse xenograft model was examined. In this xenograft model, SCID mice (CB17, from Charles River Laboratories, Hollister, Calif.) were implanted with 2.5×10⁶ HT-29 cells/mouse and the HT-29 cells were allowed to grow for ca. 30 days. The mice were then randomized and treated intraperitoneally (i.p.) with Matriptase_A1-Formula M conjugate (0.03, 0.1 and 0.3 µmole/kg). DT, and anti diptheria toxin antibody, was used as a non binding isotype control.

Figure 7A:
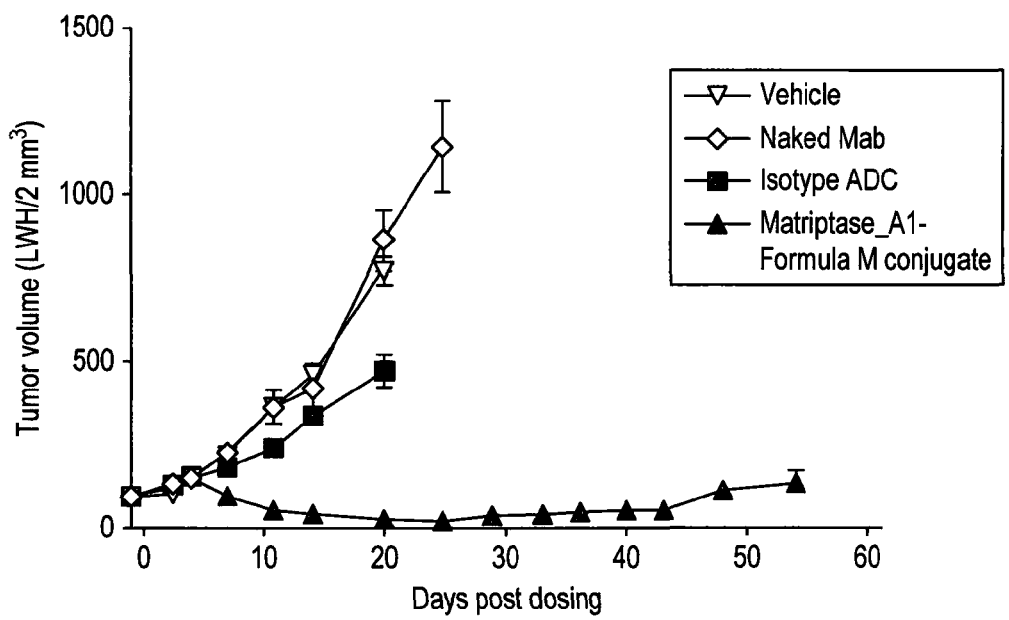
FIG. 7a shows a single dose (at 0.3 mole/kg: c.2 mg/kg) of toxin conjugated Matriptase_A1 was found to be curative.
Figure 7B:
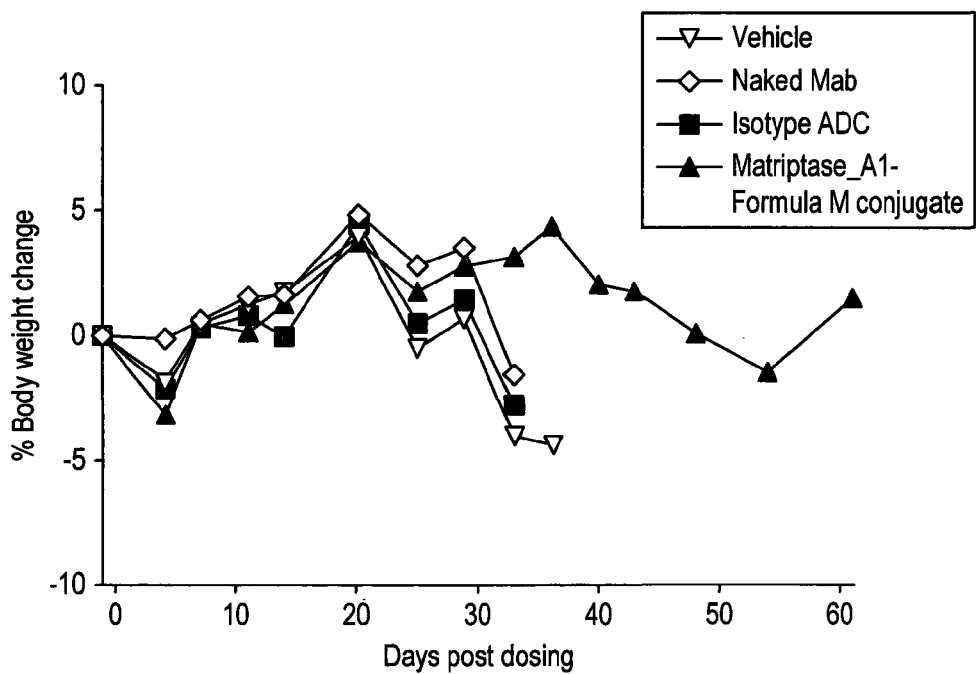
FIG. 7b shows the change in body weight over 60 days of dosing of Matriptase_A1 indicating an amelioration of tumor-induced cachexia.
Figure 7C:
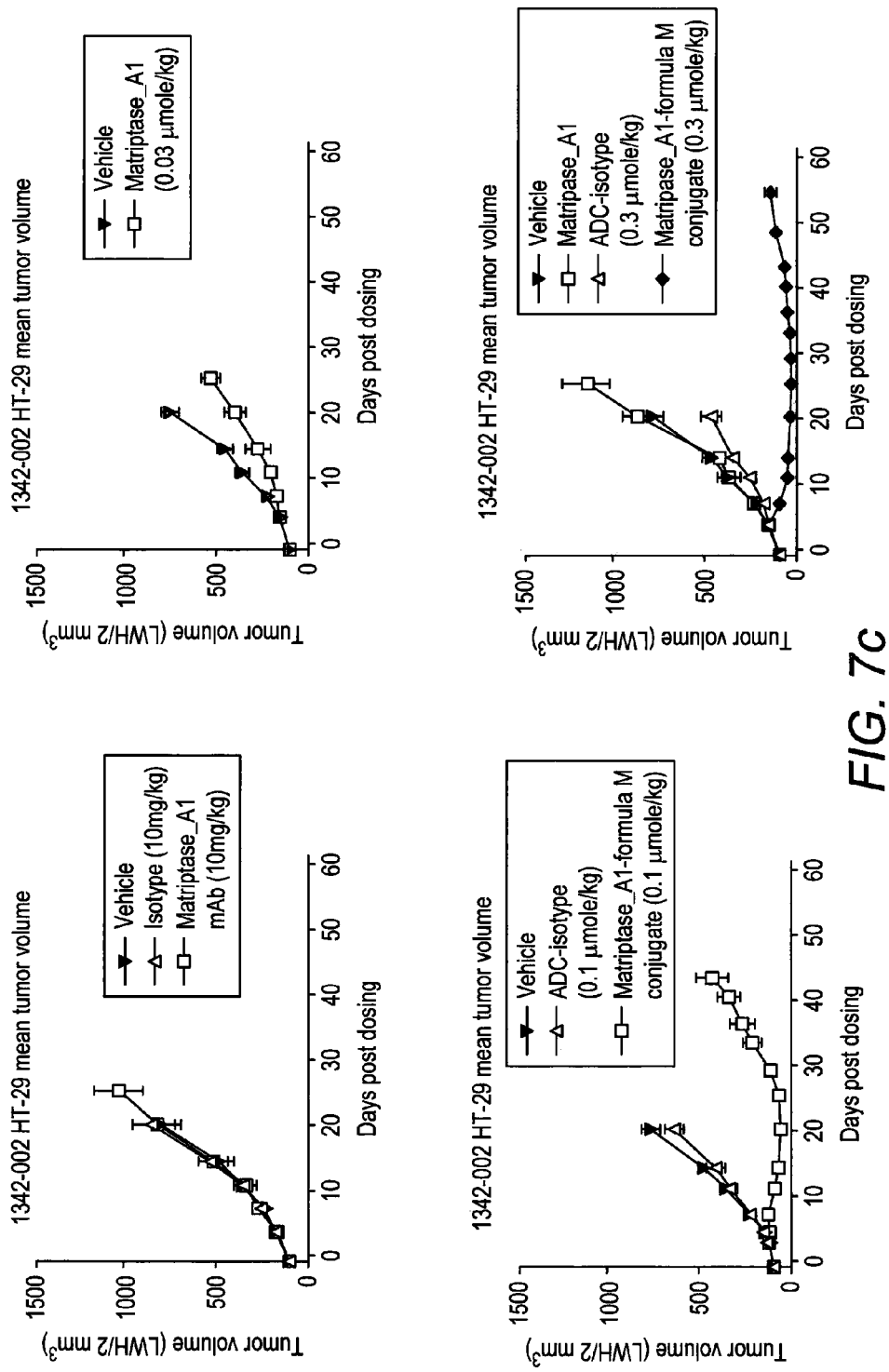
FIG. 7c shows alternate dose groups in the HT-29 ADC xenograft model revealing a dose response to treatment.
Figure 7D:
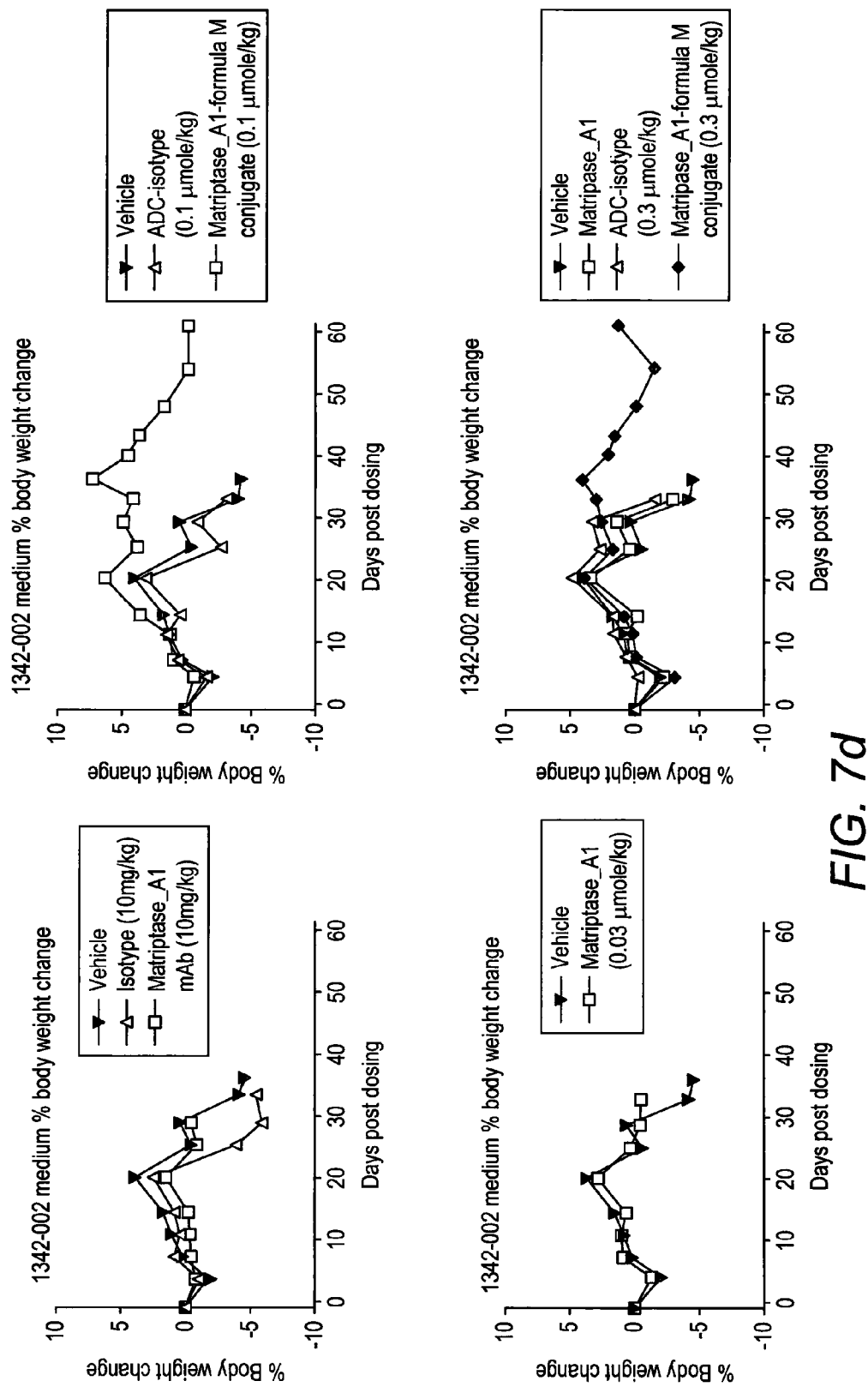
FIG. 7d shows alternate dose groups in the HT-29 ADC xenograft model revealing a dose response cachexia amelioration.

The results show treatment with the Matriptase_A1-Formula M conjugate significantly inhibited tumor growth rate in a dose dependent fashion. FIG. 7a shows a single dose (at 0.3 µmole/kg: c·2 mg/kg) of toxin conjugated mAb was found to be curative. FIG. 7b shows the change in body weight over 60 days of dosing indicating amelioration in tumor-induced cachexia. FIG. 7c shows alternate dose groups in the HT-29 ADC xenograft model revealing a dose dependent response to treatment. FIG. 7d shows alternate dose groups in the HT-29 ADC xenograft model revealing a dose dependent cachexia amelioration.

Example 9: Efficacy of MMAE-Conjugated and MMAF-Conjugated Anti-Matriptase Monoclonal Antibodies in Cancer Cell Lines Materials
Cell stripper (Non-enzymatic cell dissociation) (MT-25-056Cl) from Fisher Scientific, PA, USA.
PBS pH 7.4 (1×) (SH30028LS) from Fisher Scientific, PA, USA.
RPMI 1640 Media (MT-10-041-CM) from Fisher Scientific, PA, USA.
Cell Titer Glo (G7572) from Promega, Wis., USA.
Method
Cells were dissociated using cell stripper and counted. 5e3 cells/well were spun down into a pellet (for suspension cells, more can be used depending on the doubling time of the cells, such as 10e3 cells/well). The pellet was resuspended in culture media to a concentration of 1e5 cells/mL.

50 ul/well cell suspension was added to wells of a 96-well white sided, clear bottomed plate. Antibodies were diluted and titrated to 8 points (3-fold titrations) corresponding to concentrations between 0-20 nM (twice the test concentrations). Diluted antibodies or media (for untreated samples) (50 ul/well) were added to the appropriate wells. Excess media (200 ul/well) was added to the outside rows and columns of the plate to prevent evaporation. The plate was incubated for 72 h at 37 C.

The plate was removed from the incubator and incubated at room temperature for 30 minutes. Meanwhile Cell Titer Glo solution was thawed. The plate was flicked and washed 1× with 100 ul/well PBS (for suspension cells, plate is centrifuged first to pellet cells). 100 ul/well PBS and 100 ul Cell titer glo was added to each well and triturated to mix. The plate was incubated in the dark at room temperature for 15 minutes and visualized by microscopy to ensure efficient cell lysis occurred. The plate was then read on a Glomax luminometer.

Figure 8:
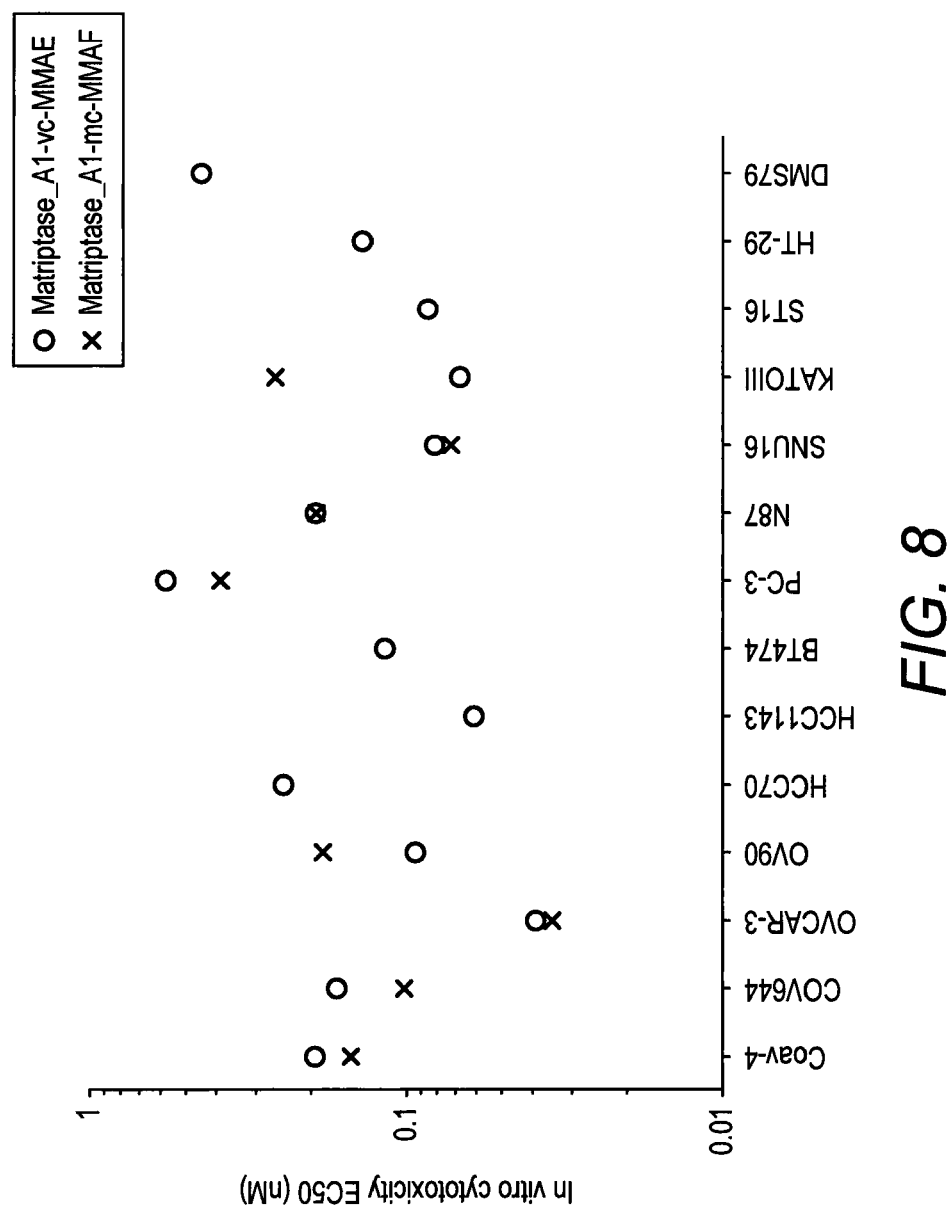
FIG. 8 depicts the EC50 values for ADC cytoxicity assays using anti-Matriptase antibodies conjugated to either MMAE or MMAF in various cancer cell lines.

Results
Table 3 shows the EC50 values for a number of human tumour cell lines in an ADC cytoxicity assay using anti-Matriptase antibodies conjugated to MMAE. The cell lines examined were Coav-4 (Human ovarian adenocarcinoma), COV644 (Human ovarian epithelial-mucinous carcinoma), OVCAR-3 (Human ovarian adenocarcinoma), OV90 (Human papillary serous adenocarcinoma), HCC70 (Human breast ductal carcinoma ER negative, PR negative and Her2 negative), HCC1143 (Human breast ductal carcinoma ER negative, PR negative and Her2 negative), BT474 (Human breast ductal carcinoma), PC-3 (Human prostate adenocarcinoma), N87 (Human gastric adenocarcinoma), SNU16 (Human gastric adenocarcinoma), KATOIII (Human gastric adenocarcinoma), ST16 (Human gastric adenocarcinoma), HT-29 (Human colorectal adenocarcinoma) and DMS79 (lung small cell carcinoma) cells. Table 3 also shows the EC50 values for the anti-Matriptase antibodies conjugated to MMAF in Coav-4, COV644, OVCAR-3, OV90, PC-3, N87, SNU16 and KATOIII cell lines. These results demonstrate cytotoxic activity of anti-Matriptase antibodies conjugated to MMAE and anti-Matriptase antibodies conjugated to MMAF at >1 nM (see FIG. 8).

TABLE 3

Summary for EC50 values for ADC Cytoxicity Assay against cancer cell lines

| Cell line | Matriptase_A1-vc-MMAE (EC50 nM) | Matriptase_A1-mc-MMAF (EC50 nM) |
|---|---|---|
| Coav-4 | 0.196 | 0.151 |
| COV644 | 0.166 | 0.102 |
| OVCAR-3 | 0.039 | 0.035 |
| OV90 | 0.094 | 0.185 |
| HCC70 | 0.248 | Not Calculated |
| HCC1143 | 0.061 | Not Calculated |
| BT474 | 0.118 | Not Calculated |
| PC-3 | 0.579 | 0.389 |
| N87 | 0.196 | 0.194 |
| SNU16 | 0.082 | 0.073 |
| KATOIII | 0.068 | 0.261 |
| ST16 | 0.086 | Not Calculated |
| HT-29 | 0.139 | Not Calculated |
| DMS79 | 0.444 | Not Calculated |

Example 10: Efficacy of MMAE-Conjugated and MMAF-Conjugated Anti-Matriptase Monoclonal Antibodies in Ovarian Cancer Xenograft Models The efficacy of Matriptase_A1_MMAE and Matriptase_A1_MMAF were tested in the OVACAR-3 nude mouse xenograft model.
Immunodeficient athymic nude mice were inoculated subcutaneously with OVACAR-3 (human ovarian adenocarcinoma) tumour cells. Tumours were allowed to establish and mice were sorted into seven treatment groups of 5-8 mice per group. When the mean tumour volume reached an average size of 167 mm3 per group, each group was treated with one of the following compounds, administered intravenously at the indicated dosages: Group 1 (Vehicle; 20 mM sodium succinate, pH 5.0, 6% trehalose, 0.04% polysorbate; n=8); Group 2 (Matriptase_A1_MMAE; 1 mg/kg; n=8), Group 3 (Matriptase_A1_MMAE; 3 mg/kg; n=8), Group 4 (Isotype control-MMAE; 3 mg/kg; n=5), Group 5 (Matriptase_A1_MMAF; 1 mg/kg; n=8), Group 6 (Matriptase_A1_MMAF; 3 mg/kg; n=8), Group 7 (Isotype control-MMAF; 3 mg/kg; n=5). Body weights (BW) were monitored, the mice were examined frequently for health and adverse side effects, and tumours were measured twice weekly. Mice were euthanized 82 days after tumour inoculation. Efficacy was determined from anti-tumour activity (mean tumour size in treatment group/mean tumour size in control group×100) and the increase in mean time-to-endpoint (TTE) in ADC-treated versus PBS-treated mice. The five largest tumours in vehicle-treated control mice on day 71 post inoculation were sampled processed by formalin fixation and paraffin embedded.

Results

Figure 9:
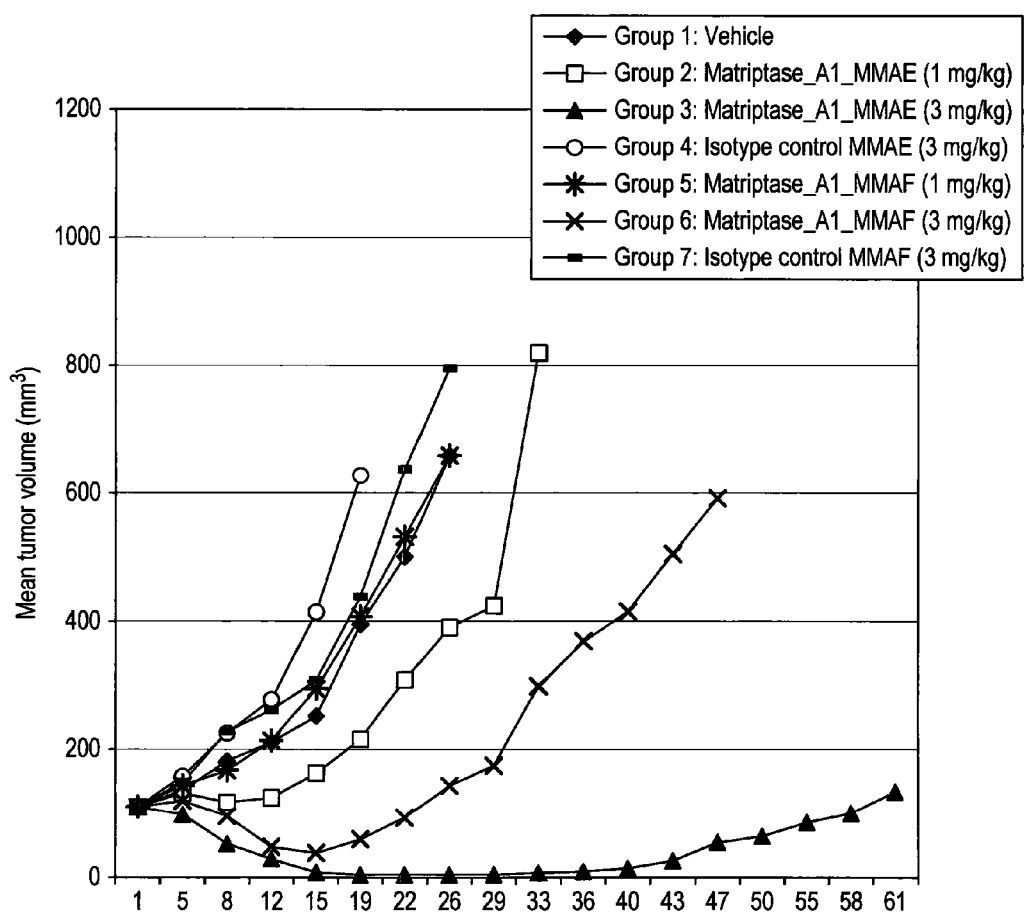
FIG. 9 depicts the efficacy of anti-Matriptase antibodies conjugated to either MMAE or MMAF in ovarian adenocarcinoma SCID mouse xenograft model.

FIG. 9 shows Matriptase_A1_MMAE and Matriptase_A1_MMAF each demonstrated dramatic anti-tumour activity in the OVACAR-3 nude mouse xenograft model compared to controls. Matriptase_A1_MMAE at 3 mg/kg yielded 8/8 survivors at day 61 of study, eight complete regressions, the maximum possible tumor growth delay (85%), and significant survival extension compared to its isotype control and vehicle control groups. Matriptase_A1_MMAF produced 68% TGD at 3 mg/kg, with two survivors, three partial regressions and one complete regression. All treatments were well-tolerated and no clinical signs of toxicity were observed. These data suggest the potential for ADCs directed towards Matriptase, for example Matriptase_A1_MMAE and Matriptase_A1_MMAF, to provide clinical benefit in the treatment of human triple negative breast cancer patients. As can be seen from these results Matriptase_A1_MMAE produced a surprisingly superior effect in this xenograft model.

Example 11: Toxicity of MMAE-Conjugated and MMAF-Conjugated Anti-Matriptase Monoclonal Antibodies in Cynomolgus Monkeys Ten monkeys were assigned to the study with one monkey/sex/group. Either vehicle (PBS), Matriptase_A1_MMAE or Matriptase_A1_MMAF was administered twice (on Day 1 and Day 29) by a 15-minute intravenous infusion at 0 mg/kg/dose (PBS, vehicle), 1 mg/kg/dose (Matriptase_A1_MMAE), 3 mg/kg/dose (Matriptase_A1_MMAE), 3 mg/kg/dose (Matriptase_A1_MMAF), 6 mg/kg/dose (Matriptase_A1_MMAF) as presented in Table 4. Blood samples were collected for toxicokinetic evaluations prior to dose initiation (Day 1), and 1, 2, 3, 7, 14, 21 and 28 days post each dose. Blood samples for clinical pathology analyses were collected prior to dose initiation (Day 1), and 1, 3, 7, 14, 21 and 28 days post each dose (28 days post the 1st dose was also served as the pre-dose time point for the 2nd dose). All study animals were euthanized and necropsied following the final blood collection on Day 57. The plasma separated from each blood draw was isolated, frozen and shipped to Oxford BioTherapeutics, Inc. to be analyzed for ADC concentration by ELISA.

TABLE 4

| Group | Treatment | Dose Level (mg/kg/dose) | Conc. (mg/mL) | Dose Volume (mL/kg) | Infusion rate (mL/kg/min) | No. of Animals |
|---|---|---|---|---|---|---|
| 1 | PBS | 0 | 0 | 2.0 | 0.1333 | 1 M/1 F |
| 2 | Matriptase_A1_MMAE | 1.0 | 0.50 | 2.0 | 0.1333 | 1 M/1 F |
| 3 | Matriptase_A1_MMAE | 3.0 | 1.50 | 2.0 | 0.1333 | 1 M/1 F |
| 4 | Matriptase_A1_MMAF | 3.0 | 1.50 | 2.0 | 0.1333 | 1 M/1 F |
| 5 | Matriptase_A1_MMAF | 6.0 | 3.00 | 2.0 | 0.1333 | 1 M/1 F |

CONCLUSION

Two doses of PBS, Matriptase_A1_MMAE (cleavable) up to 3.0 mg/kg/dose or Matriptase_A1_MMAF (non-cleavable) up to 6.0 mg/kg/dose, respectively, via 15-minute intravenous infusion in cynomolgus monkeys was well tolerated. There was no mortality or moribundity observed during the course of the study. No changes in clinical signs, body weights and body weight changes or food consumption were observed in the animals treated with Matriptase_A1_MMAE or Matriptase_A1_MMAF.

Increases in AST values were noted only on the day after each infusion for one Group 3 (Matriptase_A1_MMAE 3 mg/kg/day) male; both Group 4 (Matriptase_A1_MMAF 3 mg/kg/day) monkeys; and, both Group 5 (Matriptase_A1_MMAF 6 mg/kg/day) monkeys. The LDH values on the day after each infusion for the Group 3 male were also increased. There were no increases in either AST or LDH at any other time point. These findings were not associated with histopathological findings in the limited number of tissues examined. The increases are test article-related but not adverse. Increased BUN values for the Group 3 (Matriptase_A1_MMAE 3 mg/kg/day) male and female may be associated with test article administration, but given the lack of correlation with other study parameters and the magnitude of the increases, they are not toxicologically significant. There were no test article-related effects on hematology, coagulation or urinalysis parameters. There were no treatment related gross pathology findings or changes in absolute and relative organ weights. Histopathologically, the prominent number of lymphocytes in the spleen periarteriolar sheaths for the Group 2 (Matriptase_A1_MMAE 1 mg/kg/day) female; the Group 4 (Matriptase_A1_MMAF 3 mg/kg/day) female; and, the Group 5 (Matriptase_A1_MMAF 6 mg/kg/day) male are likely test article-related, but of no toxicological significance.

SUMMARY OF SEQUENCE LISTING

| SEQ ID No | Description | Sequence |
|---|---|---|
| 1 | VH_A1 aa | EVQLLESGGGLVQPGGSLRLSCAA SGFTFRNYDMSWVRQAPGKGLEWV SSISYSGGSTYYADSVKGRFTISR DNSKNTLSLQMNSLRAEDTAVYYC AKRGATPFDYWGQGSLVTVSS |
| 2 | VK_A1 aa | EIVLTQSPGTLSLSPGERATLSCR ASQSVSSSYLAWYQQKPGQAPRLL IYGASSRATGIPDRFSGSGSGTDF TLTISRLEPEDFAVYYCQQYGSSP YTFGQGTKLEIK |
| 3 | VH_A1 nt | GAGGTGCAACTGTTGGAGTCTGGG GGAGGCTTGGTACAGCCTGGGGGG TCCCTGAGACTCTCCTGTGCAGCC TCTGGATTCACCTTTAGGAACTAT GACATGAGCTGGGTCCGCCAGGCT CCAGGGAAGGGGCTGGAGTGGGTC TCAAGTATTAGTTATAGTGGTGGT AGCACATACTACGCAGACTCCGTG AAGGGCCGGTTCACCATCTCCAGA GACAATTCCAAGAATACGCTGTCT CTGCAAATGAACAGCCTGAGAGCC GAGGACACGGCCGTTTATTACTGT GCGAAAGGGGGCTACCCCATTT GACTACTGGGGCCAGGGATCCCTG GTCACCGTCTCCTCA |
| 4 | VK_A1 nt | GAAATTGTGTTGACGCAGTCTCCA GGCACCCTGTCTTTGTCTCCAGGG GAAAGAGCCACCCTCTCCTGCAGG GCCAGTCAGAGTGTTAGCAGCAGT TACTTAGCCTGGTACCAGCAGAAA CCTGGCCAGGCTCCCAGGCTCCTC ATCTATGGTGCATCCAGCAGGGCC ACTGGCATCCCAGACAGGTTCAGT GGCAGTGGGTCTGGGACAGACTTC ACTCTCACCATCAGCAGACTGGAG CCTGAAGATTTTGCAGTGTATTAC TGTCAGCAGTATGGTAGCTCACCG |

SUMMARY OF SEQUENCE LISTING -continued

| SEQ ID No | Description | Sequence |
|---|---|---|
| | | TACACTTTTGGCCAGGGGACCAAG CTGGAGATCAAA |
| 5 | VH_A1_CDR1 aa | NYDMS |
| 6 | VH_A1_CDR2 aa | SISYSGGSTYYADSVKG |
| 7 | VH_A1_CDR3 aa | RGATPFDY |
| 8 | VK_A1_CDR1 aa | RASQSVSSSYLA |
| 9 | VK_A1_CDR2 aa | GASSRAT |
| 10 | VK_A1_CDR3 aa | QQYGSSPYT |
| 11 | VH_A1_CDR1 nt | AACTATGACATGAGC |
| 12 | VH_A1_CDR2 nt | AGTATTAGTTATAGTGGTGGTAGC ACATACTACGCAGACTCCGTGAAG GGC |
| 13 | VH_A1_CDR3 nt | AGGGGGGCTACCCCATTTGACTAC |
| 14 | VK_A1_CDR1 nt | AGGGCCAGTCAGAGTGTTAGCAGC AGTTACTTAGCC |
| 15 | VK_A1_CDR2 nt | GGTGCATCCAGCAGGGCCACT |
| 16 | VK_A1_CDR3 nt | CAGCAGTATGGTAGCTCACCGTAC ACT |
| 17 | 3-23 Germline (V) | EVQLLESGGGLVQPGGSLRLSCAA SGFTFSSYAMSWVRQAPGKGLEWV SAISGSGGSTYYADSVKGRFTISR DNSKNTLYLQMNSLRAEDTAVYYC AK |
| 18 | JH4b Germline (J) | RGATPFDYWGQGTLVTVSS |
| 19 | A27 Germline (V) | EIVLTQSPGTLSLSPGERATLSCR ASQSVSSSYLAWYQQKPGQAPRLL IYGASSRATGIPDRFSGSGSGTDF TLTISRLEPEDFAVYYCQQYGSSP |
| 20 | JK2 Germline (J) | YTFGQGTKLEIK |
| 21 | Matriptase Stem A | VQKVFNGYMRITNENFVDAYENSN STEFVSLASKVKDALKLLYSGVPF LGPYHKESAVTAFSEGSVIAYYWS EFSIPQHLVEEAERVMAEERVVML PPRARSLKSFVVTSVVAFPT |
| 22 | Matriptase Stem B | VQKVFNGYMRITNENFVDAYENSN STEFVSLASKVKDALKLLYSGVPF LGPYHKESAVTAFSEG |
| 23 | Matriptase Stem C | VQKVFNGYMRITNENFVDAYENSN STEFVSLASKVKDALKLLYSGVPF LGPYHKESAVTAFSEGSVIAYYWS EFSIPQHLVEEAERVMAEERVVML PPRARSLK |
| 24 | Matriptase Stem D | VQKVFNGYMRITNENFVDAYENSN STEFVSLASKVKDALKLLYSGVPF LGPYHKESAVTAFSEGSVIAYYWS EFSIPQHLVEEAERVMAEERVVML PPRARSLKSFVVTSVVAFPTDSK |
| 25 | Matriptase ECD | VVGGTDADEGEWPWQVSLHALGQG HICGASLISPNWLVSAAHCYIDDR GFRYSDPTQWTAFLGLHDQSQRSA PGVQERRLKRIISHPFFNDFTFDY |

SUMMARY OF SEQUENCE LISTING

| SEQ ID No | Description | Sequence |
|---|---|---|
| | | DIALLELEKPAEYSSMVRPICLPD ASHVFPAGKAIWVTGWGHTQYGGT GALILQKGEIRVINQTTCENLLPQ QITPRMMCVGFLSGGVDSCQGDSG GPLSSVEADGRIFQAGVVSWGDGC AQRNKPGVYTRLPLFRDWIKENTG V |
| 26 | Matriptase Full-length protein | MGSDRARKGGGGPKDFGAGLKYNS RHEKVNGLEEGVEFLPVNNVKKVE KHGPGRWVVLAAVLIGLLLVLLGI GFLVWHLQYRDVRVQKVFNGYMRI TNENFVDAYENSNSTEFVSLASKV KDALKLLYSGVPFLGPYHKESAVT AFSEGSVIAYYWSEFSIPQHLVEE AERVMAEERVVMLPPRARSLKSFV VTSVVAFPTDSKTVQRTQDNSCSF GLHARGVELMRFTTPGFPDSPYPA HARCQWALRGDADSVLSLTFRSFD LASCDERGSDLVTVYNTLSPMEPH ALVQLCGTYPPSYNLTFHSSQNVL LITLITNTERRHPGFEATFFQLPR MSSCCGGRLRKAQGTFNSPYYPGHY PPNIDCTWNIEVPNNQHVKVRFKF FYLLEPGVPAGTCPKDYVEINGEK YCGERSQFVVTSNSNKITVRFHSD QSYTDTGFLAEYLSYDSSDPCPGQ FTCRTGRCIRKELRCDGWADCTDH SDELNCSCDAGHQFTCKNKFCKPL FWVCDSVNDCGDNSDEQGCSCPAQ TFRCSNGKCLSKSQQCNGKDDCGD GSDEASCPKVNVVTCTKHTYRCLN GLCLSKGNPECDGKEDCSDGSDEK DCDCGLRSFTRQARVVGGTDADEG EWPWQVSLHAQGHICGASLISPNW LVSAAHCYIDDRGFRYSDPTQWTA FLGLHDQSRSAPGVQERRLKRII SHPFFNDFTFDYDIALLELEKPAE YSSMVRPICLPDASHVFPAGKAIW VTGWGHTQYGGTGALILQKGEIRV INQTTCENLLPQQITPRMMCVGFL SGGVDSCQGDSGGPLSSVEADGRI FQAGVVSWGDGCAQRNKPGVYTRL PLFRDWIKENTGV |
| 27 | Matriptase catalytic C-terminal serine protease domain | VVGGTDADEGEWPWQVSLHALGQG HICGASLISPNWLVSAAHCYIDDR GFRYSDPTQWTAFLGLHDQSQRSA PGVQERRLKRIISHPFFNDFTFDY DIALLELEKPAEYSSMVRPICLPD ASHVFPAGKAIWVTGWGHTQYGGT GALILQKGEIRVINQTTCENLLPQ QITPRMMCVGFLSGGVDSCQGDSG GPLSSVEADGRIFQAGVVSWGDGC AQRNKPGVYTRLPLFRDWIKENTG V |
| 28 | Matriptase stem Fc-fusion protein | VQKVFNGYMRITNENFVDAYENSN STEFVSLASKVKDALKLLYSGVPF LGPYHKESAVTAFSEGSVIAYYWS EFSIPQHLVEEAERVMAEERVVML PPRARSLKSFVVTSVVAFPTASGS GIEGRGLEPKSSDKTHTCPPCPAP ELLGGPSVFLFPPKPKDTLMISRT PEVTCVVVDVSHEDPEVKFNWYVD GVEVHNAKTKPREEQYNSTYRVVS VLTVLHQDWLNGKEYKCKVSNKAL PAPIEKTISKAKGQPREPQVYTLP PSRDELTKNQVSLTCLVKGFYPSD IAVEWESNGQPENNYKTTPPVLDS DGSFFLYSKLTVDKSRWQQGNVFS CSVMHEALHNHYTQKSLSLSPGK |
| 29 | VH FR1 | EVQLLESGGGLVQPGGSLRLSCAA SGFTFR |
| 30 | VH FR2 | WVRQAPGKGLEWVS |
| 31 | VH FR3 | RFTISRDNSKNTLSLQMNSLRAED TAVYYCAK |
| 32 | VH FR4 | WGQGSLVTVSS |
| 33 | VK FR1 | EIVLTQSPGTLSLSPGERATLSC |
| 34 | VK FR2 | WYQQKPGQAPRLLIY |
| 35 | VK FR3 | GIPDRFSGSGSGTDFTLTISRLEP EDFAVYYC |
| 36 | VK FR4 | FGQGTKLEIK |

The invention claimed is:

1. An isolated antibody, or an antigen-binding portion thereof, said antibody comprising:
   a) a heavy chain variable region comprising:
      i) a first vhCDR comprising SEQ ID NO: 5;
      ii) a second vhCDR comprising SEQ ID NO: 6; and
      iii) a third vhCDR comprising SEQ ID NO: 7; and
   b) a light chain variable region comprising:
      i) a first vlCDR comprising SEQ ID NO: 8;
      ii) a second vlCDR comprising SEQ ID NO: 9; and
      iii) a third vlCDR comprising SEQ ID NO: 10,
      wherein the antibody, or antigen-binding portion thereof, binds the antigen bound by an antibody, or antigen-binding portion thereof, comprising a heavy chain variable region comprising SEQ ID NO: 1 and a light chain variable region comprising SEQ ID NO: 2.

2. An isolated antibody, or an antigen-binding portion thereof, comprising a heavy chain variable region comprising SEQ ID NO: 1 and a light chain variable region comprising SEQ ID NO: 2.

3. An isolated antibody, or an antigen-binding portion thereof, according to claim 1 further comprising a covalently-attached moiety.

4. An isolated antibody, or an antigen-binding portion thereof, according to claim 3, wherein said moiety is a drug moiety or a radioactive moiety.

5. An isolated antibody, or an antigen-binding portion thereof, according to claim 4, wherein said drug is selected from the group consisting of a maytansinoid, a dolastatin, a hemiasterlin, an auristatin, a trichothecene, a calicheamicin, CC1065 and derivatives thereof.

6. The isolated antibody, or an antigen-binding portion thereof, according to claim 5, wherein said drug is a maytansinoid selected from the group consisting of MMAE and MMAF.

7. An isolated antibody according to claim 1, wherein said antibody induces antibody-dependent cell-mediated cytotoxicity (ADCC) and/or complement dependent cytotoxicity (CDC).

8. An isolated antibody according to claim 7, wherein the antibody is an engineered antibody having increased binding to Fc receptors and/or increased potency for ADCC, and/or a bispecific antibody.

9. A pharmaceutical composition comprising an antibody, or antigen binding portion thereof, according to claim 1, together with one or more pharmaceutically-acceptable diluents, excipients or carriers.

10. A nucleic acid encoding a heavy chain of the antibody, or an antigen-binding portion thereof, of claim 1.

11. A nucleic acid encoding a light chain of the antibody, or an antigen-binding portion thereof, of claim 1.

12. An expression vector comprising the nucleic acid of claim 10 operably linked to one or more regulatory elements.

13. An expression vector comprising the nucleic acid of claim 11 operably linked to one or more regulatory elements.

14. A host cell comprising the expression vector of claim 12.

15. A host cell comprising the expression vector of claim 13.

16. A host cell comprising:
   (i) a first expression vector comprising a nucleic acid encoding a heavy chain variable region comprising a first vhCDR comprising SEQ ID NO: 5, a second vhCDR comprising SEQ ID NO: 6, and a third vhCDR comprising SEQ ID NO: 7, operably linked to one or more regulatory elements; and;
   (ii) a second expression vector comprising a nucleic acid encoding a light chain variable region comprising a first vlCDR comprising SEQ ID NO: 8, a second vlCDR comprising SEQ ID NO: 9, and a third vlCDR comprising SEQ ID NO: 10, operably linked to one or more regulatory elements.

17. A method of making an antibody, or an antigen-binding portion thereof, comprising culturing a host cell according to claim 16 under conditions where the antibody or an antigen-binding portion thereof is expressed and optionally isolating the antibody, or an antigen-binding portion thereof.

18. A method of treating cancer comprising administering to a patient in need thereof an antibody, or an antigen-binding portion thereof, of claim 1.

19. The method according to claim 18, wherein the antibody, or antigen-binding portion thereof, is internalized.

20. The method according to claim 18, wherein the antibody, or antigen-binding portion thereof, comprises a covalently attached drug conjugate.

21. The method according to claim 20, wherein the covalently attached drug conjugate is a auristatin, preferably MMAE.

22. The method according to claim 18, wherein the antibody induces antibody-dependent cell-mediated cytotoxicity (ADCC) and/or complement dependent cytotoxicity (CDC).

23. The method of claim 18, wherein said cancer is selected from the group consisting of gastric cancer, colorectal cancer, prostate cancer, breast cancer, ovarian cancer, lung cancer, preferably SCLC, esophageal cancer, head and neck cancer, pancreatic cancer, lymphoma preferably non-Hodgkin's lymphoma and skin cancer.

24. An antibody, or an antigen-binding portion thereof, according to claim 1 for use in therapy or for use as a medicament.

* * * * *